US008968393B2

(12) United States Patent
Rothstein

(10) Patent No.: US 8,968,393 B2
(45) Date of Patent: Mar. 3, 2015

(54) SYSTEM AND METHOD FOR PERCUTANEOUS MITRAL VALVE REPAIR

(75) Inventor: Paul Rothstein, Elk River, MN (US)

(73) Assignee: Medtronic, Inc., Minneapolis, MN (US)

( * ) Notice: Subject to any disclaimer, the term of this patent is extended or adjusted under 35 U.S.C. 154(b) by 267 days.

(21) Appl. No.: 13/096,674

(22) Filed: Apr. 28, 2011

(65) Prior Publication Data

US 2012/0277853 A1   Nov. 1, 2012

Related U.S. Application Data

(63) Continuation-in-part of application No. 12/039,629, filed on Feb. 28, 2008.

(51) Int. Cl.
| | |
|---|---|
| A61F 2/24 | (2006.01) |
| A61B 17/064 | (2006.01) |
| A61B 17/068 | (2006.01) |
| A61B 17/00 | (2006.01) |

(52) U.S. Cl.
CPC ............. *A61F 2/2457* (2013.01); *A61B 17/064* (2013.01); *A61B 17/068* (2013.01); *A61B 17/0682* (2013.01); *A61F 2/2466* (2013.01); *A61B 17/0644* (2013.01); *A61B 2017/00243* (2013.01); *A61B 2017/00867* (2013.01); *A61B 2017/0641* (2013.01); *A61B 2017/0645* (2013.01); *A61B 2017/0649* (2013.01)
USPC ...................................................... 623/2.11

(58) Field of Classification Search
USPC .......................... 606/139, 151, 232; 623/2.11
See application file for complete search history.

(56) References Cited

U.S. PATENT DOCUMENTS

| | | | |
|---|---|---|---|
| 6,749,622 B2 * | 6/2004 | McGuckin et al. ........... 606/213 |
| 7,316,706 B2 | 1/2008 | Bloom et al. | |
| 2007/0203391 A1 | 8/2007 | Bloom et al. | |
| 2009/0222026 A1 | 9/2009 | Rothstein et al. | |
| 2009/0259304 A1 | 10/2009 | O'Beirne et al. | |
| 2009/0306685 A1 | 12/2009 | Fill | |
| 2010/0016958 A1 | 1/2010 | St. Goar et al. | |
| 2010/0023118 A1 | 1/2010 | Medlock et al. | |
| 2010/0030328 A1 * | 2/2010 | Seguin et al. ................ 623/2.11 |
| 2010/0042147 A1 | 2/2010 | Janovsky et al. | |
| 2010/0262167 A1 * | 10/2010 | Jelich et al. .................. 606/151 |

* cited by examiner

*Primary Examiner* — Gregory Anderson

(57) ABSTRACT

A system for minimally invasive repair of a mitral valve including a catheter, a capture body and a surgical fastener. The capture body includes legs extending from a center portion, and is self-transitionable from a collapsed arrangement to a normal arrangement in which the legs extend in a common wind direction. The fastener has a self-closing clip forming a loop in an undeflected arrangement. In a delivery state, the capture body and fastener are disposed within the catheter and forced to the collapsed and deflected arrangements, respectively. In a capture state, the capture body legs are distal the catheter and self-assume the normal arrangement for capturing chordae. In a release state, the fastener is released from the catheter and the clip self-transitions toward the undeflected arrangement for securing the mitral valve leaflets.

20 Claims, 64 Drawing Sheets

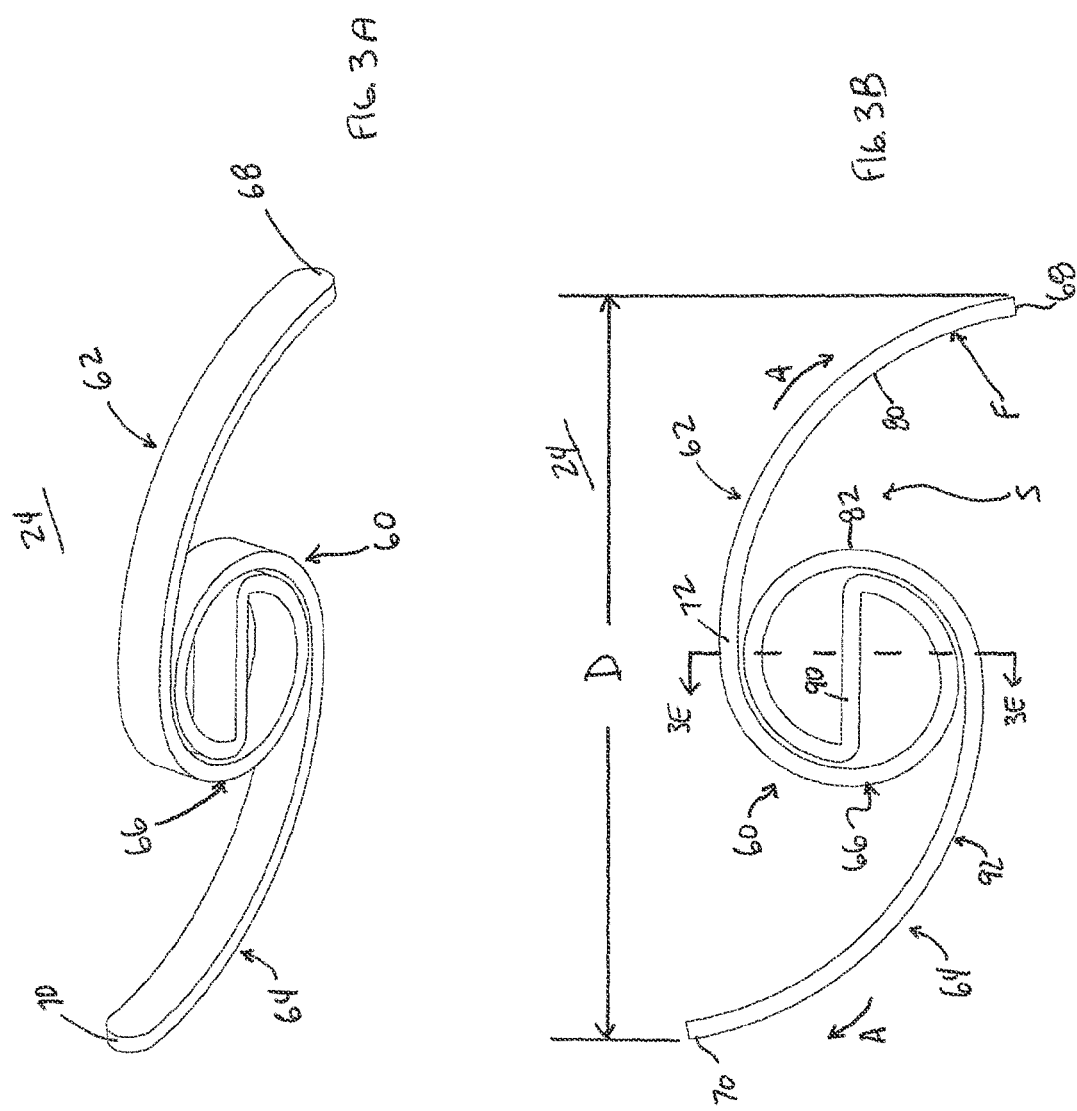

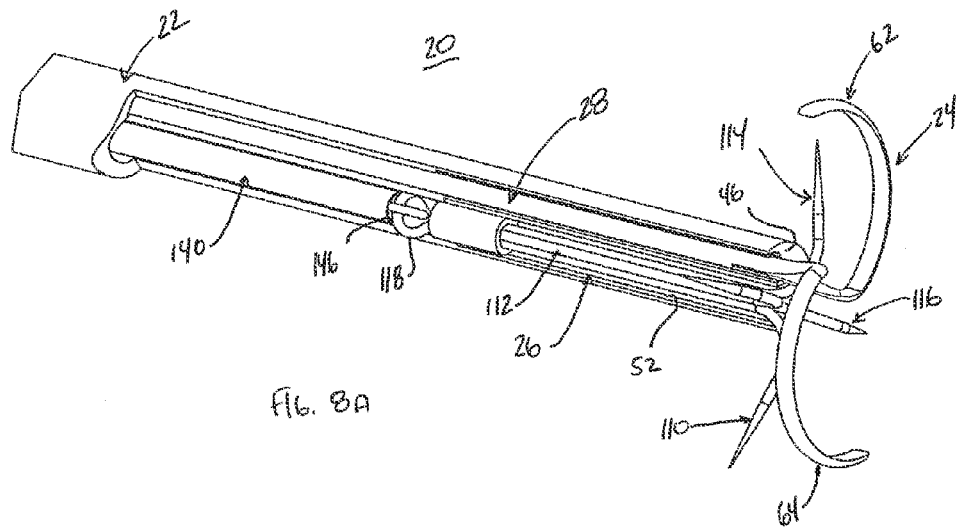
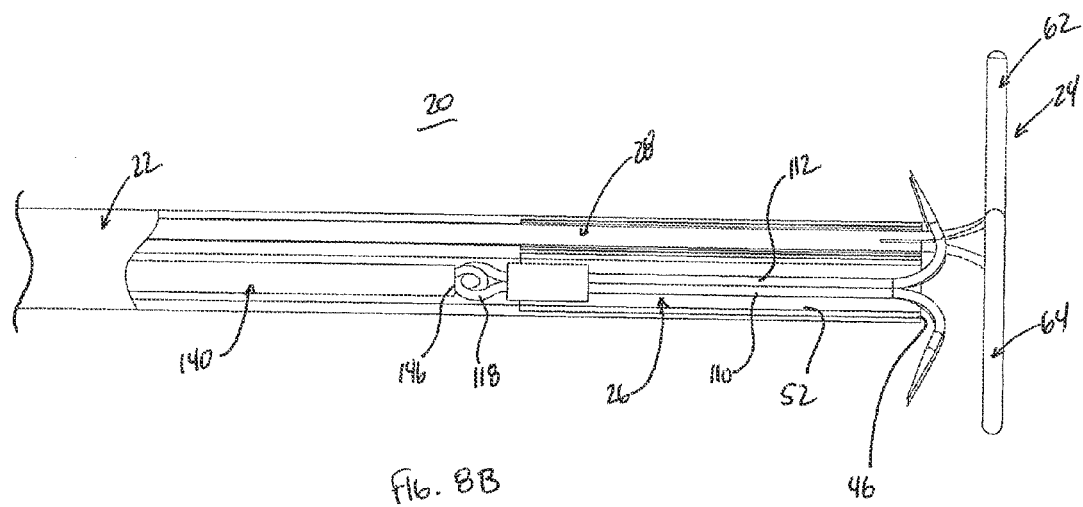

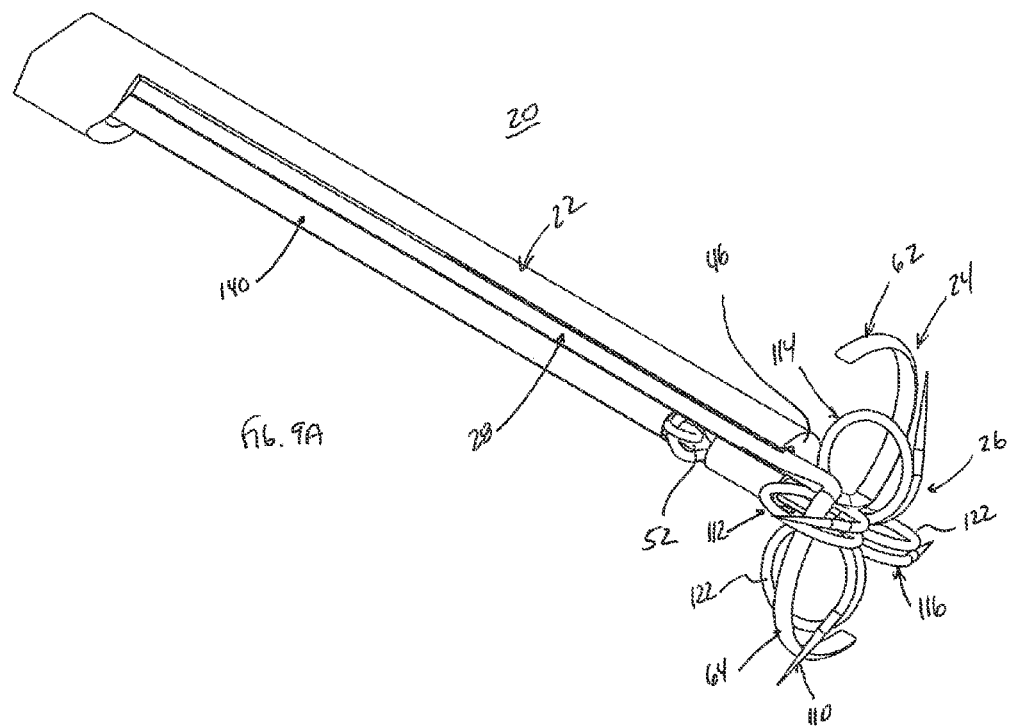
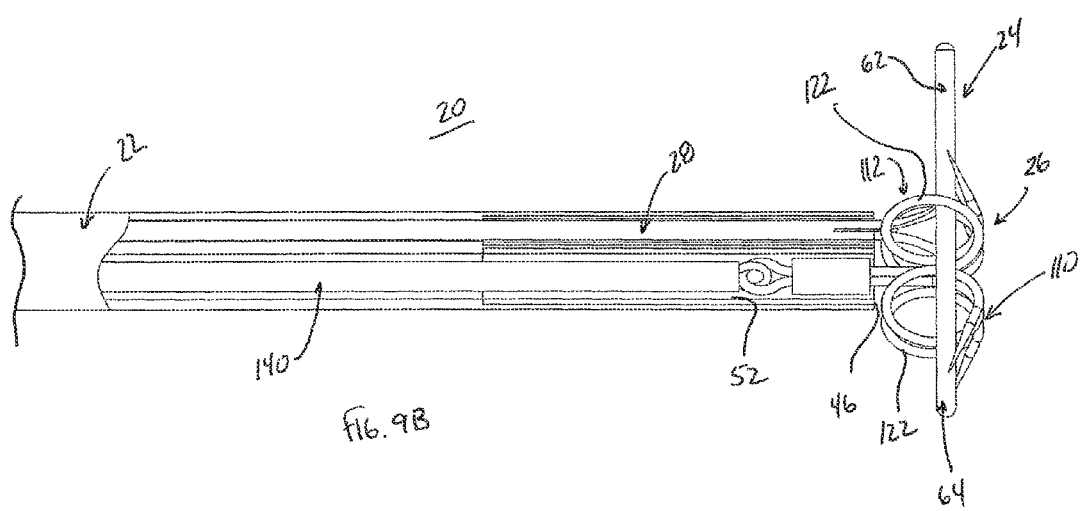

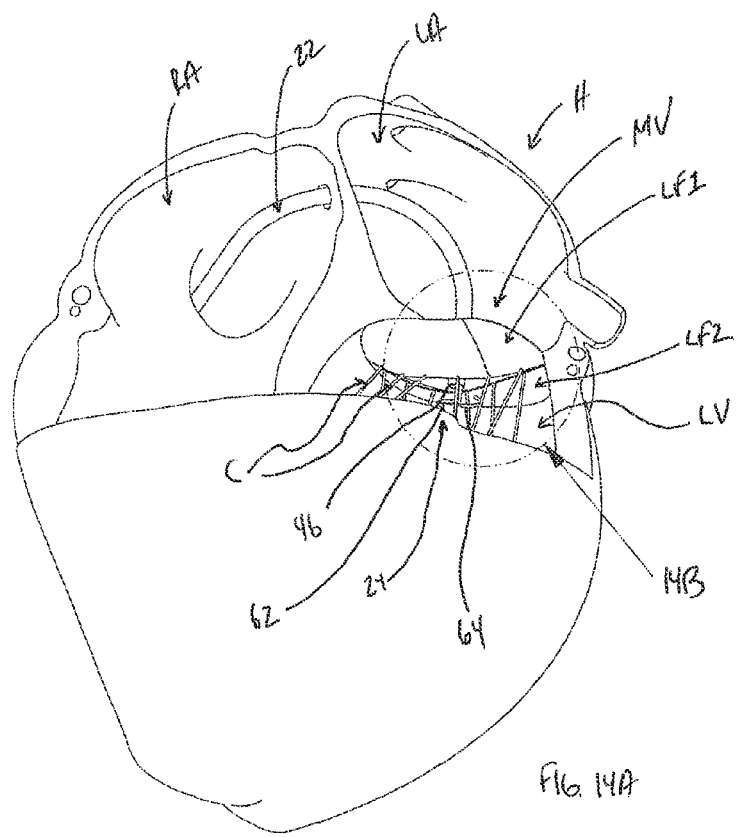
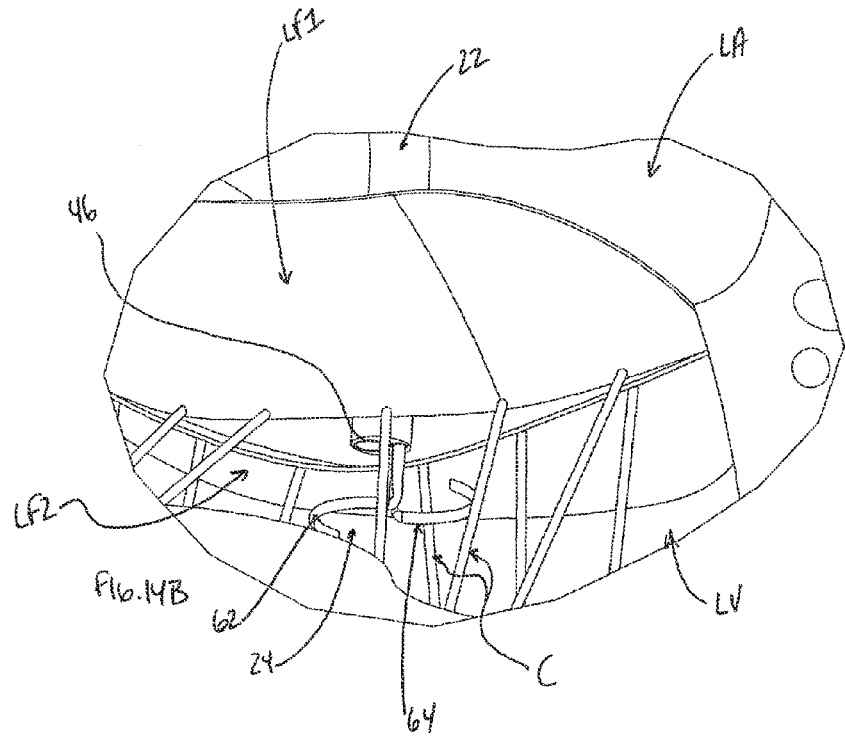
FIG. 14A
FIG. 14B

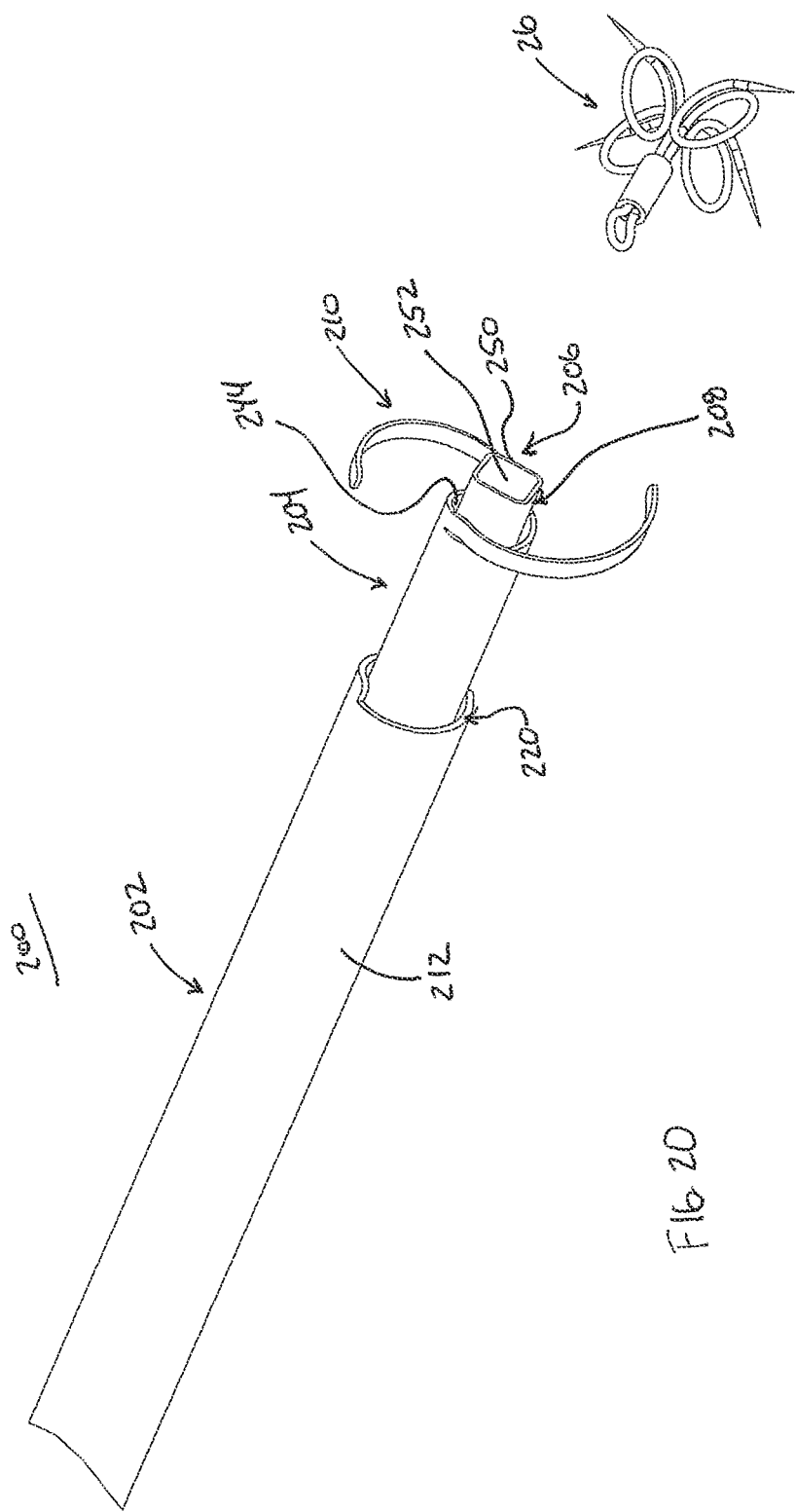

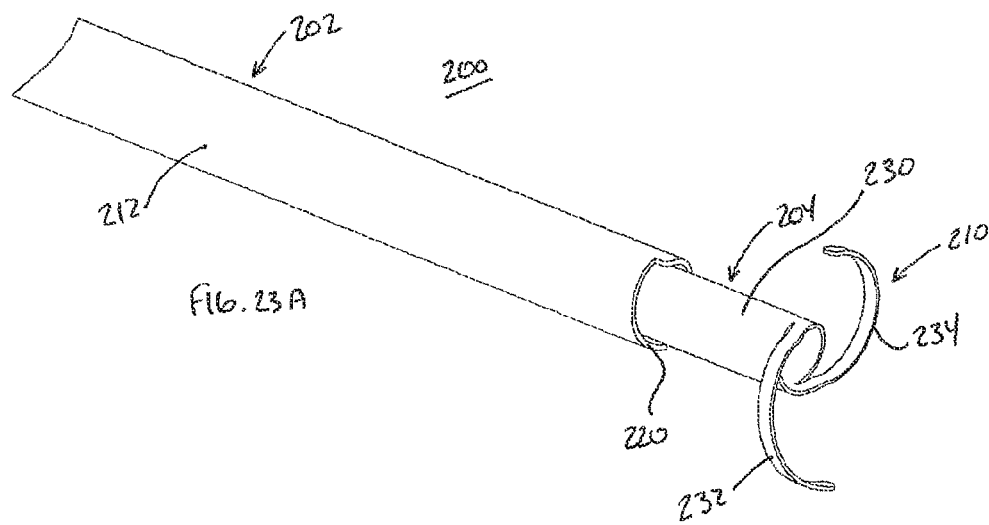
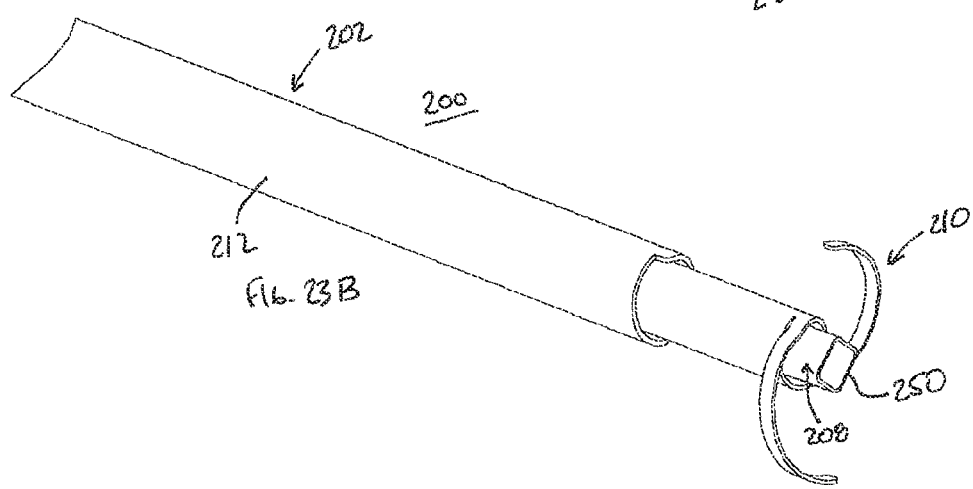
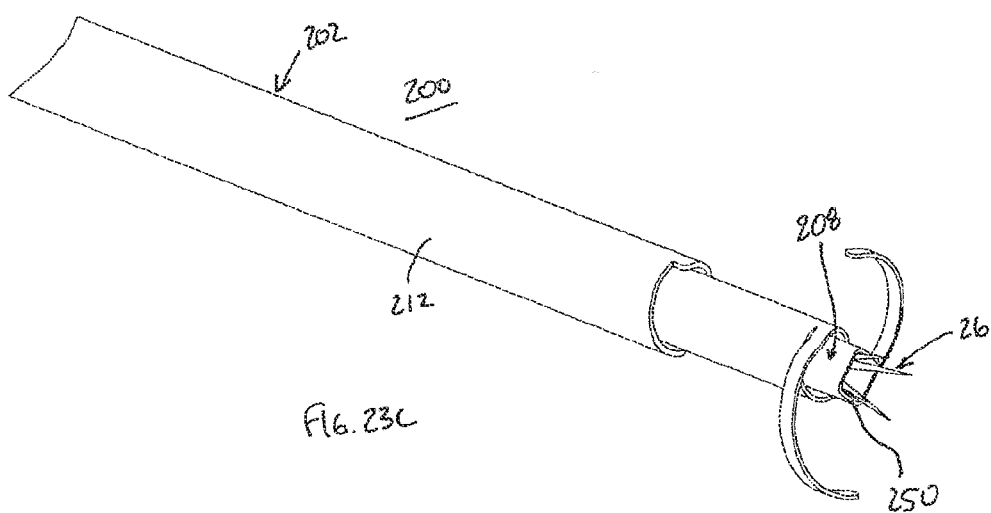

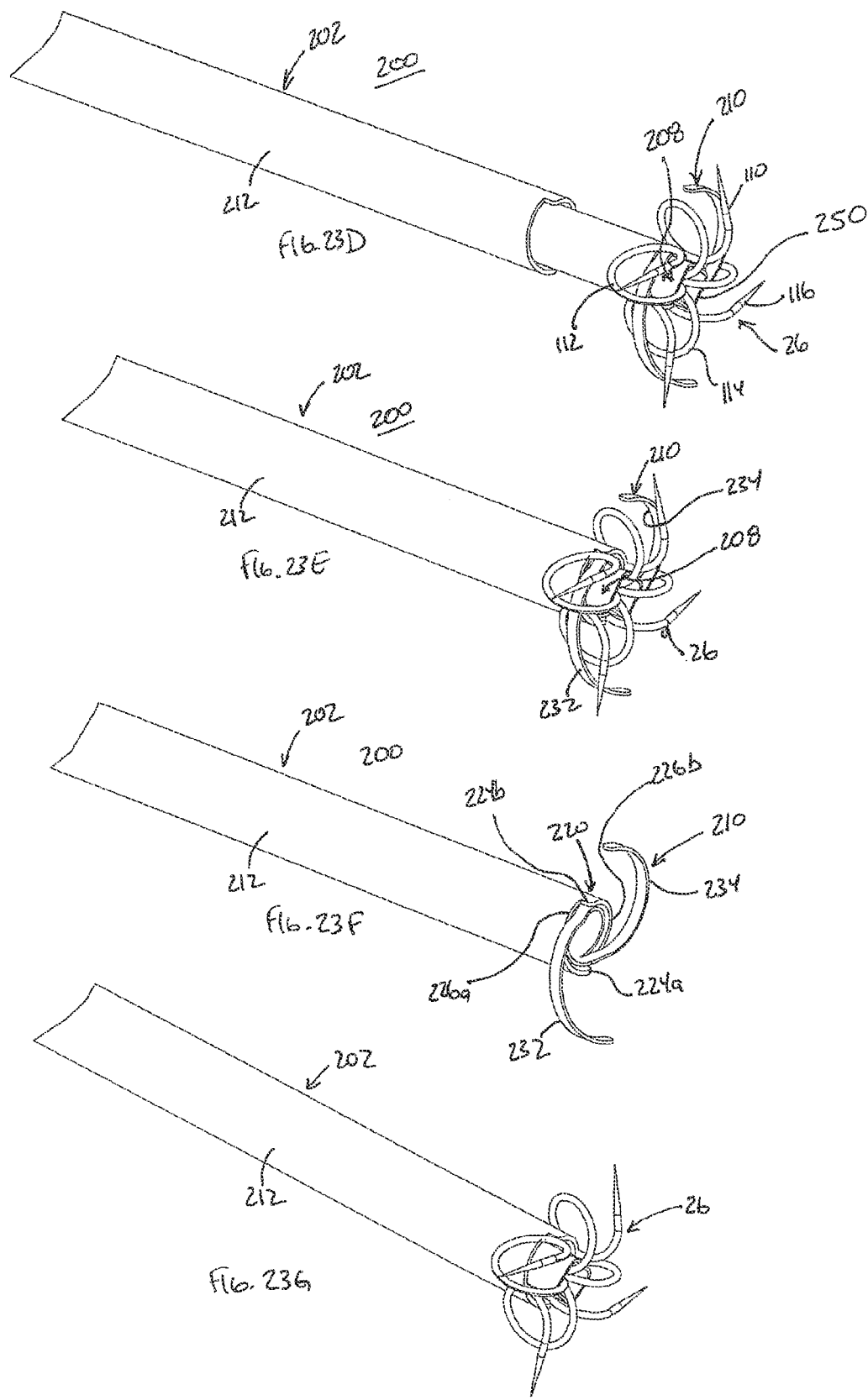

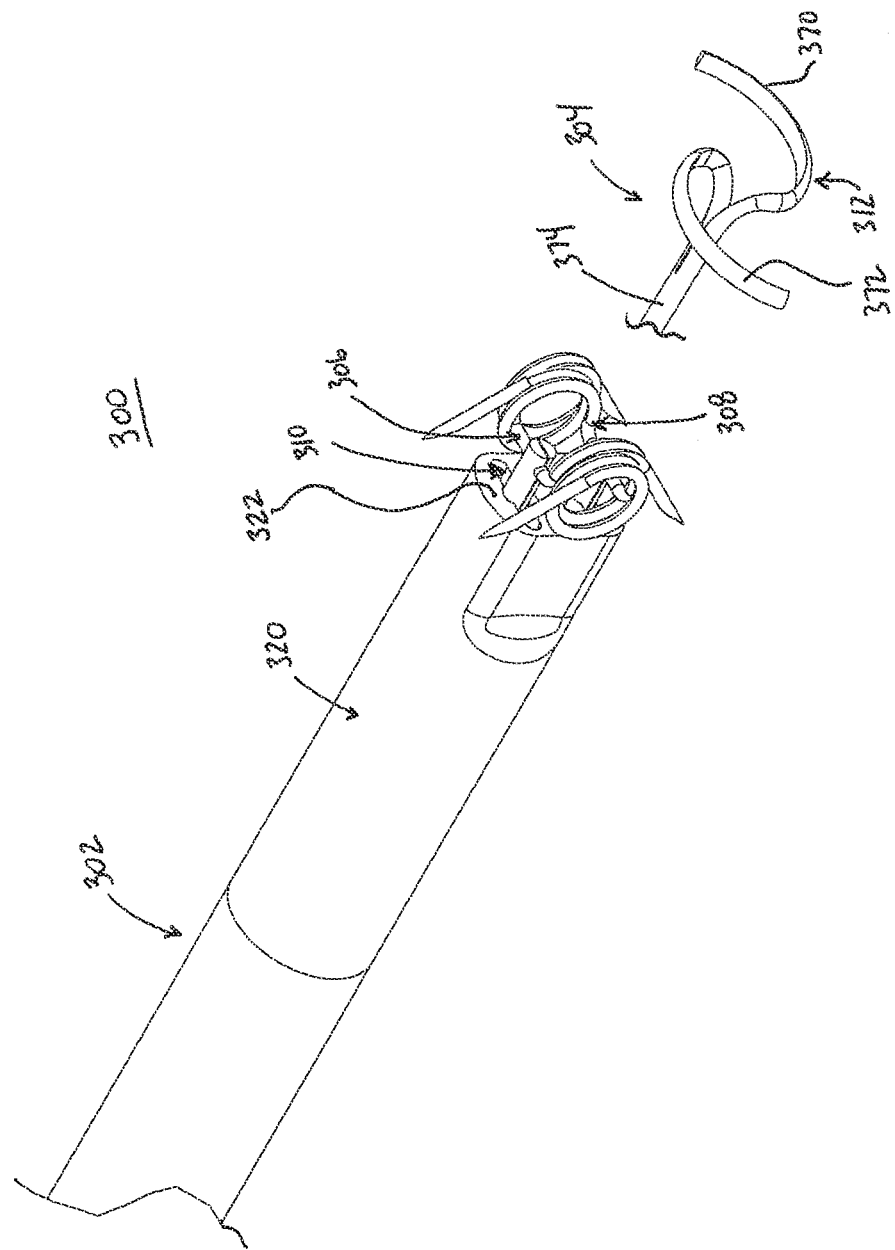

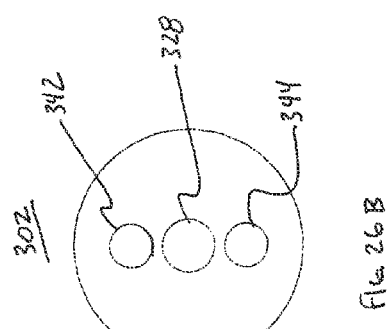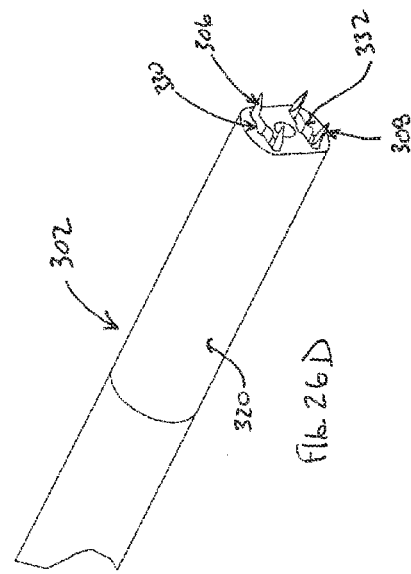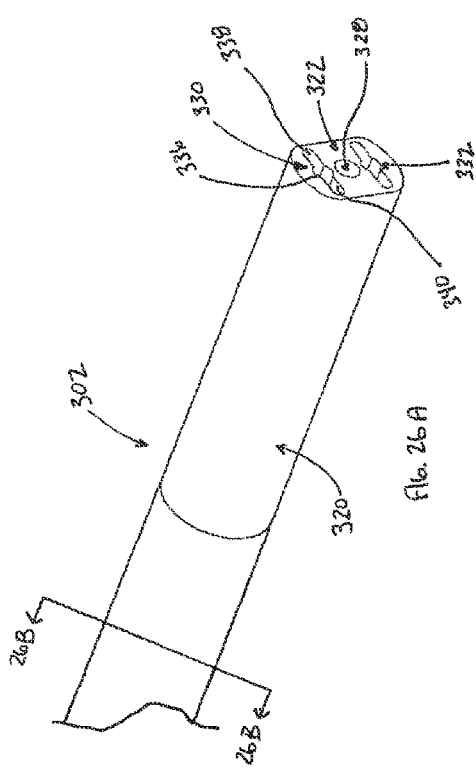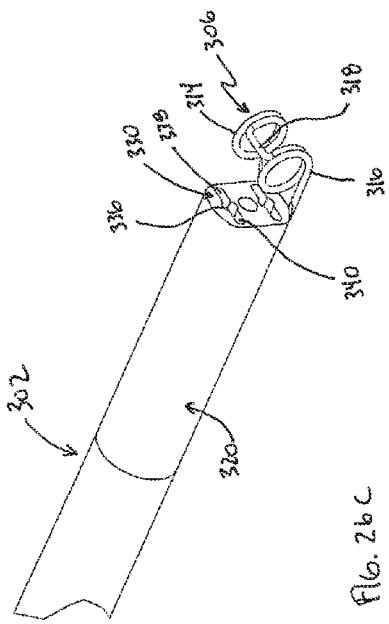

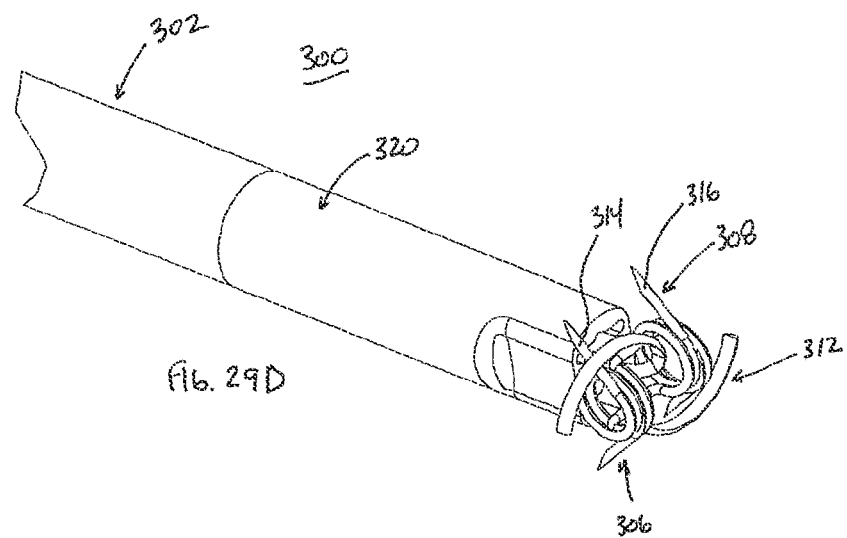
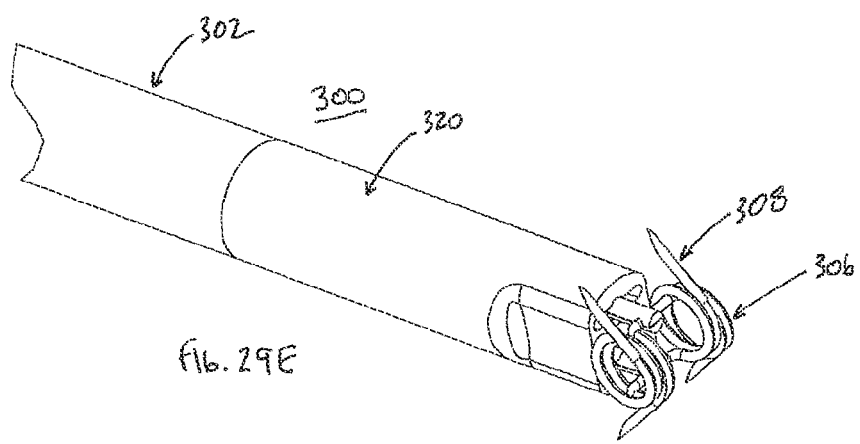
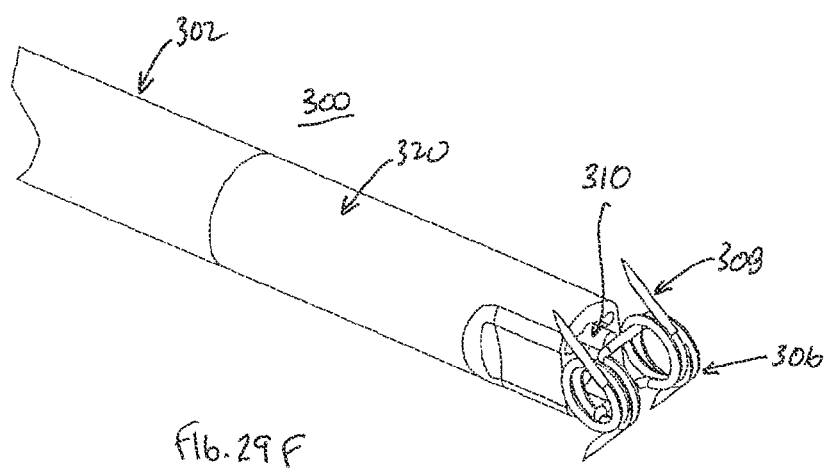

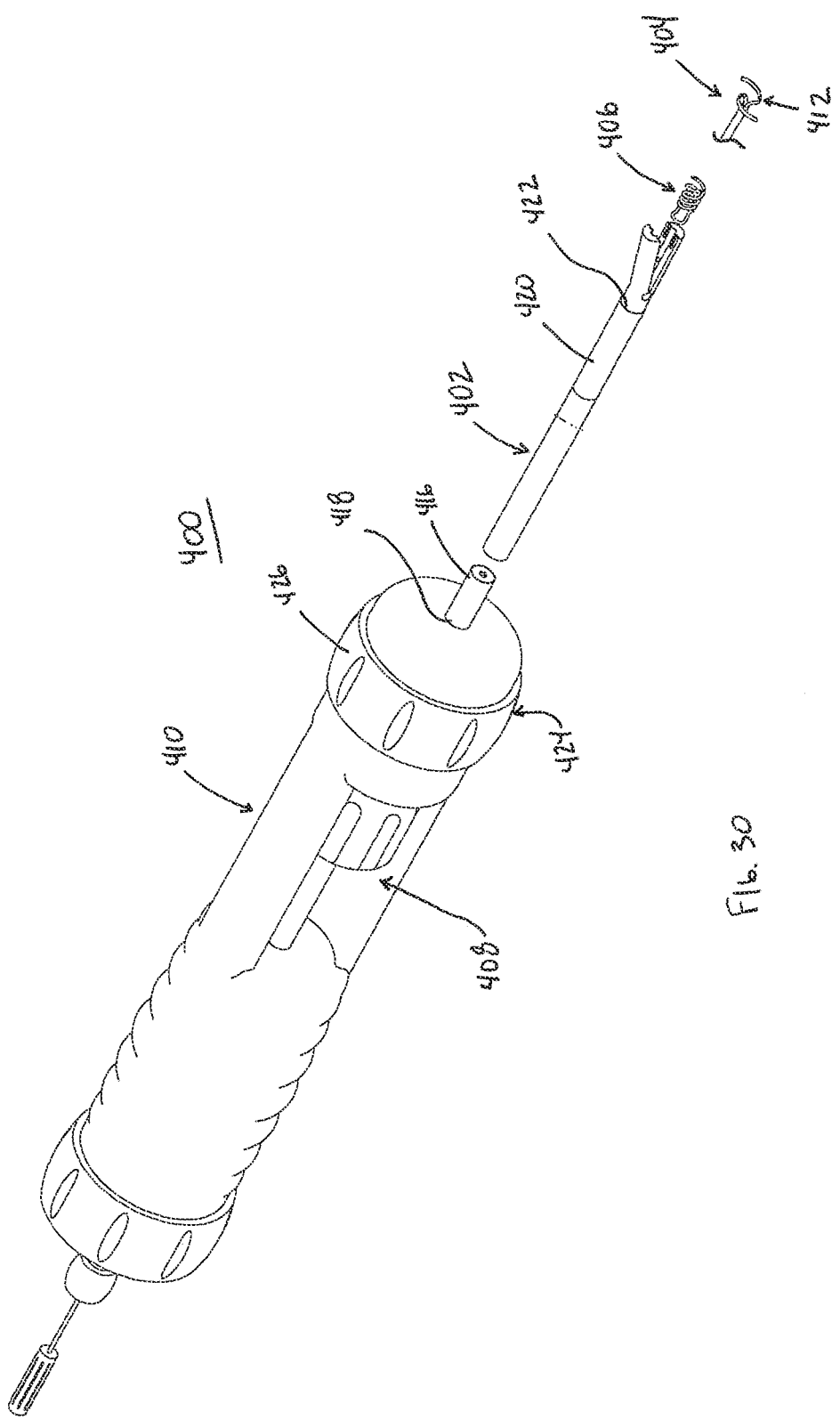

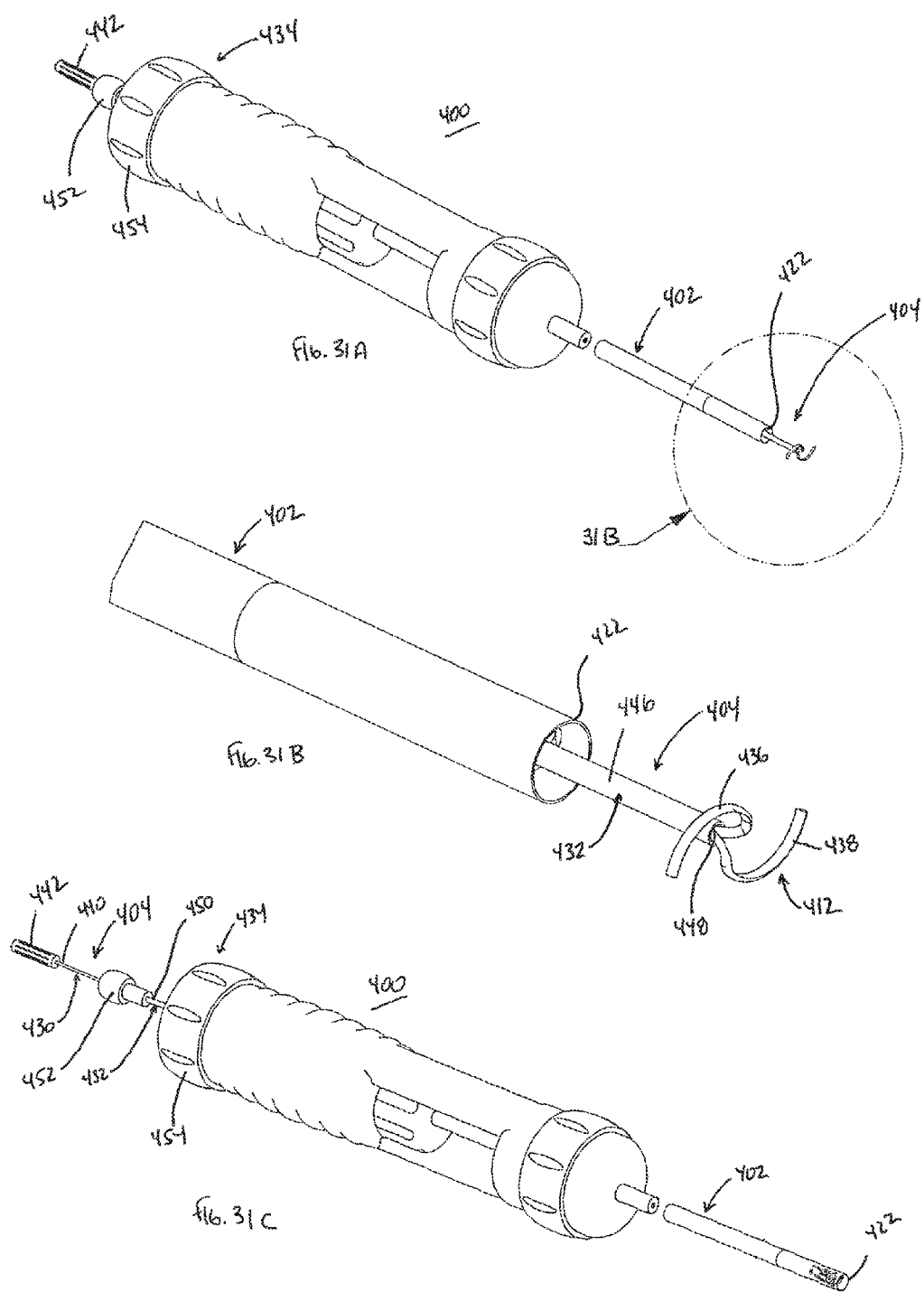

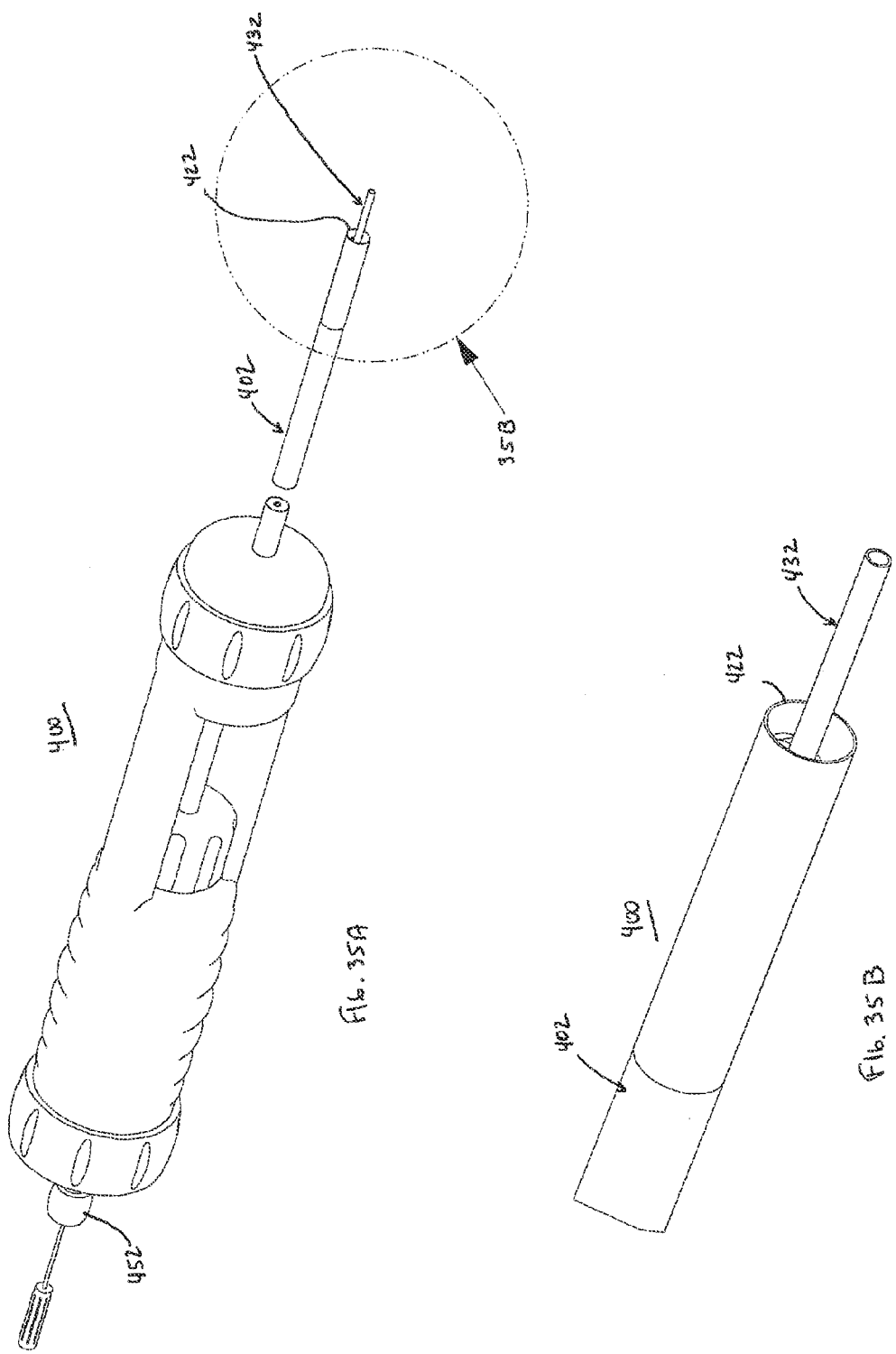

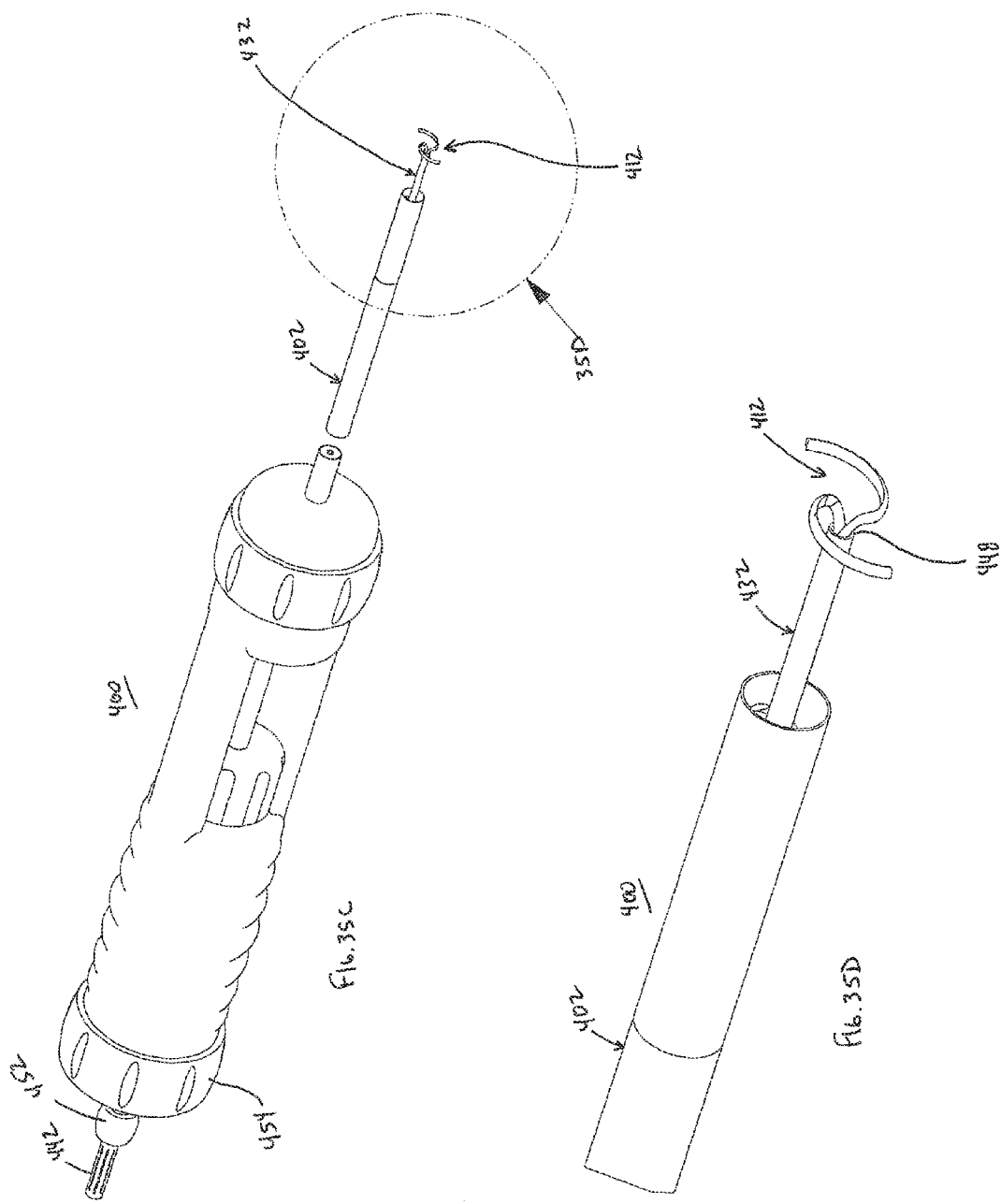

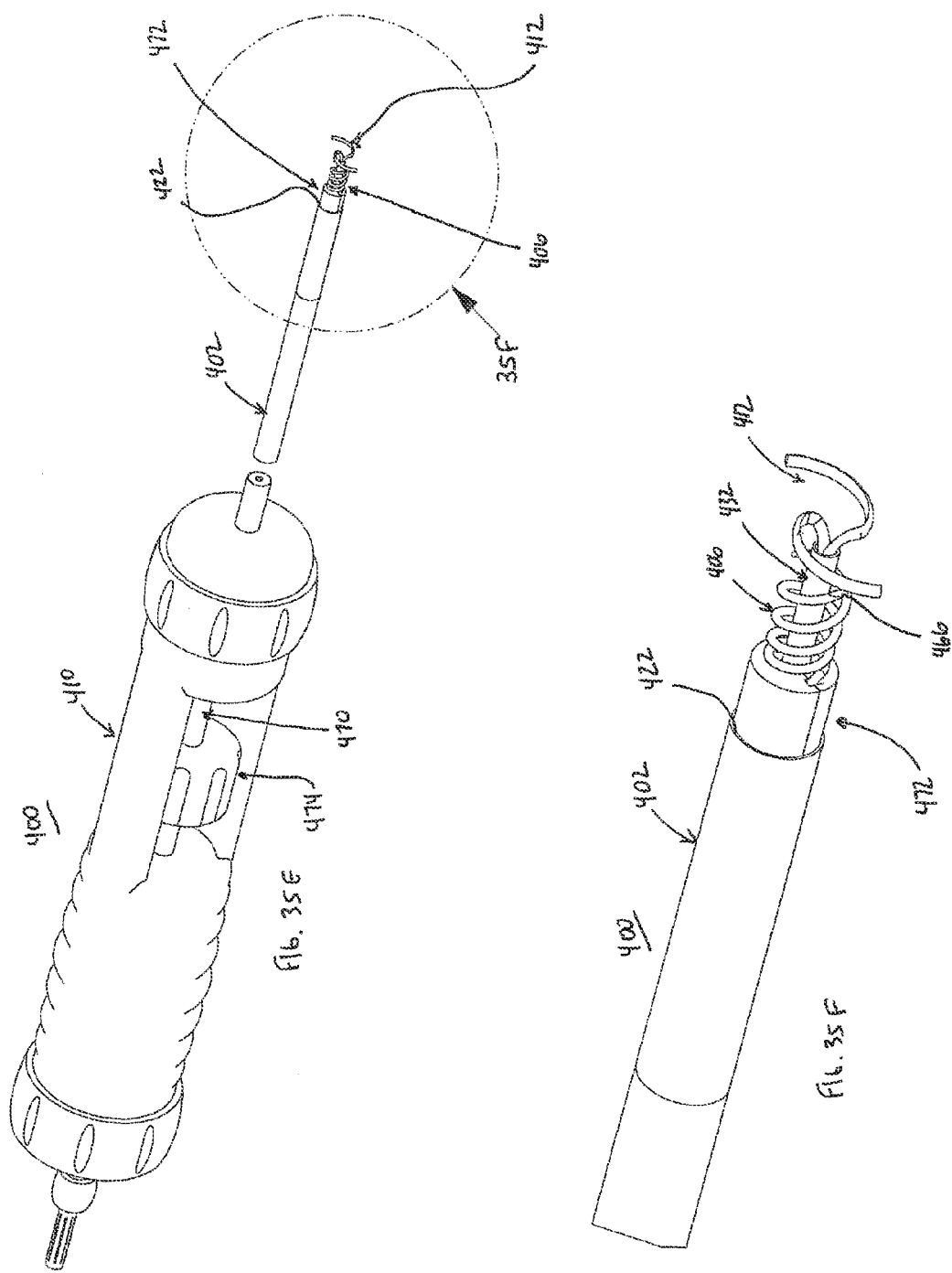

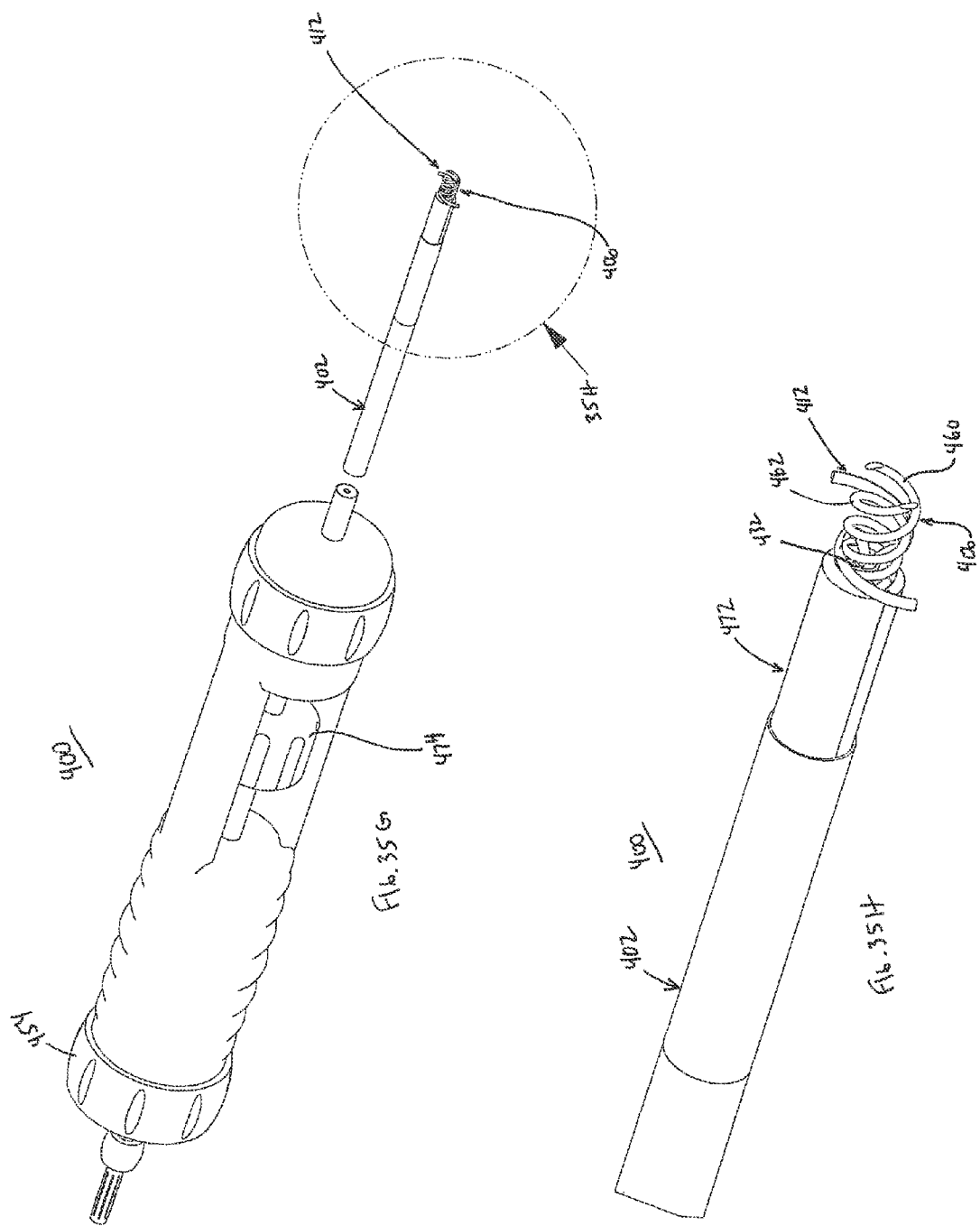

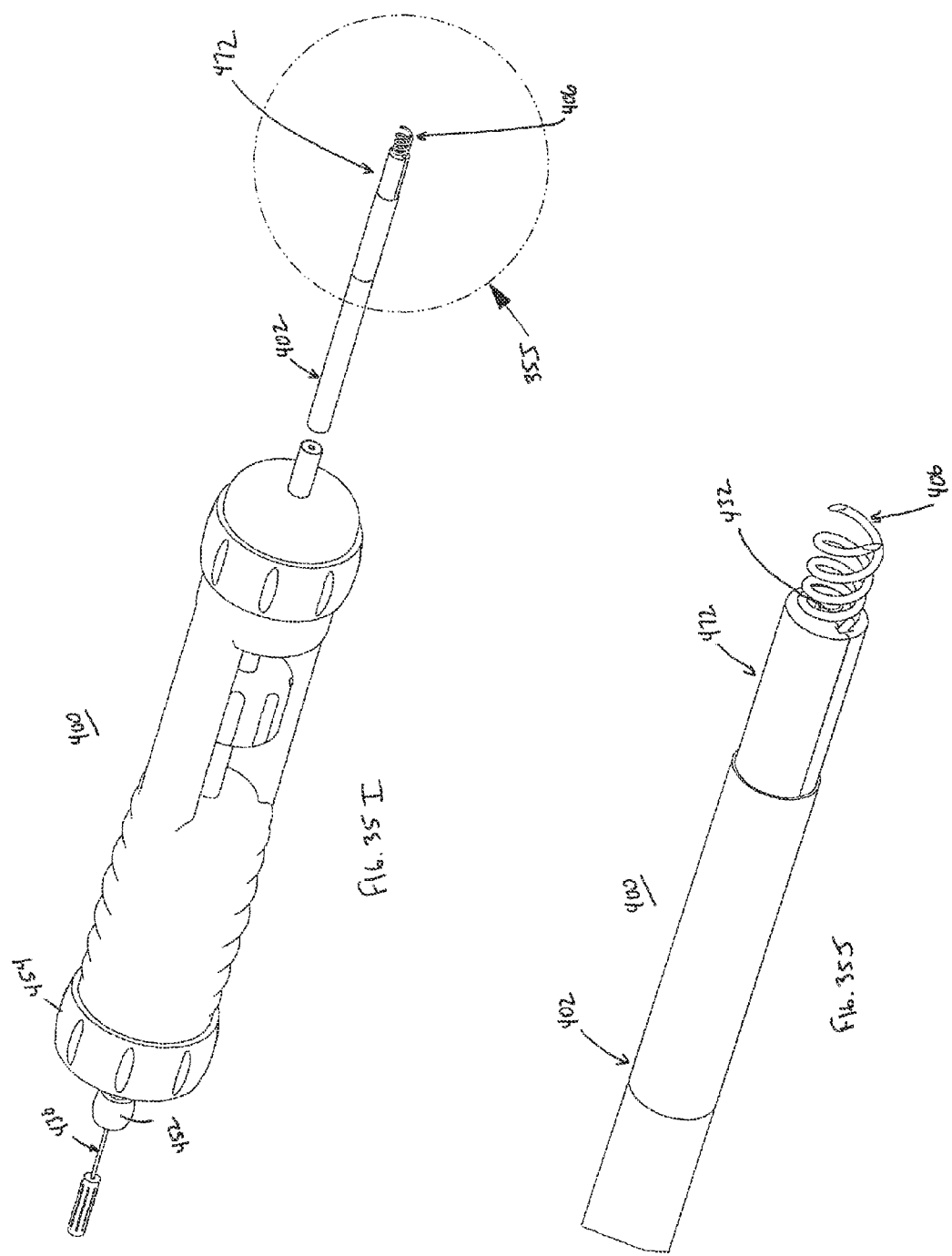

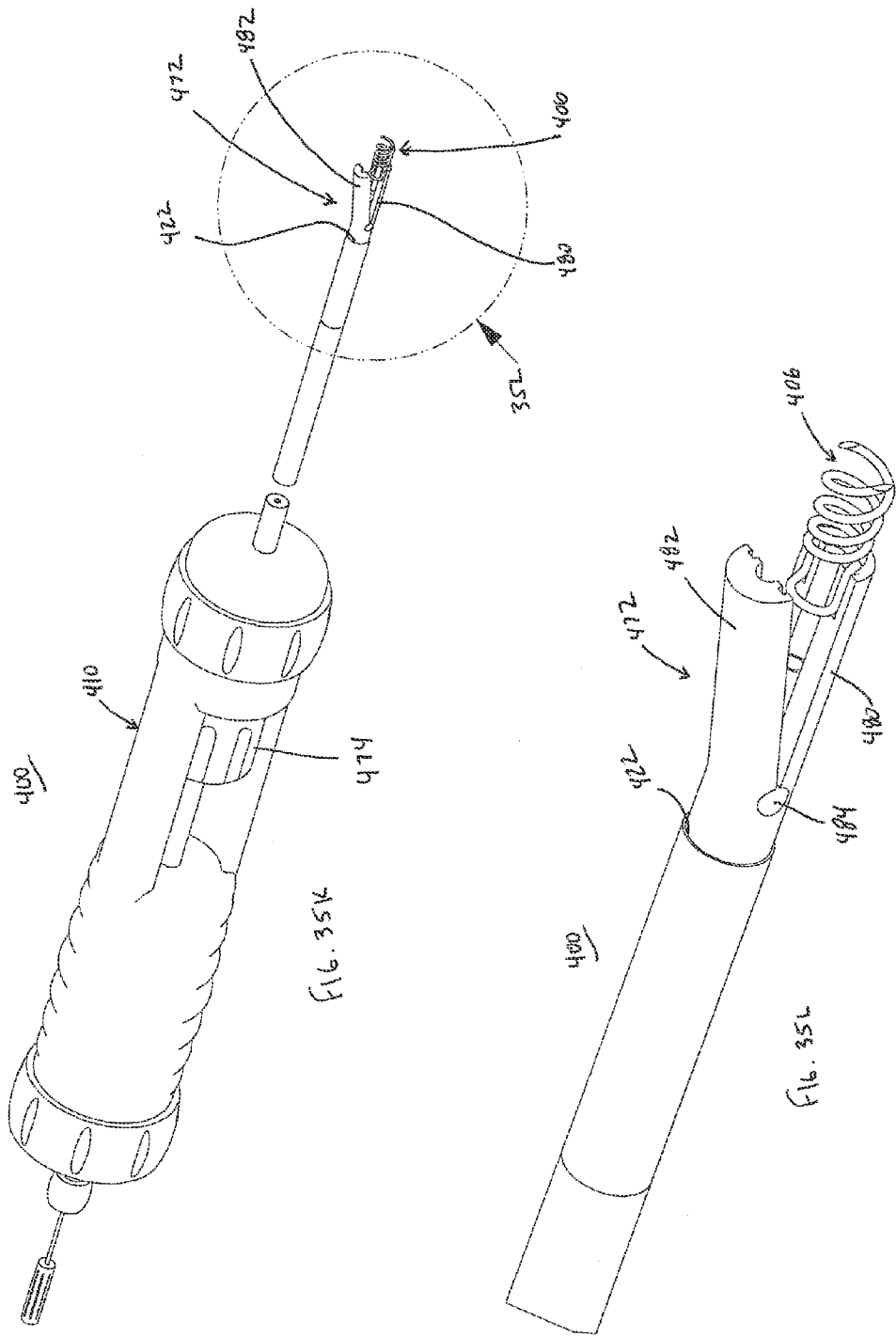

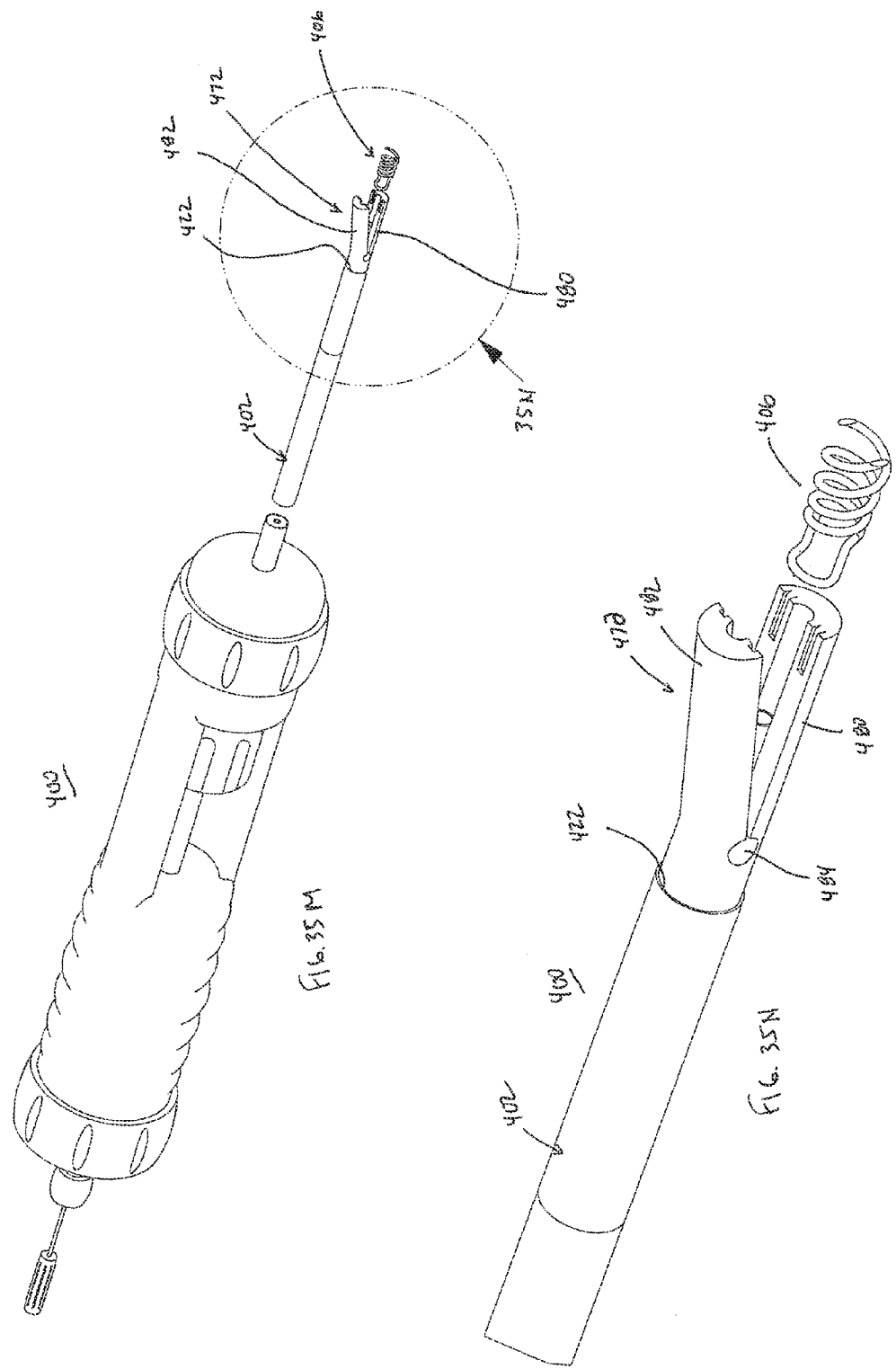

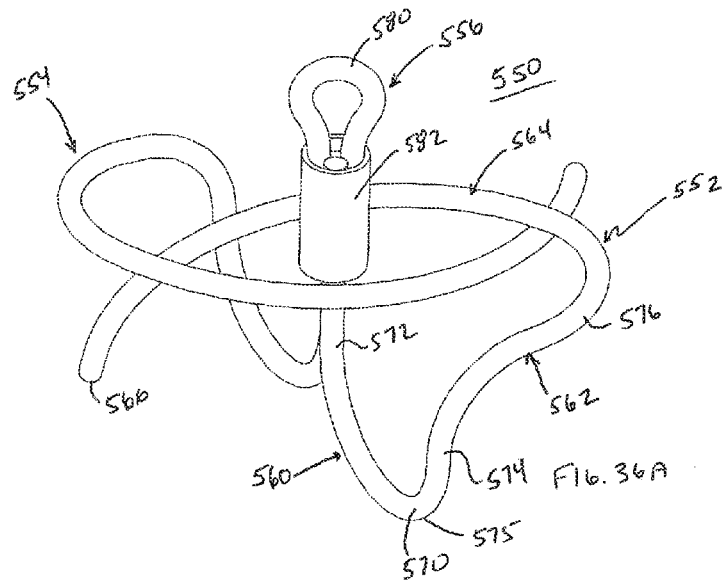
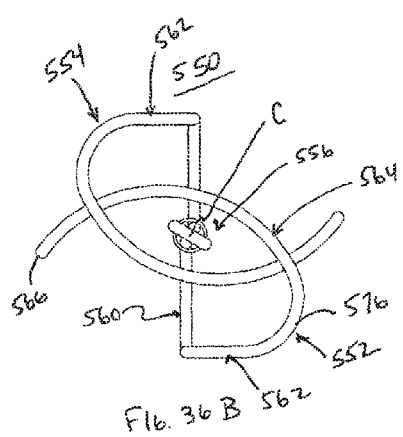
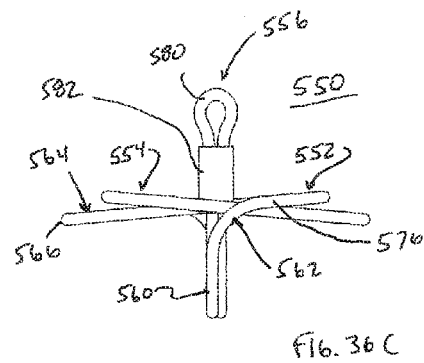
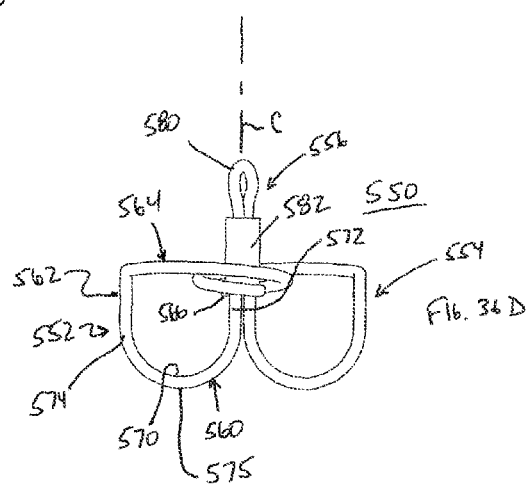

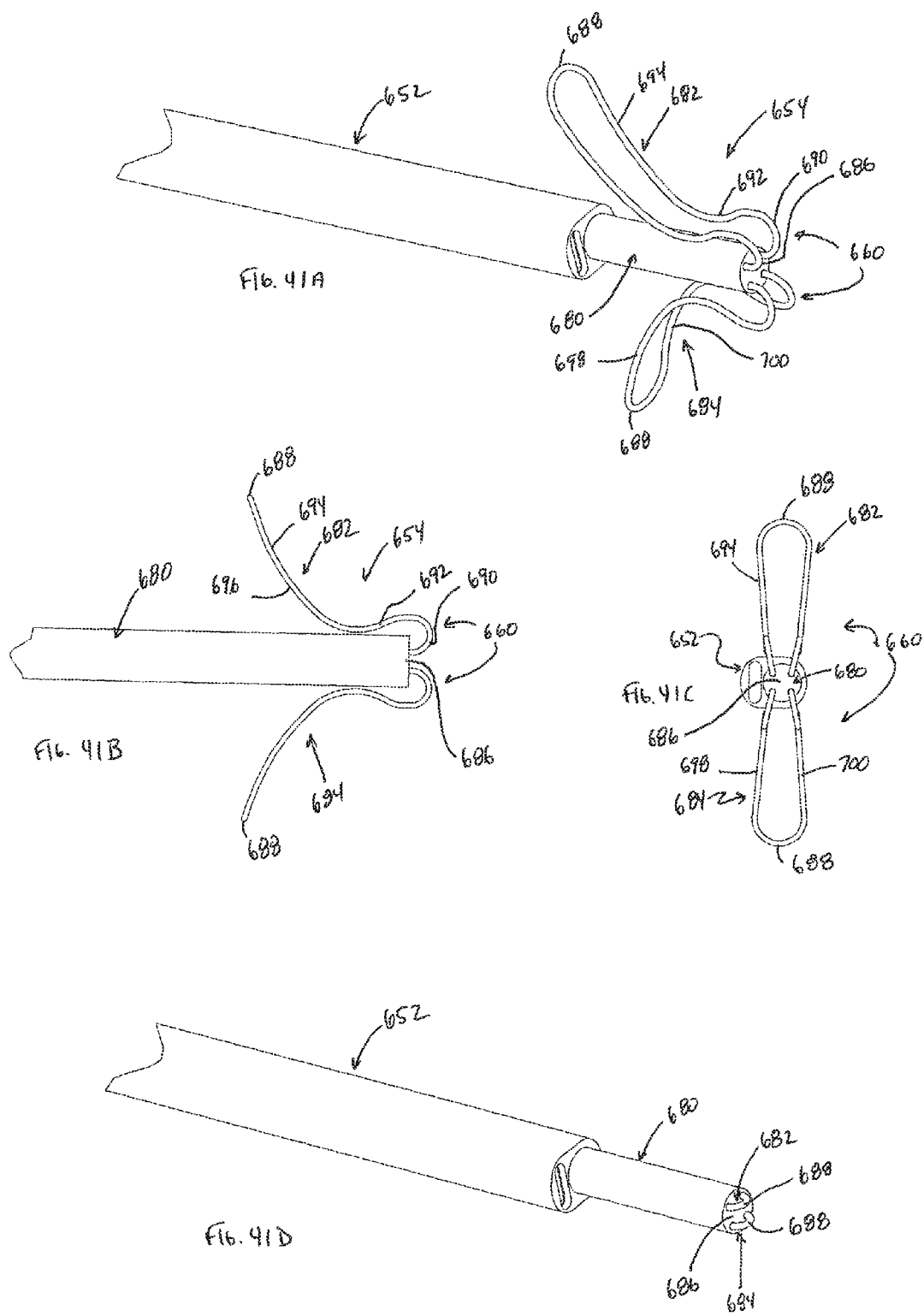

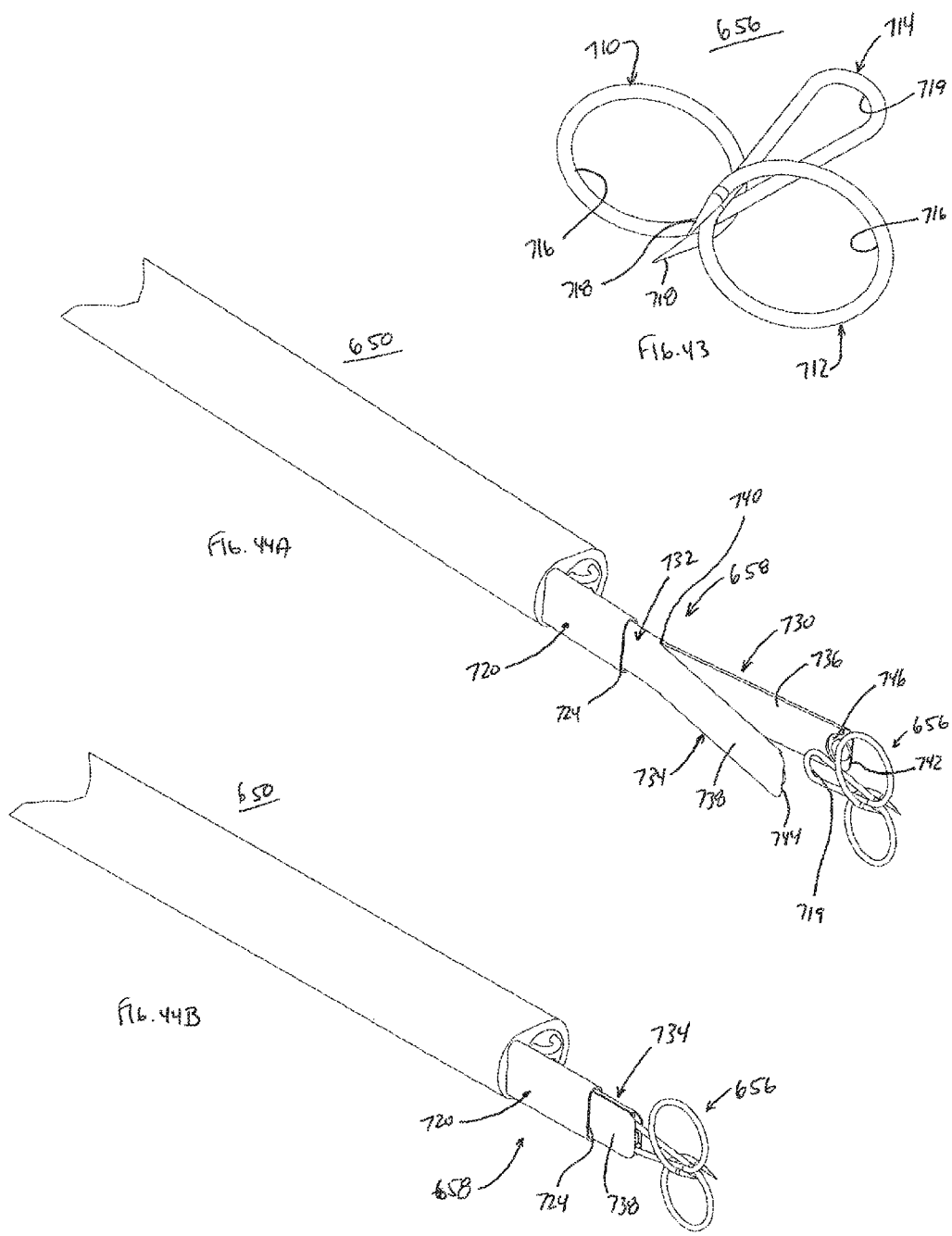

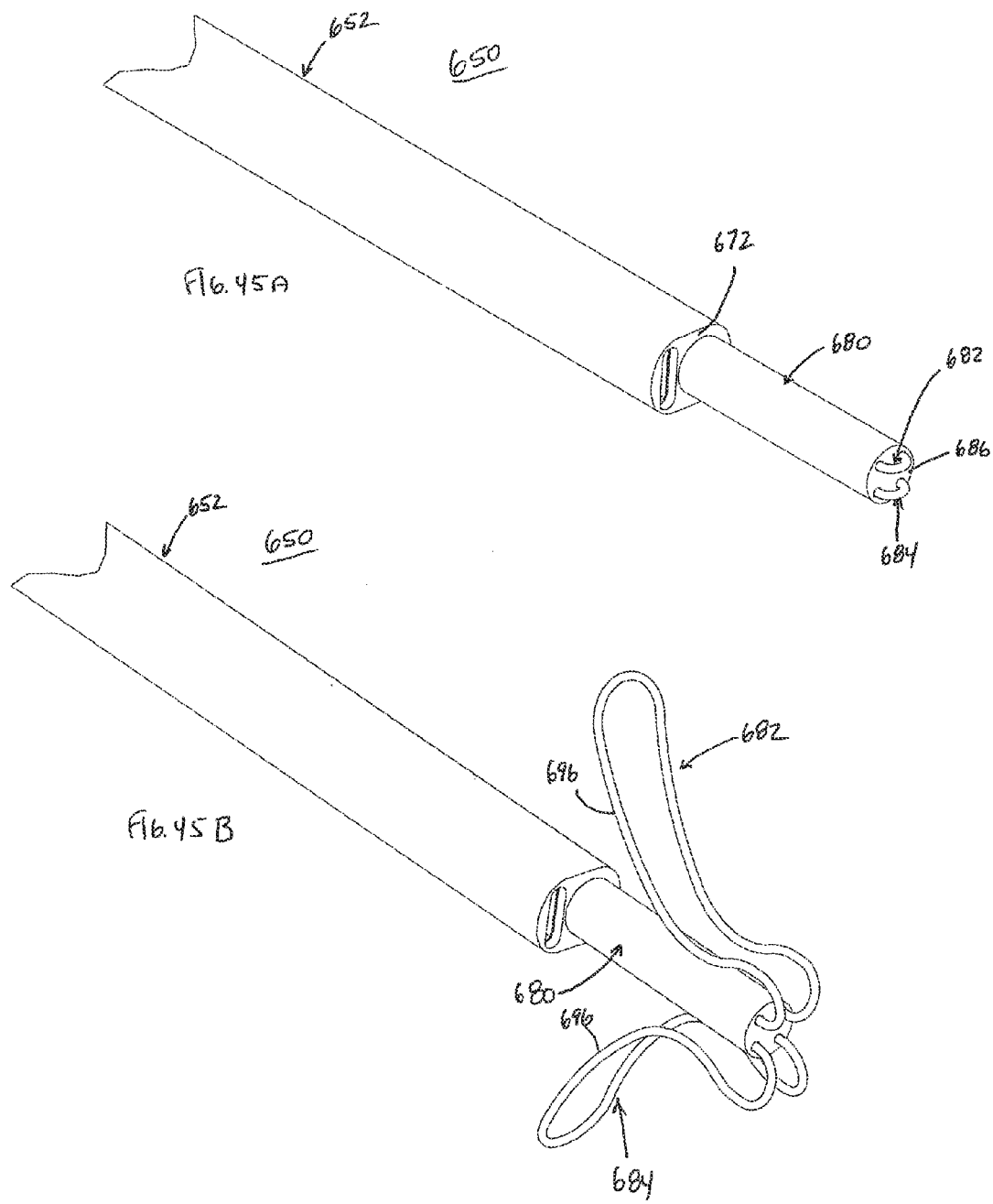

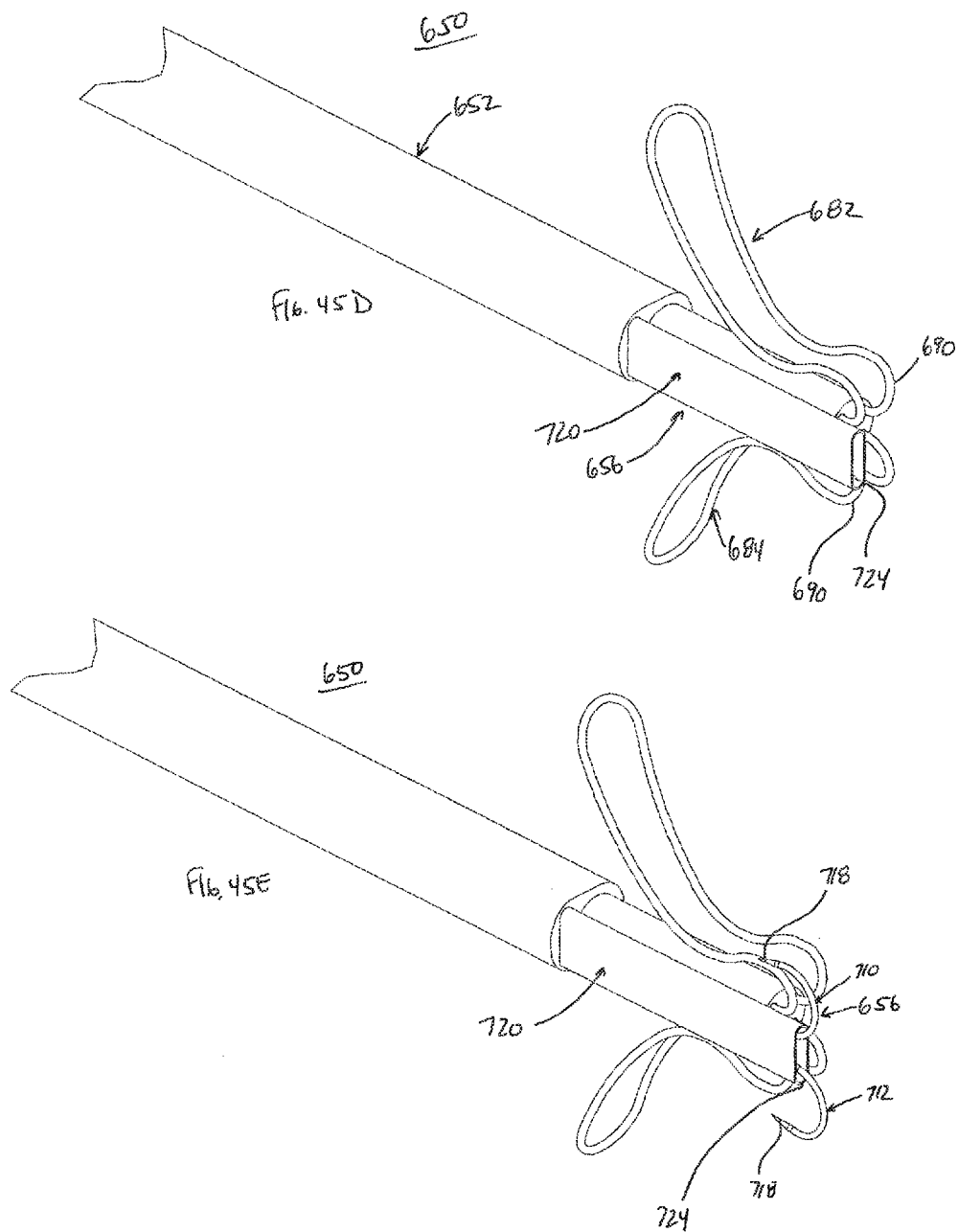

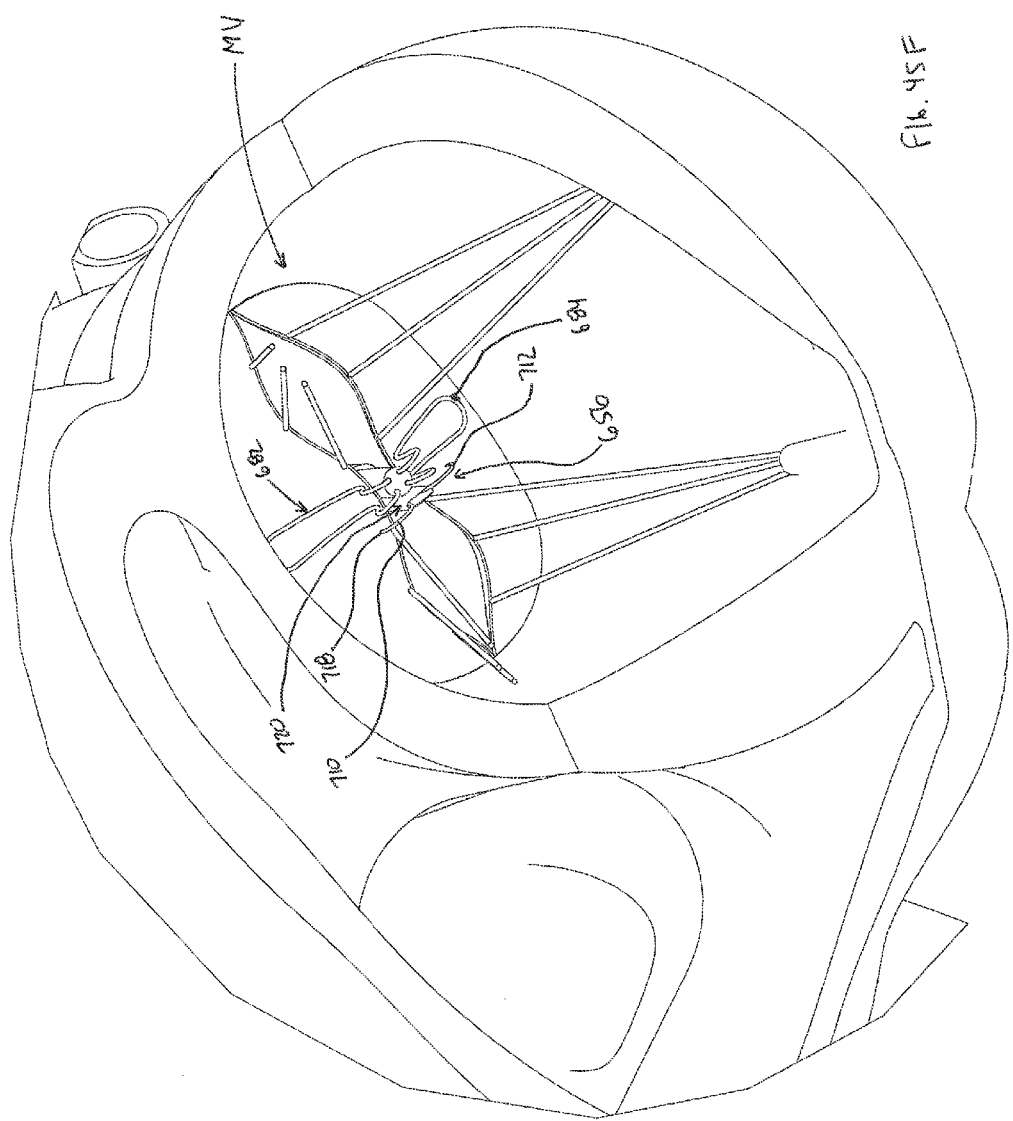

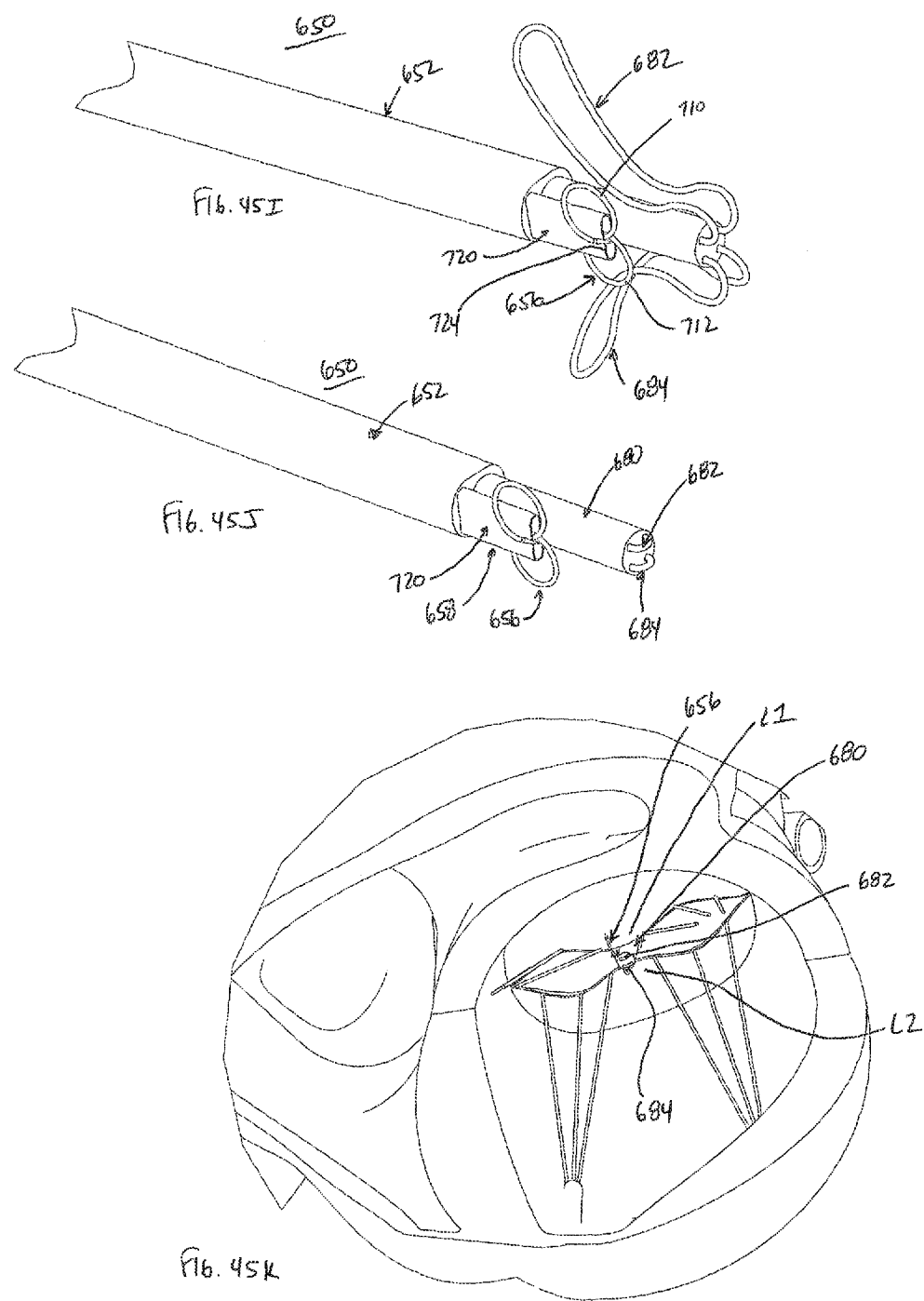

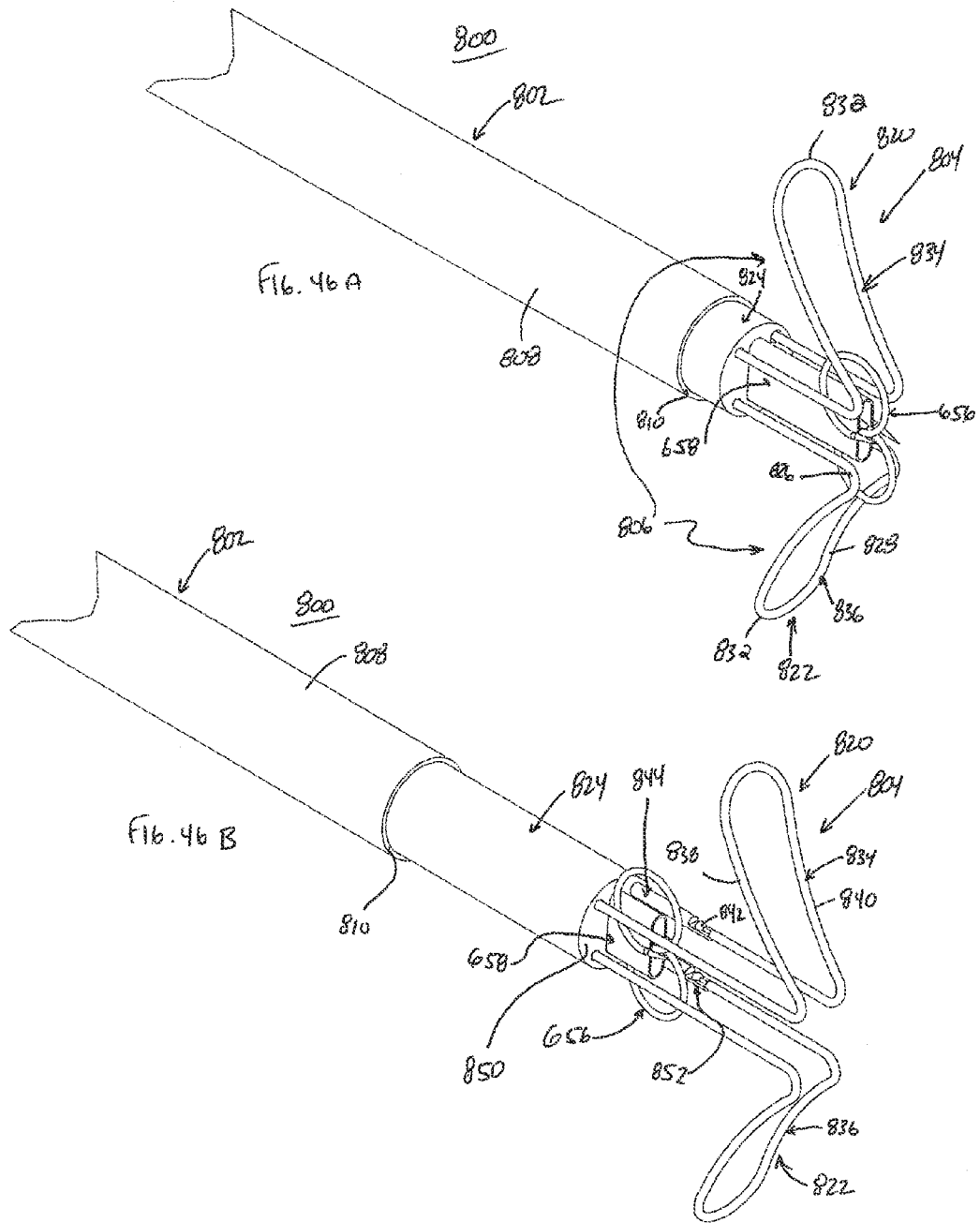

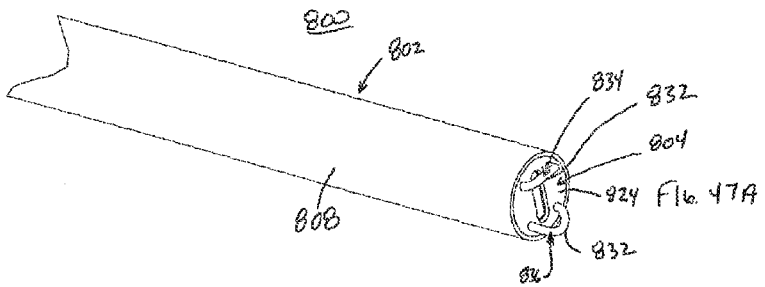
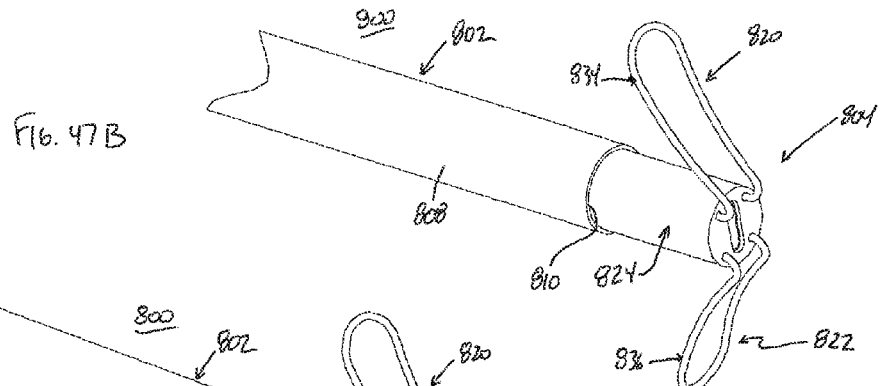
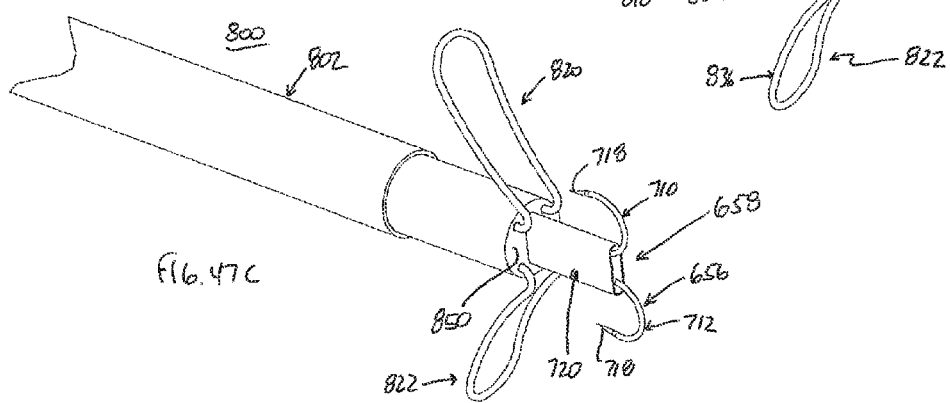
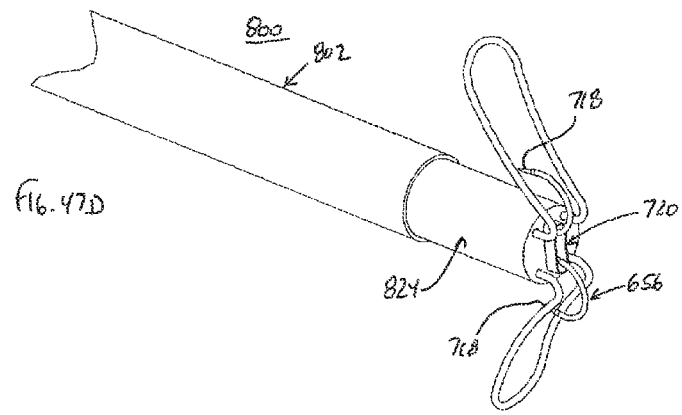

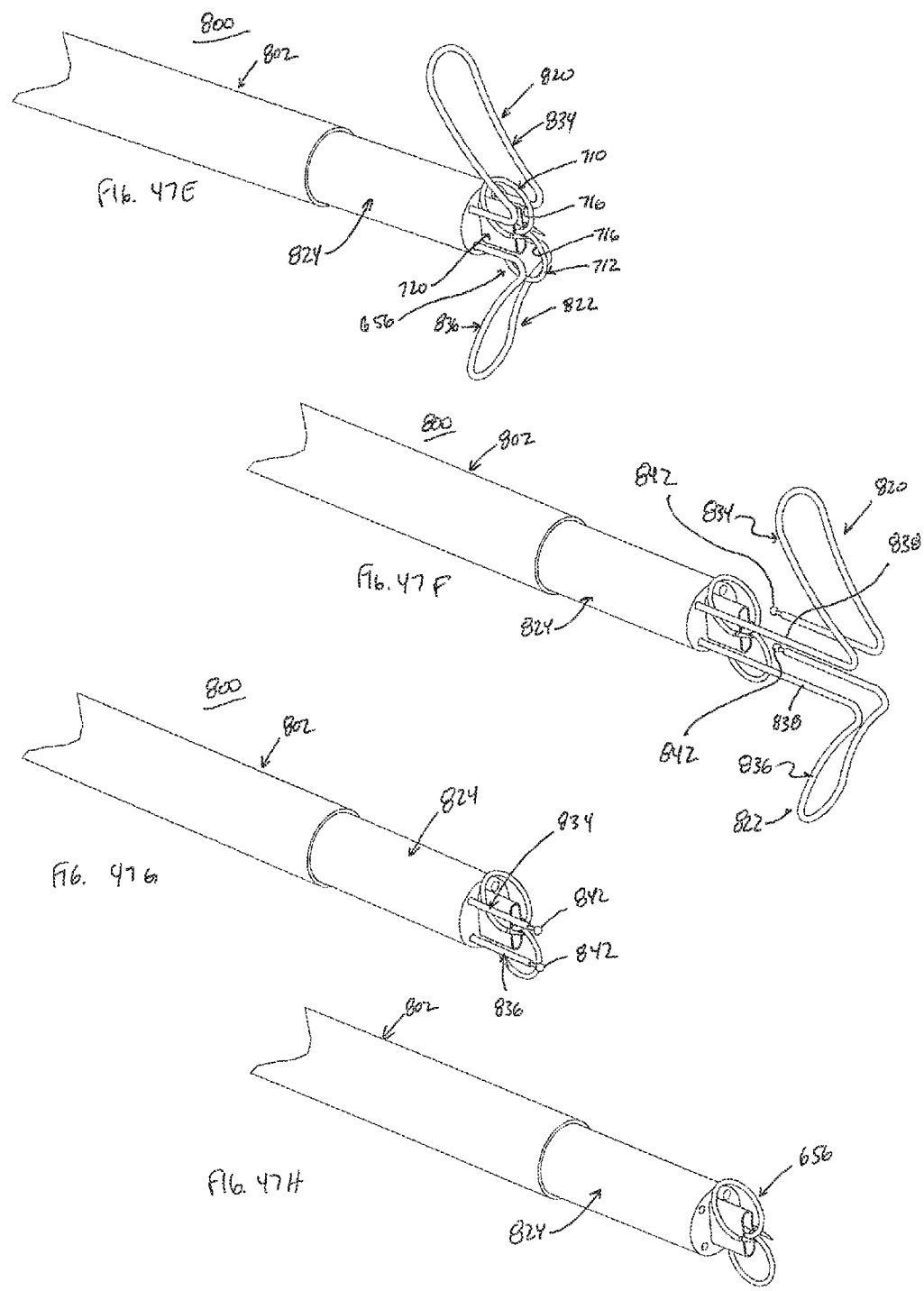

SYSTEM AND METHOD FOR PERCUTANEOUS MITRAL VALVE REPAIR

BACKGROUND

The present disclosure relates to systems and methods for repairing a heart valve. More particularly, it relates to minimally invasive, transcatheter-based systems and methods for repairing a cardiac valve, such as the mitral valve, via leaflet edge-to-edge attachment.

The heart is a four-chambered pump that moves blood efficiently through the vascular system. Blood enters the heart through the vena cava and flows into the right atrium. From the right atrium, blood flows through the tricuspid valve and into the right ventricle, which then contracts and forces blood through the pulmonic valve and into the lungs. Oxygenated blood returns from the lungs and enters the heart through the left atrium and passes through the mitral valve and into the left ventricle. The left ventricle contracts and pumps blood through the aortic valve, into the aorta, and to the vascular system.

The mitral valve consists of two leaflets (anterior and posterior) attached to a fibrous ring or annulus. The leaflets each form a free edge opposite the annulus. The free edges of the leaflets are secured to lower portions of the left ventricle through chordae tendineae (or "chordae") that include a plurality of branching tendons secured over the lower surfaces of each of the valve leaflets. The chordae are further attached to papillary muscles that extend upwardly from the lower portions of the left ventricle and interventricular septum.

In a healthy heart, the free edges of the mitral valve leaflets close against one another (or coapt) during contraction of the left ventricle to prevent blood from flowing back into the left atrium. However, due to cardiac disease, valve defects, or other reasons, the leaflets may be caused to remain partially spaced or open during ventricular contraction (e.g., leaflet prolapse) and thus allow regurgitation of blood into the left atrium. This results in reduced ejection volume from the left ventricle, causing the left ventricle to compensate with a larger stroke volume. Eventually, the increased work load results in dilation and hypertrophy of the left ventricle, enlarging and distorting the shape of the mitral valve. Mitral valve regurgitation in an increasingly common cardiac condition that can quickly lead to heart failure, dangerous arrhythmias, and other serious complications.

It is common medical practice to treat mitral valve regurgitation by either valve replacement or repair. Valve replacement conventionally entails an open-heart surgical procedure in which the patient's mitral valve is removed and replaced with an artificial valve. This is a complex, invasive surgical procedure with the potential for many complications and a long recovery.

Mitral valve repair includes a variety of procedures to repair or reshape the leaflets to improve closure of the valve during ventricular contraction. If the mitral valve annulus has become distended, a frequent repair procedure involves implanting an annuloplasty ring or band on the mitral valve annulus. Another approach for treating mitral valve regurgitation requires a flexible elongated device that is inserted into the coronary sinus and adapts to the shape of the coronary sinus. The device then undergoes a change that causes it to assume a reduced radius of curvature, and as a result, causes the radius of curvature of the coronary sinus and the circumference of the mitral annulus to be reduced. A more recent technique for mitral valve repair entails the suturing or fastening of segments of the opposed valve leaflets together, and is referred to as a "bow-tie" or "edge-to-edge" technique.

While all of these techniques can be very effective, they usually rely on open heart surgery where the patient's chest is opened, typically via sternotomy, and the patient placed on cardiopulmonary bypass. While some percutaneous or transcatheter mitral valve repair procedures have been contemplated premised upon the edge-to-edge technique, the confined nature of the native mitral valve anatomy renders capturing and securing of the leaflets exceedingly difficult.

In light of the above, a need exists for systems and methods for repairing a mitral valve using minimally invasive surgical techniques, for example in the treatment of mitral valve regurgitation.

SUMMARY

Some aspects of the present disclosure relate to a system for minimally invasive repair of a mitral valve. The system includes a delivery catheter, a capture body and a surgical fastener. The catheter terminates at a distal end. The capture body includes first and second legs extending from a center portion. The capture body is self-transitionable from a collapsed arrangement to a normal arrangement in which extension of the legs from the center portion defines a common wind direction. The surgical fastener includes a self-closing clip configured to self-transition from a deflected arrangement to an undeflected arrangement in which the clip forms a loop. With this in mind, the system is configured to provide a delivery state, a chordae capture state, and a release state. In the delivery state, the capture body and the surgical fastener are slidably disposed within the catheter and forced to the collapsed arrangement and the deflected arrangement, respectively. In the chordae capture state, the capture body legs are distal the distal end and self-assume the normal arrangement for capturing chordae connected to a mitral valve. In the release state, the surgical fastener is released from the distal end of the catheter and the clip self-transitions toward the undeflected arrangement for securing edges of opposing mitral valve leaflets.

Other aspects of the present disclosure relate to methods of repairing a mitral valve of a heart. The mitral valve includes opposing leaflets extending from an annulus to define opposing free edges, with the leaflets being secured to a left ventricle of the heart by chordae. The method includes receiving the repair system described above in the delivery state. The distal end of the delivery catheter is advanced proximate the mitral valve. The capture body legs are deployed from the distal end such that the capture body self-transitions toward the normal arrangement. The capture body is rotated to engage chordae of the opposing leaflets between the legs and the center portion, including the engaged chordae and corresponding leaflets being drawn toward one another. Finally, the surgical fastener is released from the distal end such that the clip passes through tissue of at least one of the opposing leaflets and the surgical fastener connects the opposing free edges.

BRIEF DESCRIPTION OF THE DRAWINGS

FIG. 3A is a perspective view of a capture body component of the system of FIG. 1, in a normal arrangement;

FIG. 3B is a top plan view of the capture body of FIG. 3A;

FIG. 8A is an enlarged perspective view of a distal region of the system of FIG. 1 with portions removed an in a partial clip deployment state;

FIG. 8B is a cross-sectional view of the distal region of FIG. 8A;

FIG. 9A is an enlarged perspective view of a distal region of the system of FIG. 1 with portions removed and in a full clip deployment state;

FIG. 9B is a cross-sectional view of the distal region of FIG. 9A;

FIGS. 13A-18B illustrate use of the system of FIG. 1 in percutaneously repairing a defective mitral valve in accordance with principles of the present disclosure;

FIG. 20 is a perspective, partially exploded view of another transcatheter mitral valve repair system in accordance with principles of the present disclosure;

FIGS. 23A-23G illustrate use of the system of FIG. 20 in percutaneously repairing a defective mitral valve in accordance with principles of the present disclosure;

FIG. 24 is a perspective, partially exploded view of a portion of another transcatheter mitral valve repair system in accordance with principles of the present disclosure;

FIG. 26A is a perspective view of a delivery catheter component of the system of FIG. 24;

FIG. 26B is a cross-sectional view of the catheter of FIG. 26A along the line 26B-26B;

FIGS. 26C and 26D illustrate loading of the surgical fasteners of FIG. 25 to the delivery catheter of FIG. 26A;

FIGS. 29A-29F illustrate use of the system of FIG. 24 in percutaneously repairing a defective mitral valve in accordance with principles of the present disclosure;

FIG. 30 is a perspective, partially exploded view of another transcatheter mitral valve repair system in accordance with principles of the present disclosure;

FIG. 31A is a perspective view of the system of FIG. 30 and illustrating portions of a capture assembly thereof;

FIG. 31B is an enlarged view of a distal portion of the system of FIG. 31A along section line 31B;

FIG. 31C is a perspective view of the system of FIG. 31A in illustrating the capture assembly in a retracted state;

FIGS. 35A-35N illustrate use of the system of FIG. 30 in percutaneously repairing a defective mitral valve in accordance with principles of the present disclosure;

FIG. 36A is an enlarged, perspective view of another embodiment surgical fastener useful with systems of the present disclosure;

FIG. 36B is a top plan view of the surgical fastener of FIG. 36A;

FIG. 36C is a side view of the surgical fastener of FIG. 36A;

FIG. 36D is an end view of the surgical fastener of FIG. 36A;

FIG. 41A is a perspective view of a portion of the system of FIG. 39 and illustrating a capture assembly component in a deployed state;

FIG. 41B is a side view of the system of FIG. 41A;

FIG. 41C is an end view of the system of FIG. 41A;

FIG. 41D is a perspective view of the system of FIG. 41A, illustrating a capture body component in a retracted state;

FIG. 43 is an enlarged, perspective view of a surgical fastener useful with the system of FIG. 39;

FIG. 44A is a perspective view of the system of FIG. 39, illustrating a fastener delivery assembly component thereof and including an engagement device in an open state;

FIG. 44B is a perspective view of the system of FIG. 44A, including the engagement device in a closed state in retaining a surgical fastener;

FIGS. 45A-45K illustrate use of the system of FIG. 39 in percutaneously repairing a defective mitral valve in accordance with principles of the present disclosure;

FIG. 46A is a perspective view of a portion of another transcatheter mitral valve repair system in accordance with principles of the present disclosure;

FIG. 46B is a perspective view of the system of FIG. 46A and illustrating portions of a capture assembly component thereof arranged for removal of capture body; and FIGS. 47A-47H illustrate use of the system of FIG. 46A in percutaneously repairing a defective mitral valve in accordance with principles of the present disclosure.

DETAILED DESCRIPTION

Figure 1:
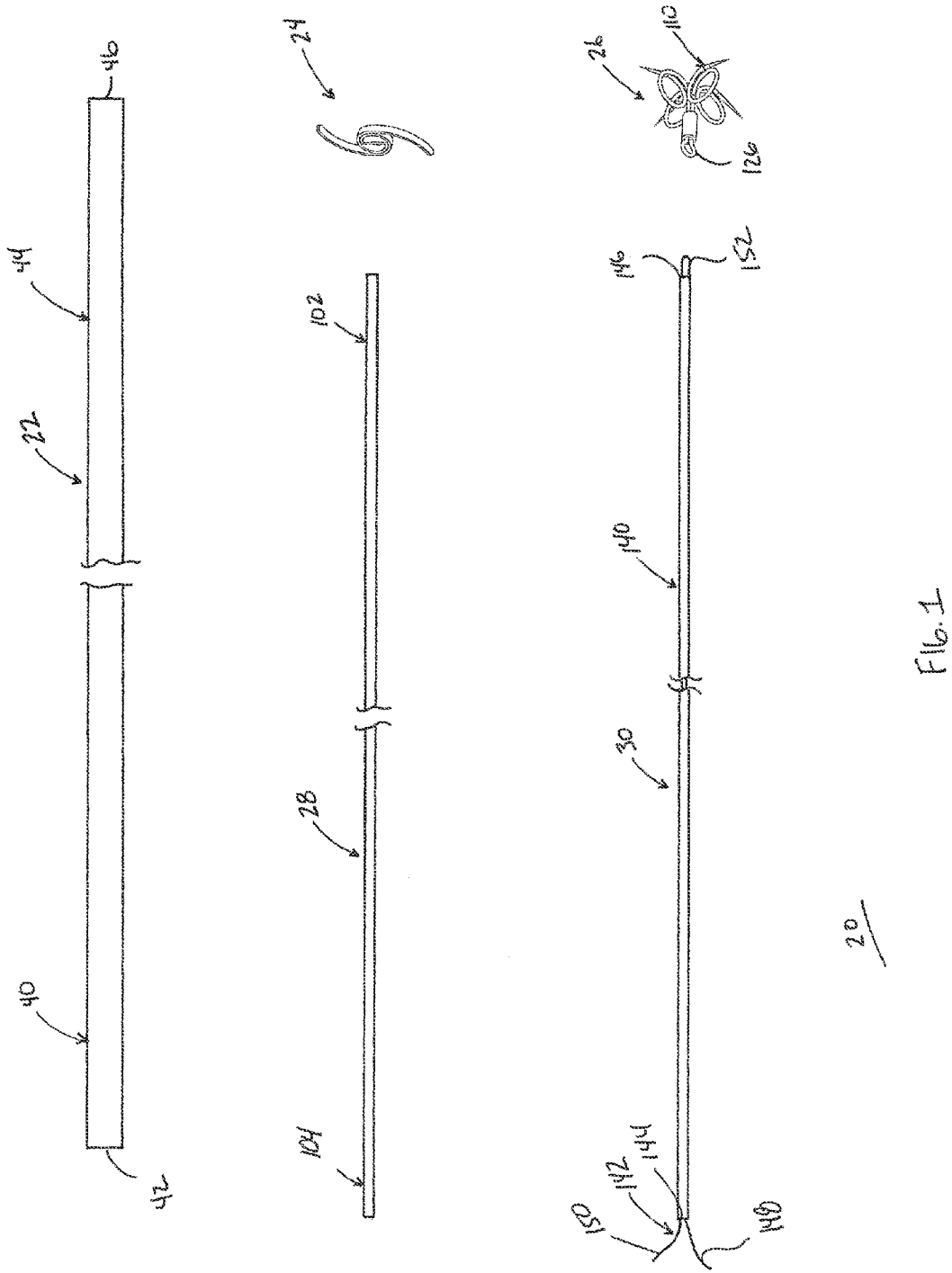
FIG. 1 is an exploded view of a transcatheter mitral valve repair system in accordance with principles of the present disclosure.

One embodiment of a system 20 for percutaneously repairing a mitral valve in accordance with principles of the present disclosure is shown in FIG. 1. The system 20 includes a delivery catheter 22, a capture body 24, a surgical fastener 26, a shaft 28, and a fastener delivery assembly 30. Details on the various components are provided below. In general terms, however, the delivery catheter 22 is sized to slidably receive the capture body 24 and the surgical fastener 26. In this regard, the capture body 24 is transitionable from the normal arrangement illustrated in FIG. 1 to a collapsed arrangement within the delivery catheter 22. Similarly, the surgical fastener 26 is transitionable from the undeflected arrangement shown in FIG. 1 to a deflected arrangement within the delivery catheter 22. The shaft 28 is connected to the capture body 24 and effectuates manipulation of the capture body 24 relative to the delivery catheter 22 (e.g., longitudinal and rotational movement). The fastener delivery assembly 30 is selectively connected to the surgical fastener 26, and effectuates manipulation of the surgical fastener 26 relative to the catheter 22. In a delivery state of the system 20, the capture body 24 and the surgical fastener 26 are retained within the catheter 22 for percutaneous delivery to a mitral valve target site. In a chordae capture state of the system 20, at least a portion of the capture body 24 is deployed from the delivery catheter 22, self-transitions to the normal arrangement shown, and can be manipulated via the shaft 28 to capture or engage chordae at a mitral valve target site. Finally, in a release state, the surgical fastener 26 is deployed from the catheter 22 and released from the fastener delivery assembly 30, self-reverting to the undeflected arrangement shown to capture or fasten opposing leaflets of the mitral valve target site to one another. Optionally, the system 20 can incorporate additional components, such as a handle assembly (not shown) configured to assist in user manipulation of the delivery catheter 22, the capture body 24, and/or the surgical fastener 26.

The delivery catheter 22 can assume a variety of forms conventionally employed for atraumatic traversal of a patient's vasculature, and generally defines a proximal section 40 terminating at a proximal end 42, and a distal section 44 terminating at a distal end 46. In some embodiments, the distal section 44 can be formed of a more rigid material as compared to a remainder of the catheter 22 to better force and maintain the capture body 24 and the surgical fastener 26 in the collapsed state and the deflected state, respectively. For example, the distal section 44 can be formed of stainless steel or other metal, and a remainder of the catheter 22 is formed of a more flexible material, such as a polymeric braided tube. Alternatively, the catheter 22 can be a homogenous body.

Figure 2:
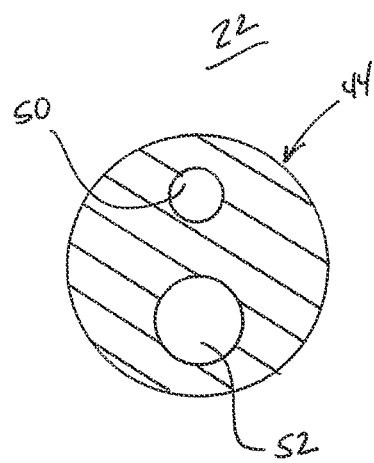
FIG. 2 is a cross-sectional view of a delivery catheter component of the system of FIG. 1.

With additional reference to FIG. 2, the catheter 22 forms first and second lumens 50, 52 extending through and between the proximal and distal sections 40, 44. In some constructions, both of the lumens 50, 52 are open at the distal end 46. The first lumen 50 is sized to slidably receive the capture body 24 and the shaft 28. The second lumen 52 is sized to slidably receive the surgical fastener 26 and the fastener delivery device 30. The lumens 50, 52 can be lined with a rigid material so that the capture body 24 and the surgical fastener 26 can slide relative thereto with minimal resistance, and the catheter 22 is less likely to deform proximate the distal end 46. Though not shown, the catheter 22 can form one or more additional lumens, for example a lumen that slidably receives a guide wire (not shown). Further, systems in accordance with principles of the present disclosure can incorporate one or more additional mechanisms within the delivery catheter 22, such as a steering mechanism (e.g., one or more pull wires) that permit user control or guidance of the distal section 44.

Returning to FIG. 1, the capture body 24 is formed of a robust shape memory material (e.g., Nitinol) so as to be deflectable or collapsible from the normal arrangement of FIG. 1 to a collapsed arrangement, and self-revert from the collapsed arrangement back or toward the normal arrangement. As best shown in FIGS. 3A and 3B, in at least the normal arrangement, the capture body 24 includes or defines a center portion 60, a first leg or prong 62, and a second leg or prong 64. In the normal arrangement, the center portion 60 has a perimeter 66 defining a circular or circle-like shape. The legs 62, 64 project outwardly relative to the perimeter 66, with the first leg 62 terminating at a tip 68, and the second leg 64 terminating at a tip 70. In this regard, the legs 62, 64 extend in or with an identical wind direction, such that the capture body 24 has, in some embodiments, a hurricane-like or spiral shape, as best reflected by the top plan view of FIG. 3B.

The wind direction associated with each of the legs 62, 64 is either clockwise or counterclockwise relative to the circle-like shape of the perimeter 66. The perimeter 66 may or may not be continuous, and may or may not reflect a true circle; relative to a two-dimensional top or bottom plan view, however, the perimeter 66 of the center portion 60 establishes a basis from which clock-type directional attributes (e.g., wind direction) can be identified. For example, the first leg 62 extends from the perimeter 66 at a point of departure 72, terminating at the tip 68. The point of departure 72 can be defined as a point along the leg 62 at which a lateral spacing between the leg 62 and the perimeter 66 begins to increase. By way of clarification, the point of departure 72 is at approximately a twelve o'clock position of the perimeter 66 relative to the orientation of FIG. 3B. With these conventions in mind, FIG. 3B depicts the first leg 62 as establishing a wind direction (represented by the arrow of "A") that is clockwise.

Extension of the second leg 64 relative to the perimeter 66 from a point of departure 74 similarly defines the same clockwise wind direction A. Alternatively, the wind direction established by both of the legs 62, 64 can be counterclockwise.

In some constructions, the legs 62, 64 can have an identical construction/dimension. Thus, the legs 62, 64 can define an identical curvature in extension from the perimeter 66. Alternatively, the legs 62, 64 can have differing dimension and/or curvatures. Similarly, one or both of the legs 62, 64 can have a linear segment or be entirely linear (e.g., extend tangentially from the perimeter 66). Regardless, the wind direction A of the legs 62, 64 is identical.

The legs 62, 64 are, in some embodiments, positioned opposite one another relative to the perimeter 66. Thus, the point of departure 72 of the first leg 62 is opposite the point of departure 74 of the second leg 64. Stated otherwise, relative to an imaginary line intersecting the perimeter 66 and a center point of the center portion 60, the capture body 24 is symmetrical. In other embodiments, the legs 62, 64 can be non-uniformly spaced about the perimeter 66 (e.g., relative to the conventions of FIG. 3B, the point of departure 74 of the second leg 64 can be located at a point other than the six o'clock position shown). In yet other embodiments, three or more of the legs 62, 64 can be provided that may or may not be equidistantly spaced about the perimeter 66.

The center portion 60 and the legs 62, 64 are, in some embodiments, co-planar in the normal arrangement. That is to say, the legs 62, 64 extend in a plane defined by a face of the center portion 60 such that the capture body 24 does not exhibit a three-dimensional spiral or corkscrew attribute in the normal arrangement. Alternatively, however, the legs 62, 64 can be constructed to project out of a plane of the center portion 60 in the normal arrangement.

The capture body 24 is constructed such that the legs 62, 64 elastically resist movement away from the center portion 60, both axially and radially relative to the perimeter 66. For example, a radial or lateral spacing S is defined between an inner surface 80 of the first leg 62 and a region 82 of the perimeter 66 closest to the inner surface 80. As a point of reference, relative to any one point along the inner surface 80, a minimum lateral spacing S is established relative to the closest, adjacent point along the perimeter 66, with this minimum lateral spacing S increasing from the point of departure 72 to the tip 68. An affinity of the first leg 62 to resist laterally outward movement (from the normal arrangement) relative to the perimeter 66 is characterized by the leg 62 resisting a force tending to increase the lateral spacing S. In other words, a force (generically represented by an arrow F in FIG. 3B) exerted or experienced along the inner surface 80 tends to cause the first leg 62 to move in a direction opposite the wind direction A. Construction of the capture body 24 causes the first leg 62 to resist this unwinding-type force. Instead, the first leg 62 (as well as the second leg 64) only slightly deflects in response to the force F, causing material (such as tissue) within the lateral spacing S to gather or pinch between the inner surface 80 and the region 82 of the perimeter 56 as the capture body is rotated in the wind direction A.

Figure 3C:
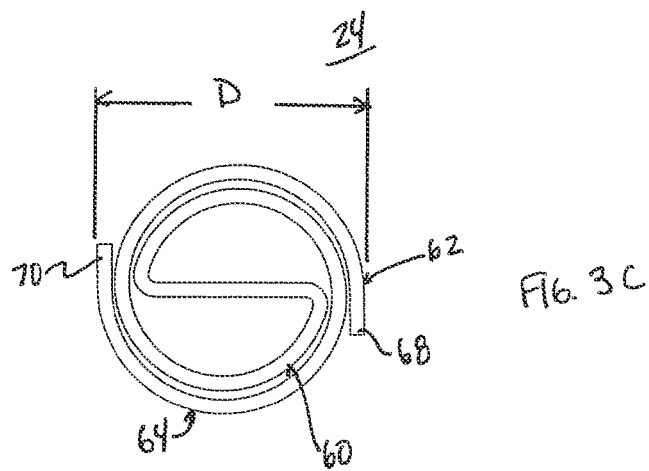
FIG. 3C is a top plan view of the capture body of FIG. 3A in a collapsed arrangement.
Figure 3D:
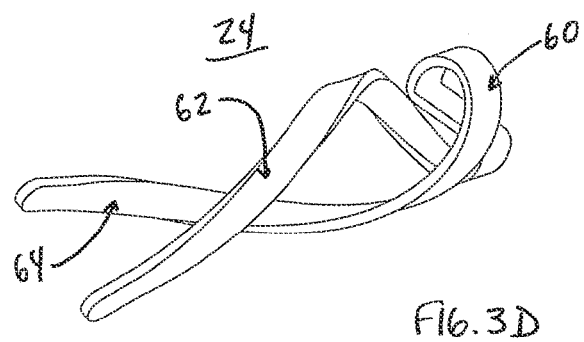
FIG. 3D is a perspective view of the capture body of FIG. 3A in another collapsed arrangement.

In the normal arrangement of FIG. 3B, a maximum outer dimension D of the capture body 24 is defined as a linear distance between the first and second tips 68, 70. The maximum outer dimension D can vary and is selected in accordance with the particular procedure(s) for which the capture body 24 will be used. Regardless, the capture body 24 is collapsible from the normal arrangement to a collapsed arrangement in which the maximum dimension D is greatly reduced. For example, FIG. 3C illustrates one collapsed arrangement of the capture body 24 in which the legs 62, 64 have been forced to wrap onto the center portion 60. Alternatively, FIG. 3D illustrates a differing collapsed arrangement of the capture body 24 in which the legs 62, 64 are forced longitudinally away from the center portion 60, as well as circumferentially collapsed toward one another. Other collapsed arrangements can also be achieved. In any of the collapsed arrangements, the maximum outer dimension D (referenced in FIG. 3C, for example) of the capture body 24 is reduced as compared to the maximum outer dimension D in the normal arrangement, such that the collapsed capture body 24 is more readily delivered to a confined surgical site (e.g., via the delivery catheter 22 (FIG. 1)). Further, upon removal of the force(s) otherwise causing the capture body 24 to assume the collapsed arrangement, the capture body 24, and in particular the legs 62, 64, self-revert back to the normal arrangement of FIGS. 3A and 3B.

An ability of the capture body 24 to self-revert from a collapsed arrangement to the normal arrangement is provided, in some embodiments, by forming the capture body 24 from an elastic material, such as stainless steel, and in other embodiments, a super elastic material such as a shape memory alloy, for example Nitinol. Alternatively, other biocompatible elastic or super elastic materials can be employed. The capture body 24 can optionally be coated with a biocompatible material that promotes tissue healing and/or can contain a drug or therapeutic agent that releases over time.

Returning to FIGS. 1 and 3B, in some constructions, the center portion 60 includes or forms a cross member 90 extending within the circular-like perimeter 66. The cross-member 90 can assume a variety of forms, and in some constructions is configured for fixed interface with the shaft 28 as described below to facilitate transfer of a torque or rotational force applied by the shaft 28 to the legs 62, 64. Where provided, the cross-member 90 can be centrally positioned within the circle-shaped perimeter 66, and bisects an imaginary line connecting the points of departure 72, 74. With this but one acceptable configuration, a torque or rotational moment force applied to the cross-member 90 is relatively uniformly distributed onto the center portion 60 and thus onto each of the legs 62, 64. Alternatively, the cross-member 90 can be asymmetrically positioned relative to the legs 62, 64 and/or can assume a variety of other configurations. In yet other embodiments, the capture body 24 along with a corresponding delivery device (e.g., the shaft 28 (FIG. 1)) are configured to effectuate assembly and force transmission in a manner not otherwise requiring a cross-member, such that the cross-member 90 can be eliminated.

Figure 3E:
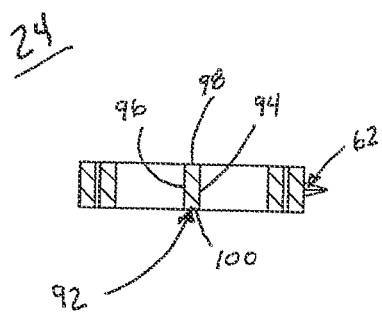
FIG. 3E is a cross-sectional view of the capture body of FIG. 3A, taken along the line 3E-3E.

In some embodiments, the capture body 24 is formed by a single, flat wire 92, the ends or tips 68, 70 of which can be rounded. For example, as shown in FIG. 3E, the continuous wire 92 defines opposing major faces 94, 96, and opposing sides 98, 100. The opposing major faces 94, 96 each define a width that is greater than a width (i.e., thickness) defined by the sides 98, 100. With this flattened construction, occurrences of undesired deviation of the legs 62, 64 from a perpendicular orientation is greatly reduced. In other constructions, however, a round wire (i.e., circular in cross-section) can be employed. Similarly, two or more separately formed wires can be assembled to one another in forming the capture body 24. Even further, the capture body 24 can be formed by component(s) other than a wire.

Figure 3F:
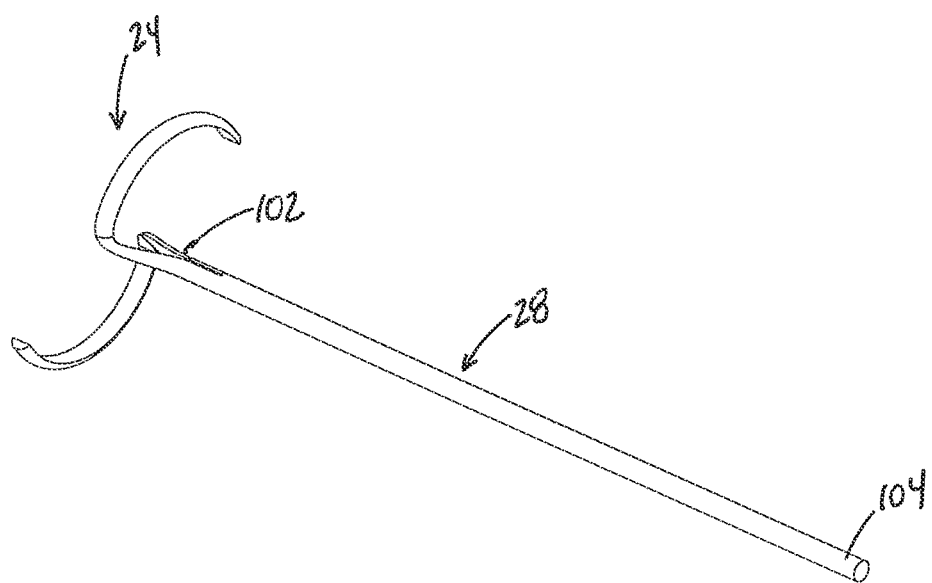
FIG. 3F is a perspective view of a capture body integrally formed with a shaft component of the system of FIG. 1.

Returning to FIG. 1, the shaft 28 is an elongated, solid or tubular body configured for attachment to the capture body 24 at a distal region 102 thereof. Alternatively, the capture body 24 and the shaft 28 can be separately provided, with the distal region 102 of the shaft 28 forming a slot or similar feature sized and shaped for coupling with the capture body 24 (e.g., via the optional cross-member 90 (FIG. 3B)). In some constructions, and as shown in FIG. 3F, the capture body 24 is integrally formed at or by the distal region 102 of the shaft 28 (i.e., the capture body 24 and the shaft 28 are formed as a single, homogenous structure). Regardless, the shaft 28 is sized to be slidably received within the delivery catheter first lumen 50 (FIG. 2), and is sufficiently compliant for traversing a tortuous pathway (e.g., patient's vasculature) yet exhibits sufficient structural strength for transmitting an applied longitudinal force, as well as an applied torque, onto the capture body 24 (e.g., a rotational force applied at a proximal end of the shaft 28 is transmitted to the capture body 24). A proximal region 104 can incorporate various features (not shown) for establishing a linked connection to a handle actuator (not shown) otherwise operable to effectuate sliding and rotational movement of the shaft 28 relative to the catheter 22.

Figure 4:
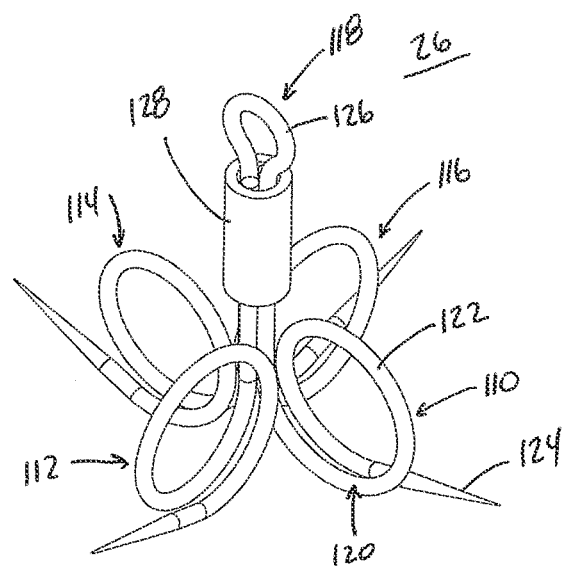
FIG. 4 is a perspective view of a surgical fastener component of the system of FIG. 1.

Returning to FIG. 1, the surgical fastener 26 can assume a variety of forms, and generally include at least one self-closing clip 110. FIG. 4 illustrates one embodiment of the surgical fastener 26 in greater detail, and includes four of the self-closing clips 110-116, along with a base member 118 that interconnects the clips 110-116. The clips 110-116 can be identical, such that the following description of the first clip 110 applies equally to the remaining clips 112-116. The clip 110 comprises a deformable wire 120 made of a shape memory alloy. A nickel titanium (e.g., Nitinol) based alloy may be used, for example. The Nitinol may include additional elements that affect the yield strength of the material or the temperature at which the particular pseudoelastic or shape transformation characteristics occur. The transformation temperature may be defined as the temperature at which a shape memory alloy finishes transforming from a martensite to austenite upon heating (i.e., $A_f$ temperature). The shape memory alloy preferably exhibits pseudoelastic (super elastic) behavior when deformed at a temperature slightly above its transformation temperature. At least a portion of the shape memory alloy is converted from its austenitic phase to its martenestic phase when the wire is in its deformed configuration. As the stress is removed, the material undergoes a martenisitic to austenitic conversion and springs back to its original undeformed arrangement. When the wire is positioned within tissue in its undeformed arrangement, a residual stress is present to maintain the tissue tightly together. In order for the pseudoelastic wire to retain sufficient compression force in its undeformed arrangement, the wire should not be stressed past its yield point in its deformed arrangement to allow complete recovery of the wire to its undeformed arrangement.

Regardless of the exact material or manufacturing technique, the clip 110 has a memory set shape (i.e., the normal arrangement) that forms one or more complete or partial loops 122. In a deflected arrangement, the clip 110 can be rendered substantially straight or linear (e.g., the loop(s) 122 is no longer discernable). Upon removal of the deflection force, the clip 110 self-transitions or reverts back to the memory set loop shape of the undeflected arrangement, reforming the loop(s) 122.

With embodiments in which the surgical fastener 26 includes four of the clips 110-116, the clips 110-116 can be equidistantly spaced from one another relative to the base member 118. For example, the first and third clips 110, 114 extend from the base member 118 in opposite directions, as do the second and fourth clips 112, 116. The second clip 112 is located between the first and third clips 110, 114, and the fourth clip 116 is opposite the second clip 112. Each of the clips 110-116 terminates in a tip 124 that can be sharpened as shown.

The base member 118 can assume various forms, and in some embodiments is constructed for interface with the fastener delivery assembly 30 (FIG. 1). For example, the base member 118 can form a hook 126 or similar loop-shaped structure. A ring 128 or similar body can be provided, and serves to crimp the clips 110-116 to one another at the base member 118. For example, a first wire can be processed to form the first and third clips 110, 114 and the hook 126, a second wire forms the second clip 112, and a third wire forms the fourth clip 116; the ring 128 crimps the second and third wires to the first wire, with the hook 126 being exposed proximal the ring 128. Other attachment constructions are also envisioned, such as adhesive, glue, solder, welds, etc.

Figure 5:
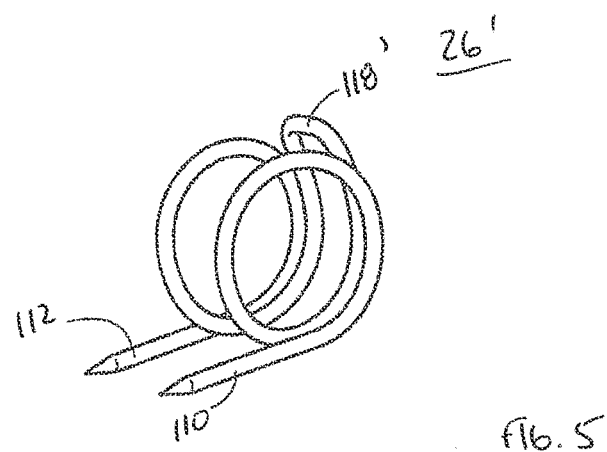
FIG. 5 is a perspective view of another surgical fastener useful with the system of FIG. 1.

While the surgical fastener 26 has been shown and described as including four of the self-closing clips 110-116, in other embodiments, a greater or lesser number can be provided. For example, FIG. 5 illustrates an alternative embodiment surgical fastener 26' useful with systems and methods of the present disclosure that includes two of the self-closing clips 110, 112 (shown in the undeflected arrangement) interconnected by a base member 118'.

Returning to FIG. 1, the fastener delivery assembly 30 can assume a variety of forms, and in some embodiments includes a push tube 140 and a tether 142. The push tube 140 defines proximal and distal ends 144, 146, and is sized to be slidably disposed within the second lumen 52 (FIG. 2) of the delivery catheter 22. The push tube 140 is sufficiently compliant for passage through the patient's vasculature, yet exhibits sufficient longitudinal strength for transmitting a longitudinal pushing force onto the surgical fastener 26. The tether 142 is disposed (threaded) within the push tube 140 and has sufficient length such that when loaded into the push tube 140, opposing ends 148, 150 thereof extend beyond the proximal end 144 of the push tube 140 while an intermediate portion 152 extends beyond the distal end 146 of the push tube 140. With this construction, the fastener delivery assembly 30 can be selectively connected with the surgical fastener 26 by looping the tether 142 about the hook 126, and threading the tether 142 through the push tube 140.

Figure 6:
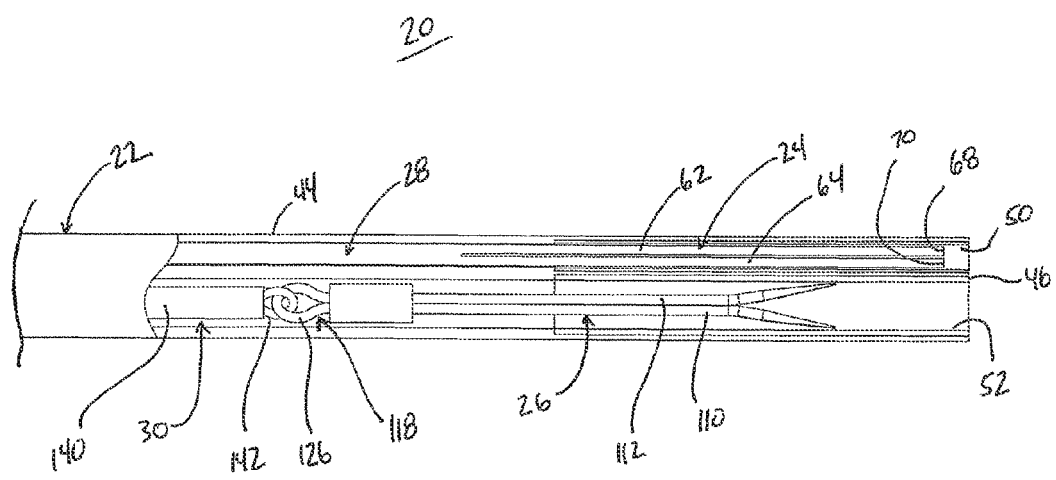
FIG. 6 is an enlarged cross-sectional view of a distal region of the system of FIG. 1 upon final assembly and in a delivery state.

FIG. 6 illustrates a distal region of the repair system 20 upon final assembly and in a delivery state. The capture body 24 is disposed within first lumen 50, with the distal section 44 of the delivery catheter 22 forcing the capture body 24 to a collapsed arrangement. In the collapsed arrangement, the legs 62, 64 of the capture body 24 are rendered substantially linear, with the corresponding tips 68, 70 being proximal the catheter distal end 46. As a point of reference, with the construction illustrated in FIG. 6, the capture body 24 is integrally formed with or by the shaft 28. The capture body 24 and the shaft 28 are longitudinally slidable relative to the delivery catheter 22, with the proximal region 104 (FIG. 1) of the shaft 28 optionally extending beyond the proximal end 42 (FIG. 1) of the catheter 22 and/or connected to a handle actuator that facilitates user manipulation of the shaft 28, and thus of the capture body 24, relative to the delivery catheter 22. As shown in FIG. 6, one or both of the lumens 50, 52 can be slightly enlarged immediately adjacent the catheter distal end 46 to house a stainless steel or other rigid tube (not shown) that reduces resistance to sliding of the capture body 24 and the surgical fastener 26, respectively. Further, the slight enlargement of the lumens 50, 52 allows the catheter 22 to more easily accommodate the capture body legs 62, 64 and the clips 110-116, respectively.

The surgical fastener 26 is similarly disposed entirely within the second lumen 52 of the catheter 22. The catheter distal section 44 forces the clips 110-116 (two of which are visible in the view of FIG. 6) to a deflected arrangement. The clips 110-116 are entirely proximal the distal end 46 of the catheter 22. In the delivery state of FIG. 6, the fastener delivery assembly 30 is connected to the surgical fastener 26 via looping of the tether 142 through the hook 126 of the base member 118. As previously described, the tether 142 is threaded through the push tube 140, and the opposing ends 148, 150 (FIG. 1) are accessible beyond the proximal end 42 (FIG. 1) of the delivery catheter 22. The push tube 140 can similarly be acted upon by a user proximal the catheter 22. As a point of reference, longitudinal distal movement of the push tube 140 directs the push tube distal end 146 into an abutting relationship with the base member 118, resulting in a corresponding distal movement of the surgical fastener 26 relative to the catheter 22. Conversely, a proximal or pulling force applied to the tether 142 causes the surgical fastener 26 to move or slide proximally relative to the catheter 22.

Figure 7A:
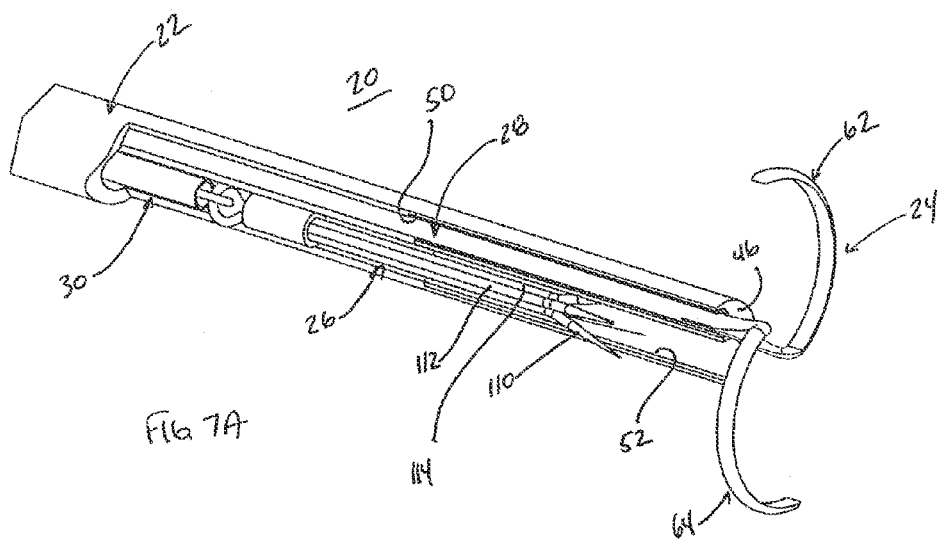
FIG. 7A is an enlarged perspective view of a distal region of the system of FIG. 1 with portions removed and in a chordae capture state.
Figure 7B:
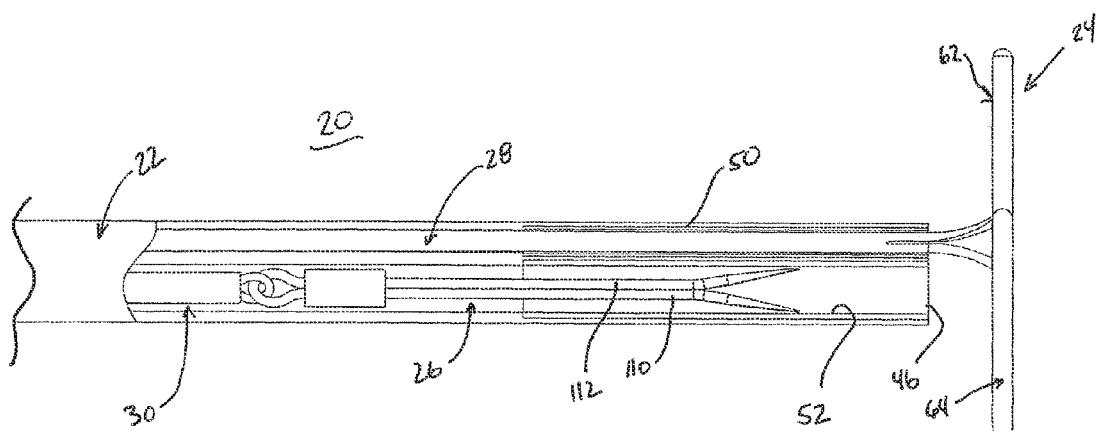
FIG. 7B is a cross-sectional view of the distal region of FIG. 7A.

During use, the repair system 20 is transitionable from the delivery state of FIG. 6 to a chordae capture state illustrated in FIGS. 7A and 7B. In transitioning from the delivery state to the capture state, the shaft 28 is caused to slide distally within the first lumen 50, in turn positioning or locating the capture body 24 (or at least a substantial portion of the legs 62, 64) distal the catheter distal end 46. As shown, once the capture body 24 is free of the confines of the catheter 22, the capture body 24 (or at least the legs 62, 64) self-reverts from the collapsed arrangement of FIG. 6 to or towards the normal arrangement reflected in FIGS. 7A and 7B. The legs 62, 64 expand radially outwardly. In some embodiments, in the capture state, a plane defined by the legs 62, 64 is substantially perpendicular (e.g., within 10° of a truly perpendicular relationship) to a central axis of the catheter 22, and a diameter collectively defined by the legs 62, 64 is greater than a diameter of the catheter 22. Notably, the repair system 20 is configured such that the capture body 24/shaft 28 can be moved relative to the delivery catheter 22 independent of the surgical fastener 26/fastener delivery assembly 30. Thus, in the capture state, the surgical fastener 26 remains entirely within the second lumen 52, and thus the clips 110-116 (two of which are visible in FIG. 7B) remain in the deflected arrangement. As previously described, the shaft 28 is constructed to transfer an applied torque onto the capture body 24. User-prompted rotation of the shaft 28 (e.g., via a thumb wheel located at the proximal section 40 (FIG. 1) of the delivery catheter 22) causes the capture body 24 to rotate relative to the delivery catheter 22. Further, a longitudinal spacing between the legs 62, 64 and the catheter distal end 46 can be altered by sliding the shaft 28 relative to the catheter 22, and/or vice-versa.

The repair system 20 further provides a partial clip deployment state as shown in FIGS. 8A and 8B. Transitioning from the capture state to the partial clip deployment state generally entails distally sliding the surgical fastener 26 along the second lumen 52 via a user-applied force on the push tube 140. As shown, the distal end 146 of the push tube 140 is caused to abut the base member 118, with further distal movement of the push tube 140 thus being transferred onto the surgical fastener 26. As the clips 110-116 are thus directed distally beyond the distal end 46 of the catheter 22, the clips 110-116 self-revert to or toward the undeflected arrangement. In the partial clip deployment state, the capture body legs 62, 64 are distally spaced from the catheter distal end 46 such that the deployed capture body 24 has minimal interference with self-transitioning of the clips 110-116 toward the normal arrangement. The second lumen 52 can also have a square shape in transverse cross-section that assists in ensuring that the tips 124 of each of the clips 110-116 deploy in a normal fashion. Further, the surgical fastener 26 is arranged relative to the shaft 28 such that the clips 110-116 self-expand about the shaft 28. For example, and as best shown in FIG. 8A, the shaft 28 is located "between" the second and third clips 112, 114. Thus, the clips 110-116 substantially freely transition toward the undeflected arrangement when directed distally beyond the catheter distal end 46.

Figure 10A:
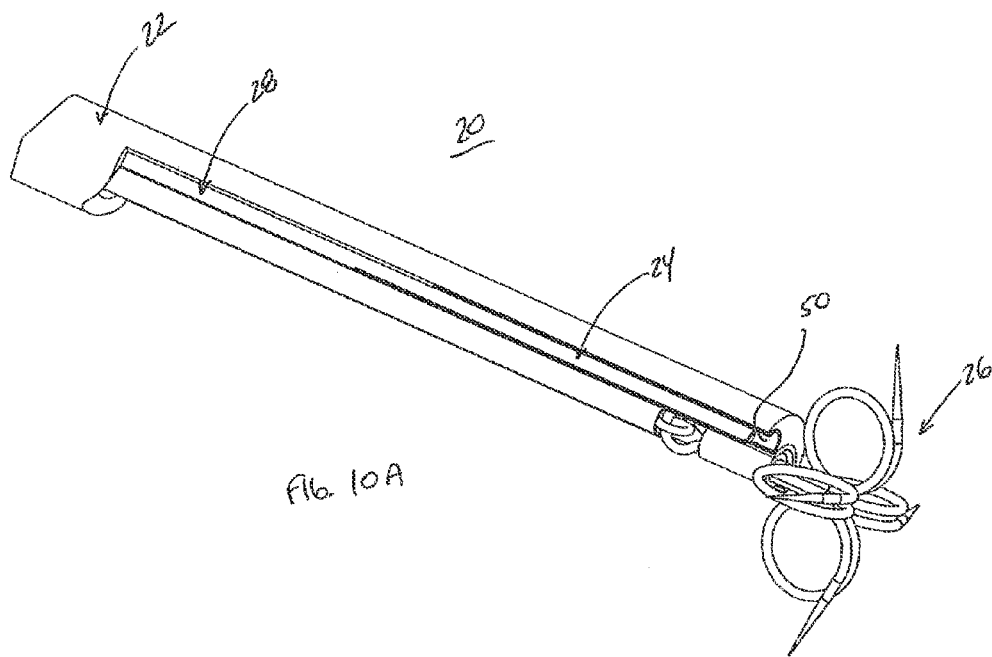
FIG. 10A is an enlarged perspective view of a distal region of the system of FIG. 1 with portions removed and illustrating the full clip deployment state and the capture body retracted.
Figure 10B:
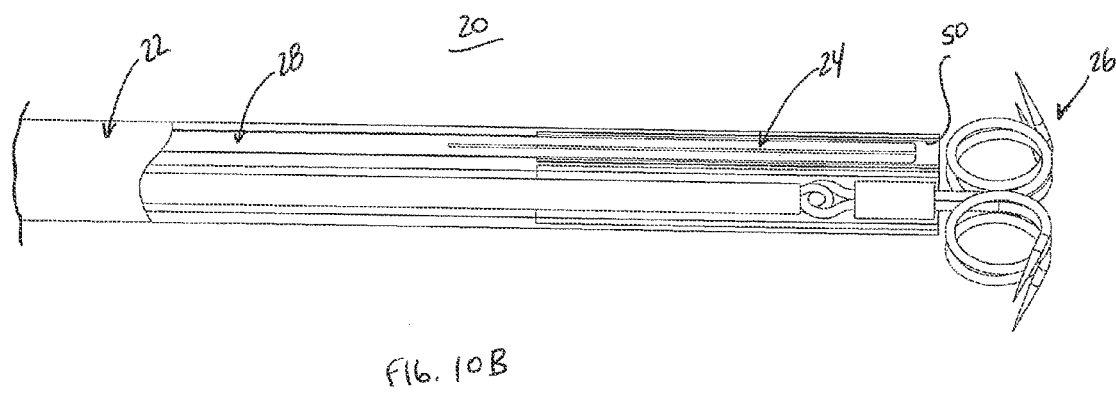
FIG. 10B is a cross-sectional view of the distal region of FIG. 10A.
Figure 11A:
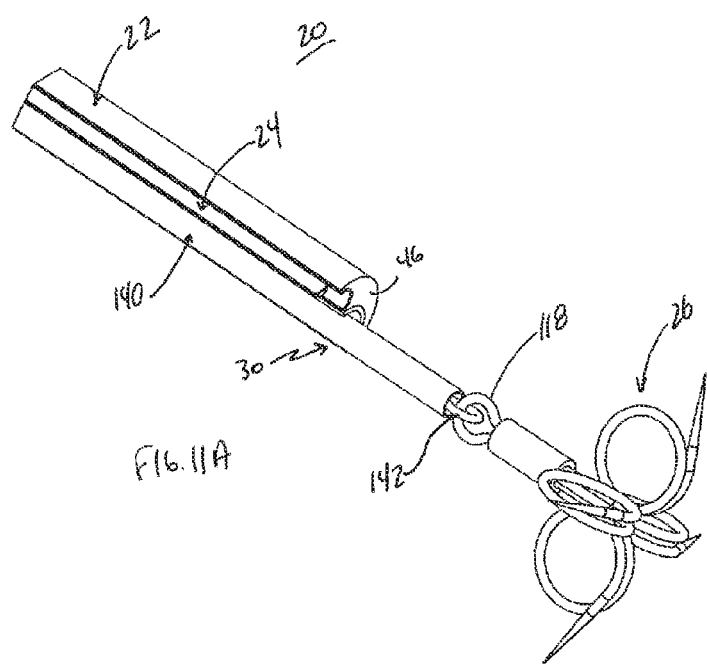
FIG. 11A is an enlarged perspective view of a distal region of the system of FIG. 1 with portions removed and in a surgical fastener release state.
Figure 11B:
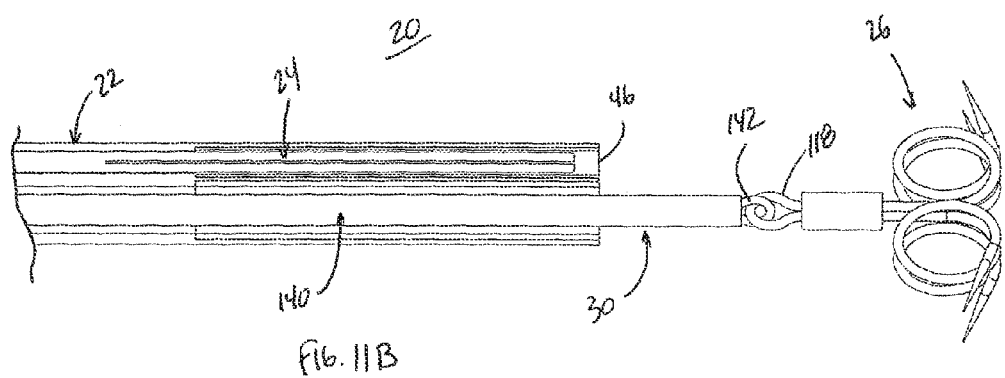
FIG. 11B is a cross-sectional view of the distal region of FIG. 11A.

The repair system 20 is further transitionable to a full clip deployment state as illustrated in FIGS. 9A and 9B. More particularly, further distal movement of the push tube 140 relative to the catheter 22 (from the arrangement of FIGS. 8A and 8B) directs the clips 110-116 entirely distally beyond the catheter distal end 46. The clips 110-116 thus freely self-transition to or toward the undeflected arrangement, forming the loop(s) 122 as described above. The capture body 24/shaft 28 remains longitudinally stationary, with the clips 110-116 self-reverting in highly close proximity to the capture body legs 62, 64. As reflected by FIGS. 10A and 10B, the capture body 24 can subsequently be retracted back into the first lumen 50 via proximal movement of the shaft 28 relative to the delivery catheter 22. The delivery catheter 22 forces the capture body 24 back to the collapsed arrangement, with the capture body 24 being fully encompassed within the first lumen 50. Finally, in a relaxed state of the system 20 shown in FIGS. 11A and 11B, the push tube 40 is further distally advanced relative to the delivery catheter 22 (or vice-versa), locating an entirety of the surgical fastener 26 beyond the catheter distal end 46. The surgical fastener 26 can be completely released from a remainder of the system by unthreading the tether 142 from the base member 118.

The repair system 20 can incorporate a variety of other structures or mechanisms operable to sequentially deploy the capture body 24 and the surgical fastener 26, as well as release the surgical fastener 26. The present disclosure is not limited to the shaft 28 or the fastener delivery assembly 30 as described above. Also, alternative repair systems and methods of the present disclosure can incorporate one or more additional delivery catheters. For example, the capture body 24 can be carried by a first delivery catheter, and the surgical fastener 26 carried by a separate, second delivery catheter.

Figure 12A:
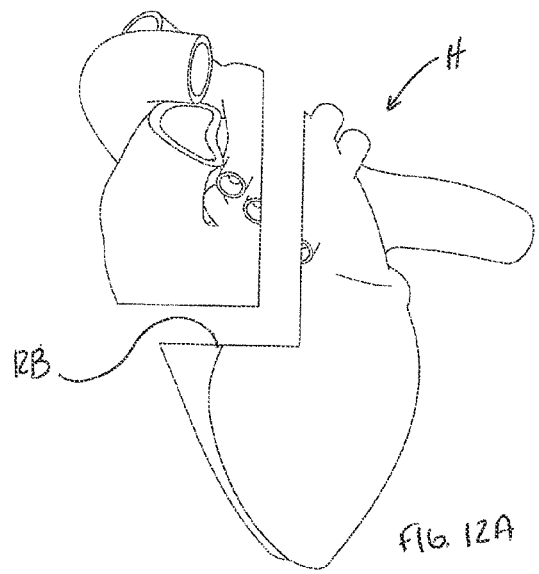
FIG. 12A is a simplified anterior view of a human heart.
Figure 12B:
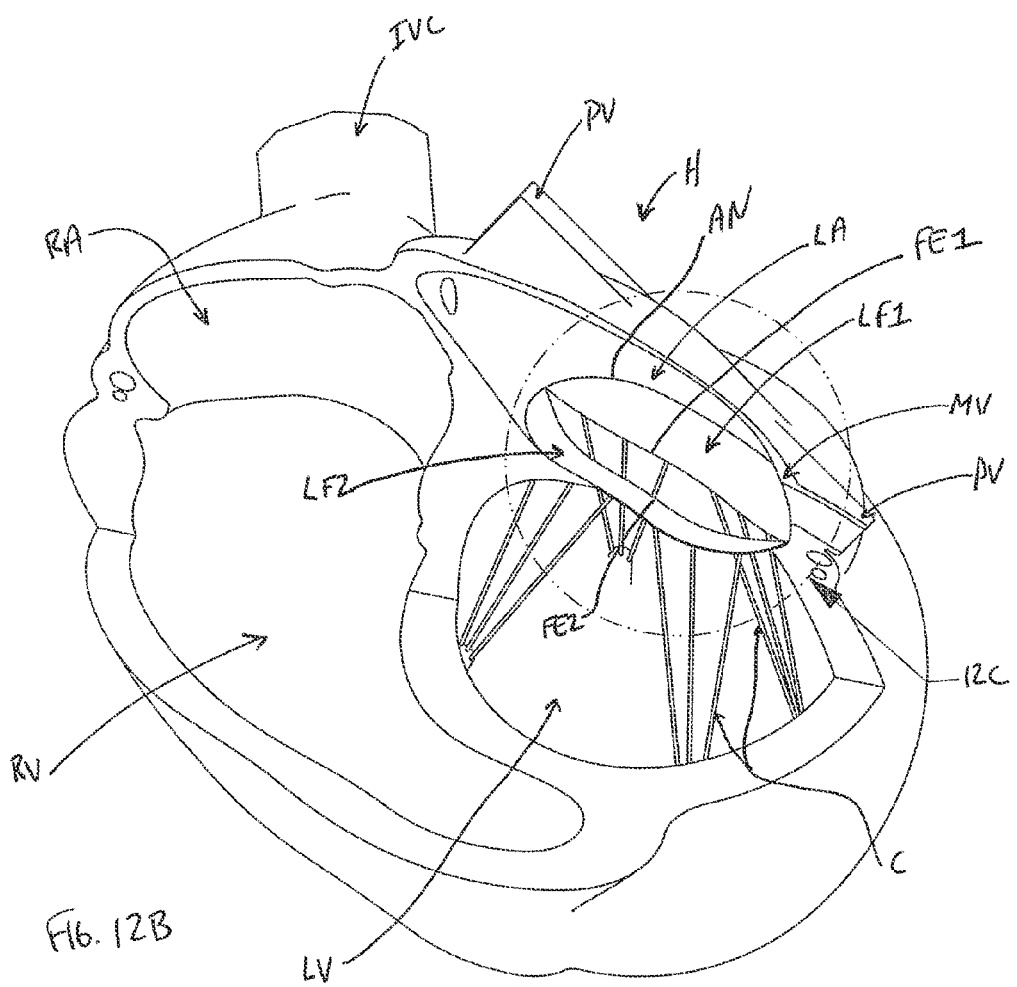
FIG. 12B is a partial cross-sectional view of the heart of FIG. 12A along section line 12B.
Figure 12C:
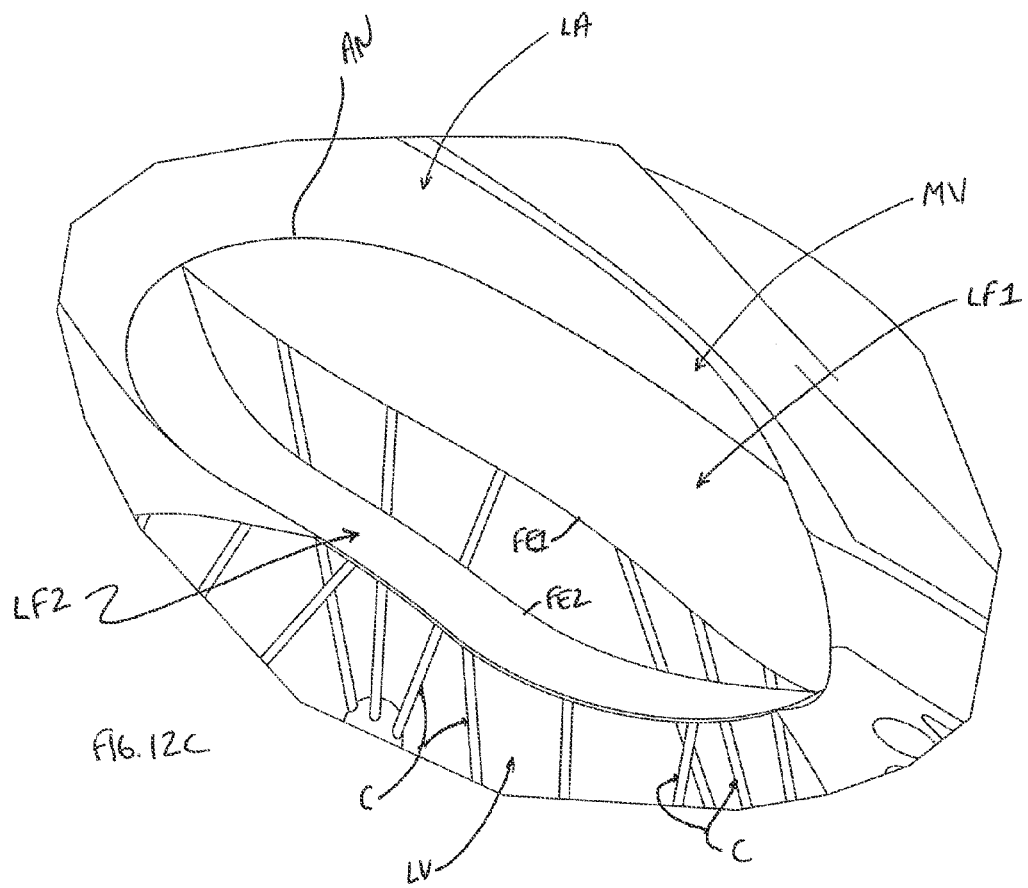
FIG. 12C is an enlarged perspective view of a portion of the heart of FIG. 12B, illustrating a mitral valve in an open arrangement.
Figure 12D:
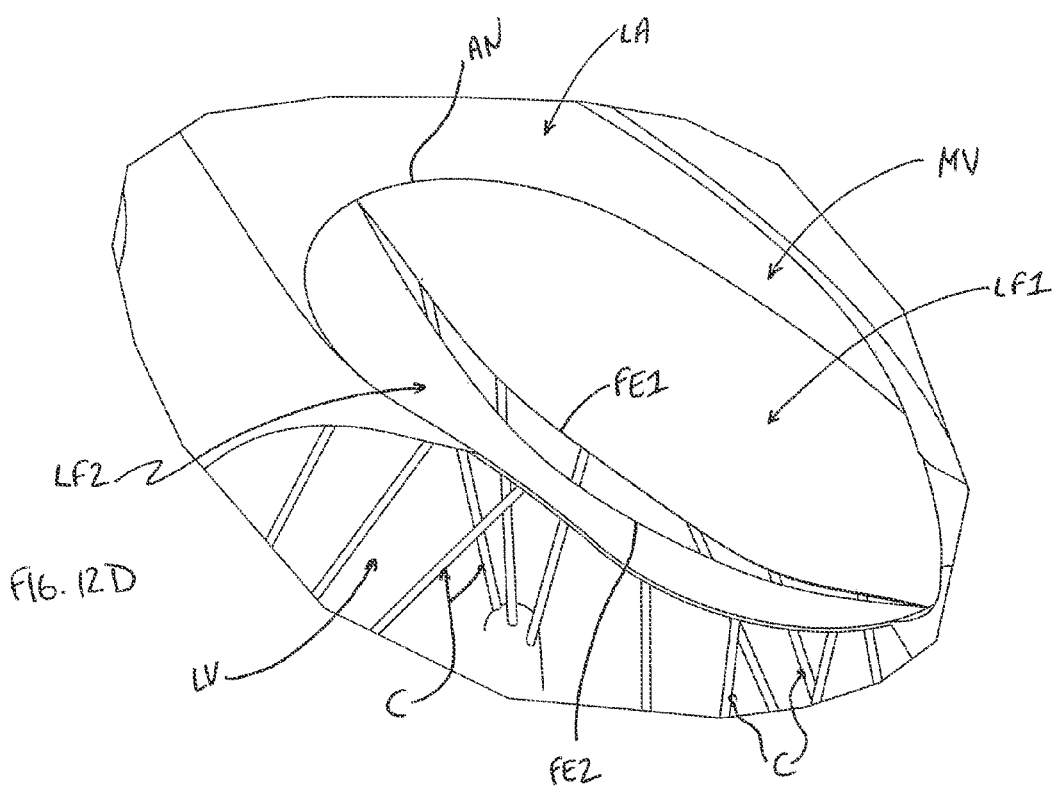
FIG. 12D is an enlarged perspective view of a portion of the heart of FIG. 12B in systole and illustrating a defective mitral valve.

The repair system 20 is useful in performing a variety of endovascular repair procedures. One particular procedure is the repair of a mitral valve. Anatomy of a normal heart H is shown in FIGS. 12A-12C. The mitral valve MV is located between the left atrium LA and the left ventricle LV. Also shown are the inferior vena cava IVC, right atrium RA, right ventricle RV, and pulmonary veins PVs. The mitral valve MV includes first and second leaflets LF1, LF2 extending from a valve annulus AN (referenced generally). Each of the leaflets LF1, LF2 terminates at a free edge FE1, FE2. The free edges FE1, FE2 are secured to lower portions of the left ventricle LV through chordae C. When the heart H is in systole, backflow of blood or "regurgitation" through the mitral valve MV is prevented by the free ends FE1, FE2 of the leaflets LF1, LF2 overlapping one another or coapting. Disease or other anatomical deficiencies can prevent coaptation from occurring as shown in FIG. 12D, resulting in mitral valve regurgitation. Systems and methods of the present disclosure can be used to treat this malady.

Figure 13A:
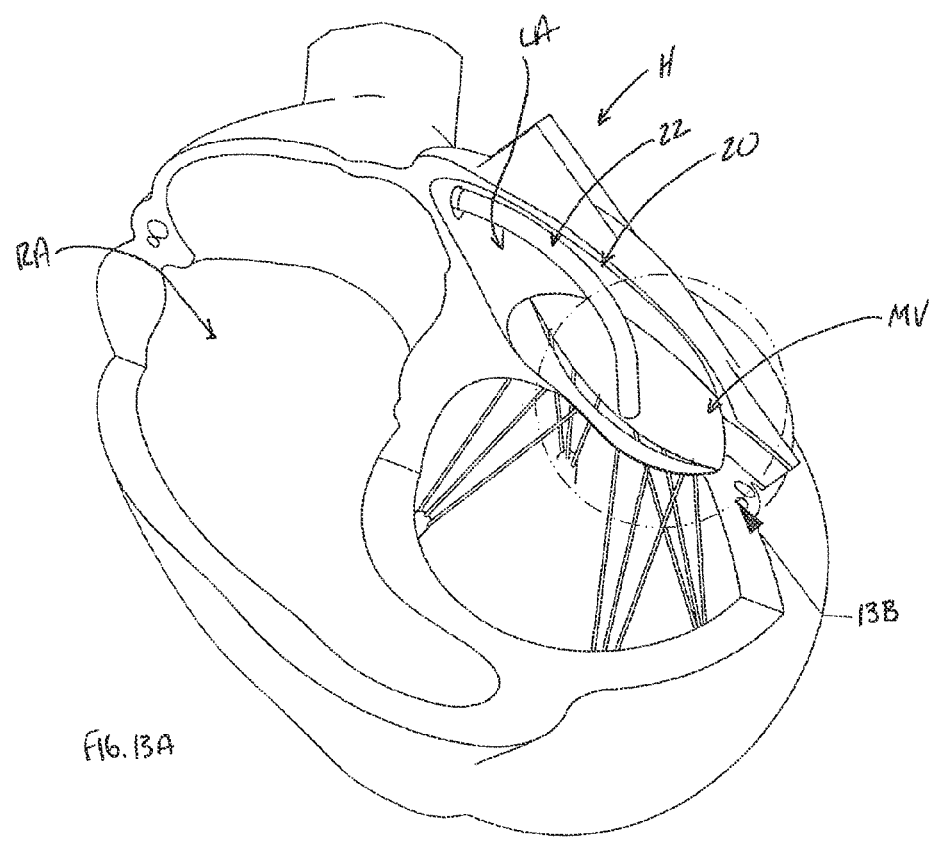
Figure 13B:
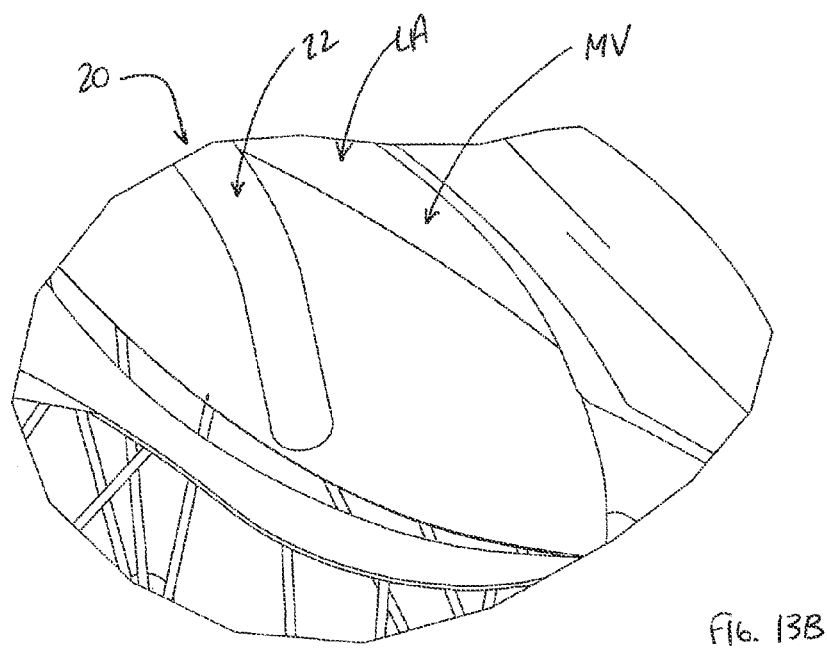

In particular, and with reference to FIGS. 13A and 13B, the repair system 20 (referenced generally) is arranged in the delivery state described above (FIG. 6), and percutaneously delivered to the mitral valve MV target site via the patient's vasculature. For example, the delivery catheter 22 can be routed through the femoral vein, into the right atrium RA, and then across the septum through a punctured hole by following a guide-wire, through an introducer, or by direct navigation. The catheter distal end 46 is thus directed into the left atrium LA, and positioned immediately proximate the mitral valve MV target site.

The repair system 20 is then transitioned to the capture state as shown in FIGS. 14A and 14B that otherwise reflect the capture body legs 62, 64 deployed distal the distal end 46 of the delivery catheter 22, and within the left ventricle LV. In this regard, the capture body 24 can first be deployed from the catheter distal end 46 within the left atrium LA and then directed between the leaflets LF1, LF2 and into the left ventricle LV, or the distal end 46 of the delivery catheter 22 can be arranged relative to the leaflets LF1, LF2 such that deployment of the capture body 24 from the distal end 46 occurs directly within the left ventricle LV. Regardless, in the position of FIGS. 14A and 14B, the deployed capture body legs 62, 64 are located to interface with several of the chordae C.

Figure 15A:
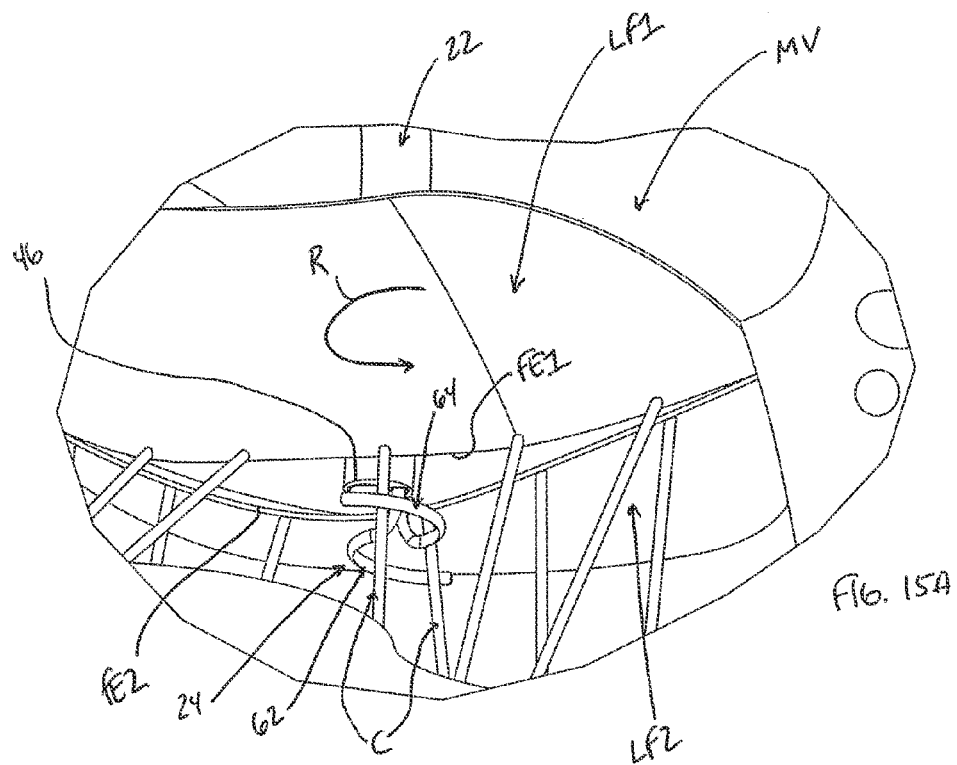
Figure 15B:
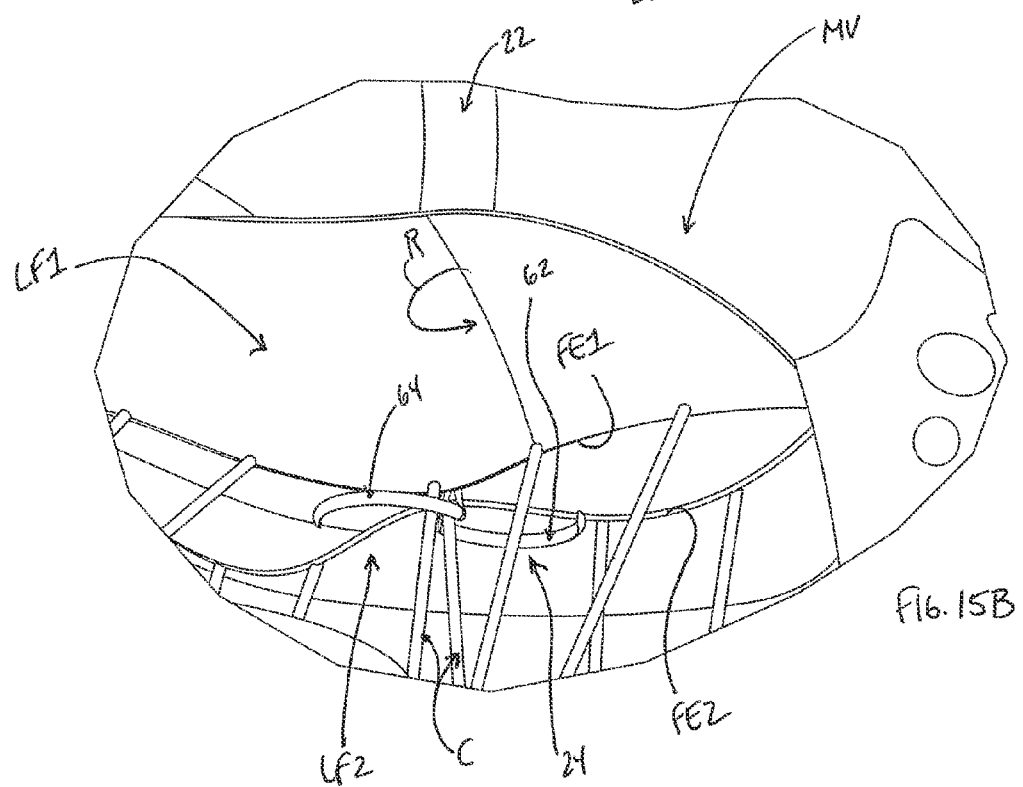

More particularly, and as shown in FIG. 15A, the delivery catheter distal end 46 is guided to a position near a center of the mitral valve MV. This guiding can be done using any number of methods, and can entail use of a standard pull wire that runs the length of the catheter 22. Regardless, once desirably positioned, the capture body 24 is caused to rotate relative to the delivery catheter 22 in the wind direction described above (represented by an arrow R in FIG. 15A). As the capture body 24 rotates, chordae C associated with the opposing leaflets LF1, LF2 are engaged by the legs 62, 64, and drawn toward the center portion 60 (referenced generally in FIG. 15A) and thus toward one another. FIG. 15B illustrates that with further rotation R of the capture body 24 in the wind direction, the engaged chordae C are caused to move toward a center of the capture body 24. This action, in turn, draws or pulls corresponding segments of the opposing free edges FE1, FE2 into contact, or at least in highly close proximity, with one another. Confirmation of optimal capture of the chordae C (and thus of the opposing leaflets LF1, LF2) can be done via echocardiogram and/or fluoroscopy. If the positioning is not as desired, the capture body 24 can be rotated in an opposite direction (i.e., direction opposite the wind direction) to release the captured chordae C, the delivery catheter 22 repositioned, followed by another attempt to capture desired chordae C. Conversely, if the capture body 24 gets caught in the chordae C, the capture body 24 can simply be retracted back into the delivery catheter 22, thus disengaging the chordae C.

Once the leaflets LF1, LF2 are captured via engagement of chordae C with the capture body 24, the delivery catheter 22 is distally advanced relative to the capture body 24 until the leaflets LF1, LF2 are sandwiched between the distal end 46 and the capture body 24.

Figure 16A:
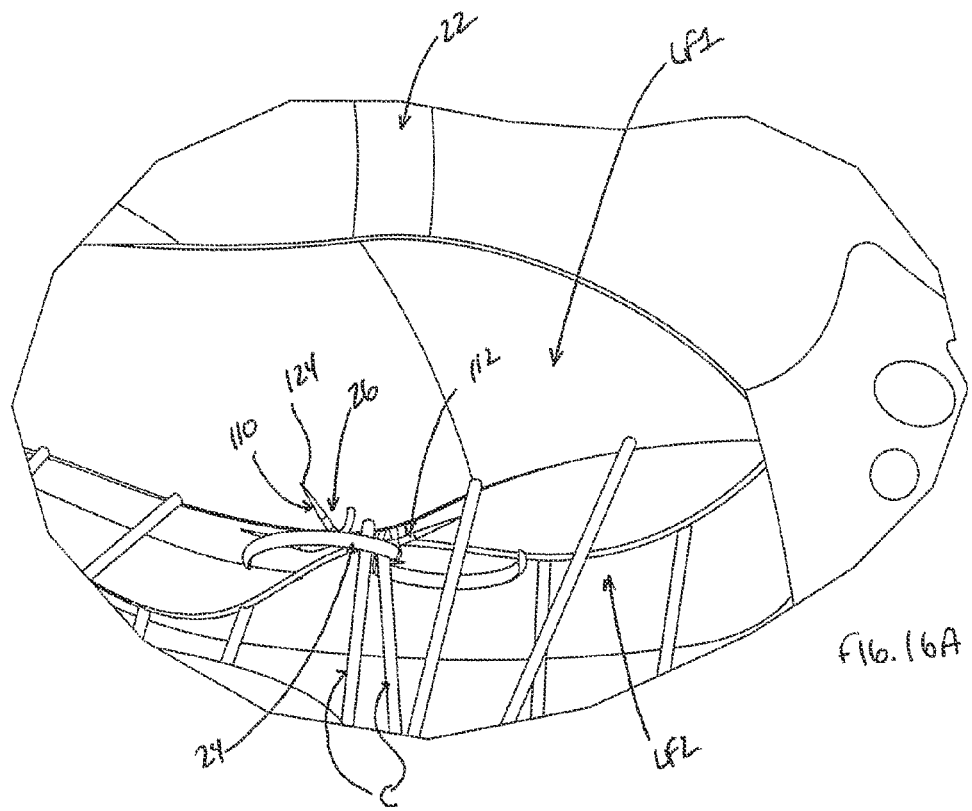
Figure 16B:
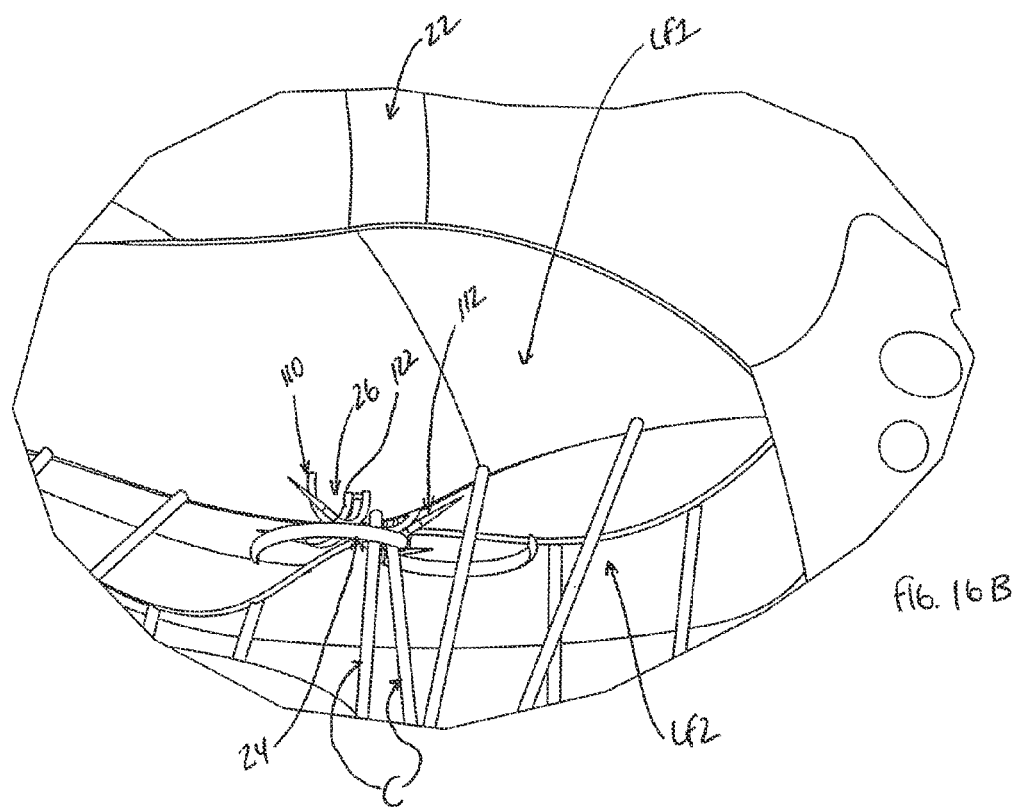

The repair system 20 is then transitioned through the clip deployment states as reflected in FIGS. 16A and 16B. As previously described, in the partial clip deployment state (FIG. 16A), the surgical fastener 26 (referenced generally) is distally advanced relative to the delivery catheter 22 such that a portion of the clips 110-116 (two of which are visible in FIG. 16A) are exposed beyond the distal end 56 (hidden in FIG. 15A) of the catheter 22, and begin to self-transition toward the undeflected arrangement. Due to the catheter distal end 46 being in close proximity to the opposing leaflets LF1, LF2, the self-deploying clips 110-116 pierce through tissue of one or both of the leaflets LF1, LF2. For example, FIG. 16A reflects the tip 124 of the first clip 110 protruding through the first leaflet LF1. The full clip deployment state shown in FIG. 16B. Distal advancement of the surgical fastener 26 relative to the delivery catheter 22 has continued until the clips 110-116 (two of which are visible in FIG. 16B) are fully exposed distal the delivery catheter distal end 46 (hidden in FIG. 16B) and self-revert to the undeflected arrangement. For example, FIG. 16B illustrates the first clip 110 self-reverted to the undeflected arrangement and forming the loop 122. When the system 20 is desirably positioned and operated, each of the leaflets LF1, LF2 will be fastened by at least a respective one of the clips 110-116.

Figure 17A:
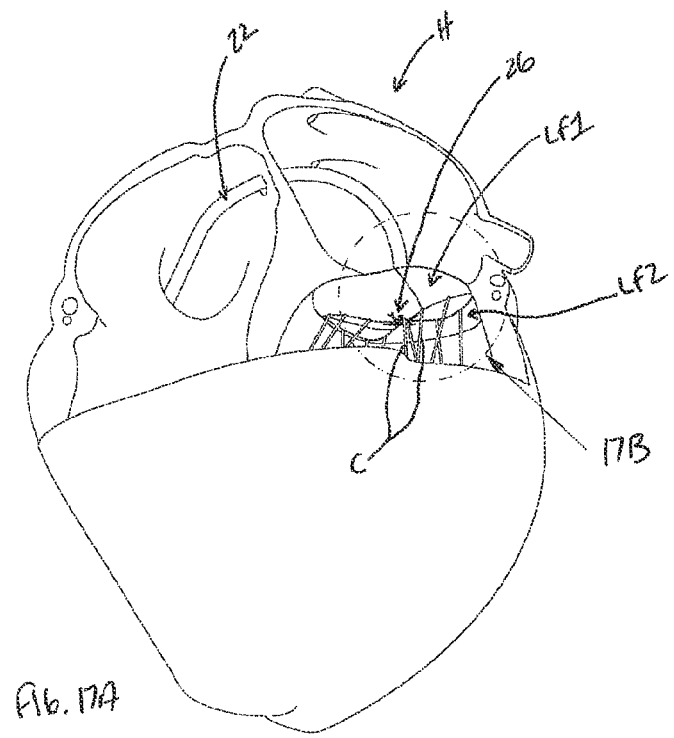
Figure 17B:
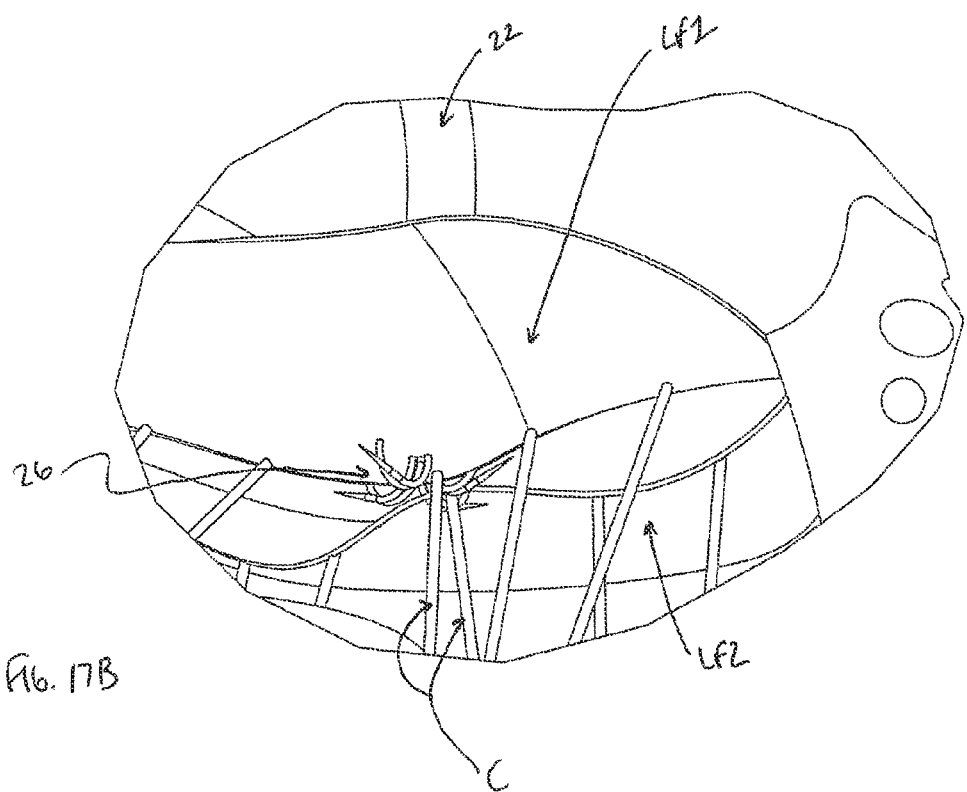
Figure 18A:
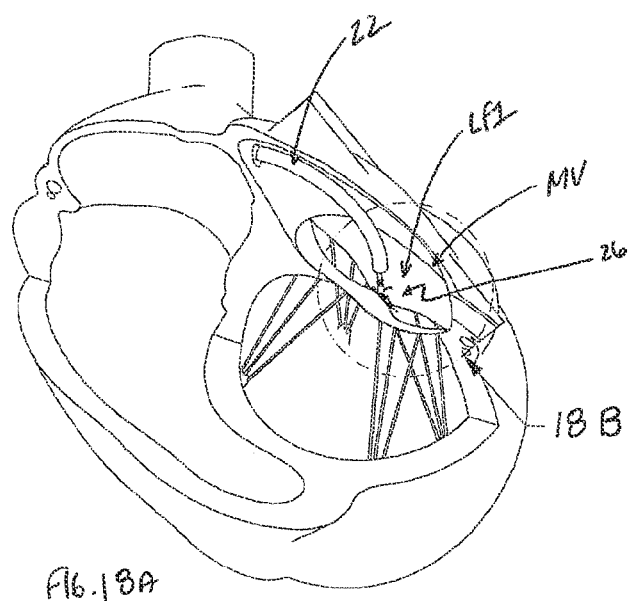
Figure 18B:
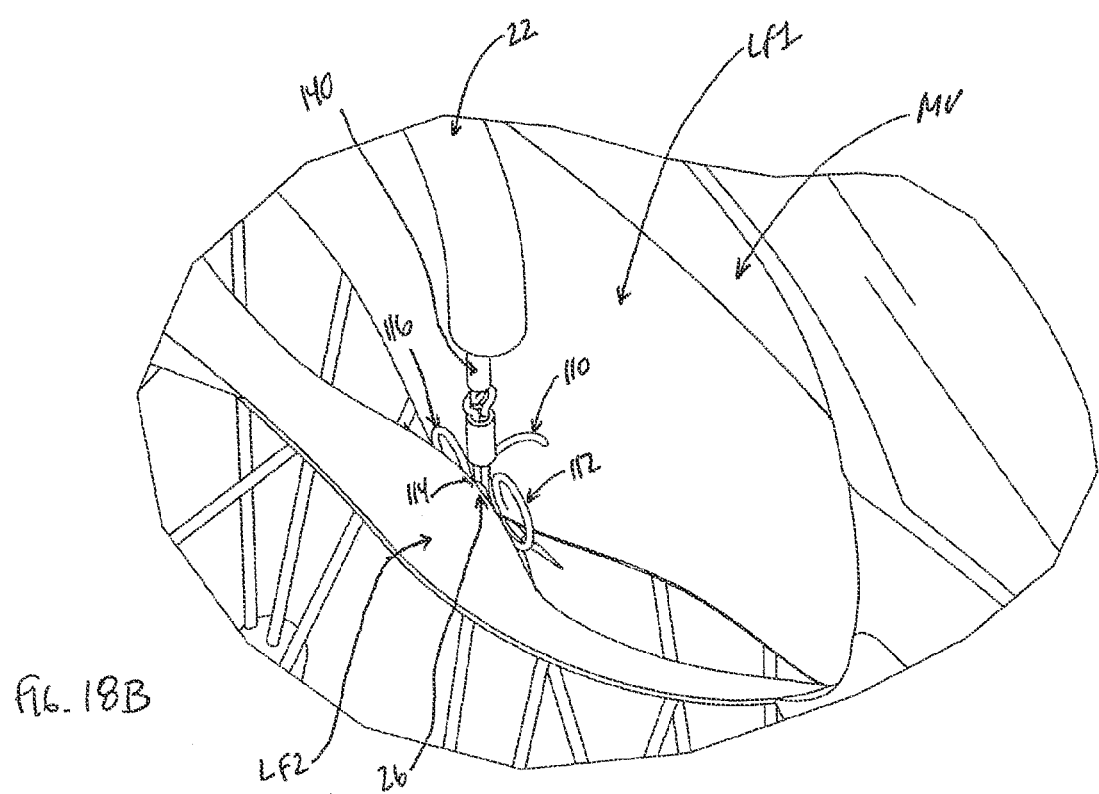

After the clips 110-116 are fully deployed, rotational tension is released at the proximal end 104 (FIG. 1) of the shaft 28, allowing the capture body 24 to relax in relation to the previously captured chordae C. The capture body 24 can then be proximally retracted into the delivery catheter 22. As shown in FIGS. 17A and 17B, the capture body 24 (hidden) is withdrawn from the chordae C. In this arrangement, desired engagement of the leaflets LF1, LF2 by the surgical fasteners 26 can be confirmed. For example, the catheter 22 can be proximally retracted to space the distal end 46 from the mitral valve MV as shown in FIGS. 18A and 18B. Using echocardiogram, fluoroscopy, or other conventional techniques, an evaluation of the mitral valve MV is performed to determine whether the first leaflet LF1 is fastened to or captured by at least one of the clips 110-116 (three of which are visible in the view of FIG. 18B), and whether the second leaflet LF2 is fastened to or captured by at least one of the clips 110-116. For example, FIG. 17B illustrates the first leaflet LF1 fastened to the first clip 110, and the second leaflet LF2 fastened to the third clip 114 (referenced generally). Alternatively, a correctly captured location of the surgical fastener 26 can entail both of the leaflets LF1, LF2 being fastened to a single one of the clips 110-116.

Figure 19A:
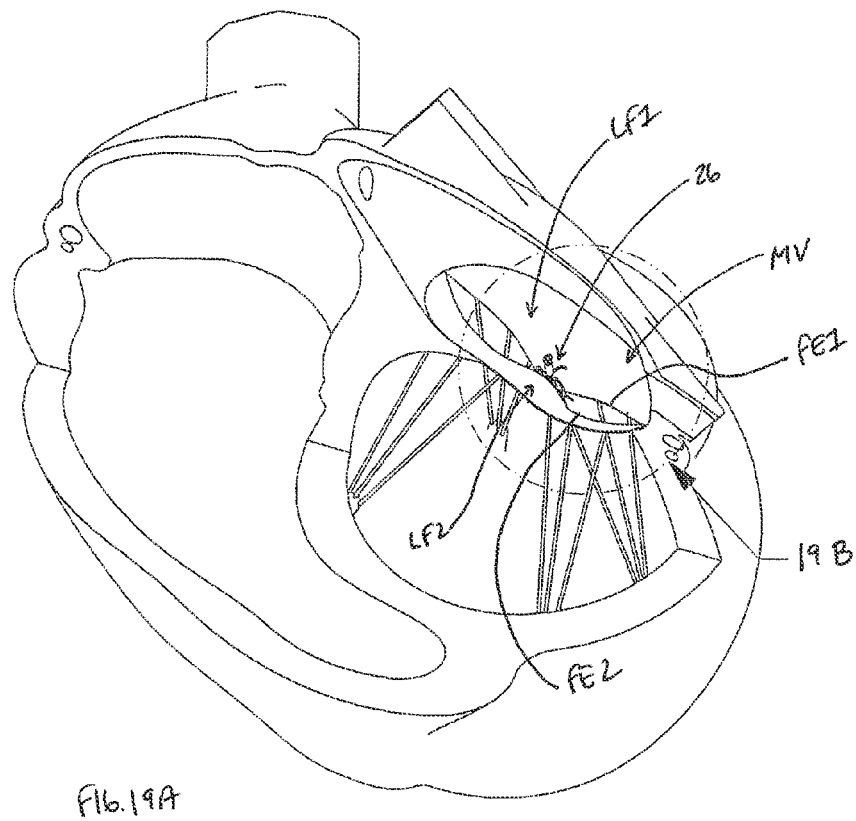
FIGS. 19A and 19B illustrate the repaired mitral valve.
Figure 19B:
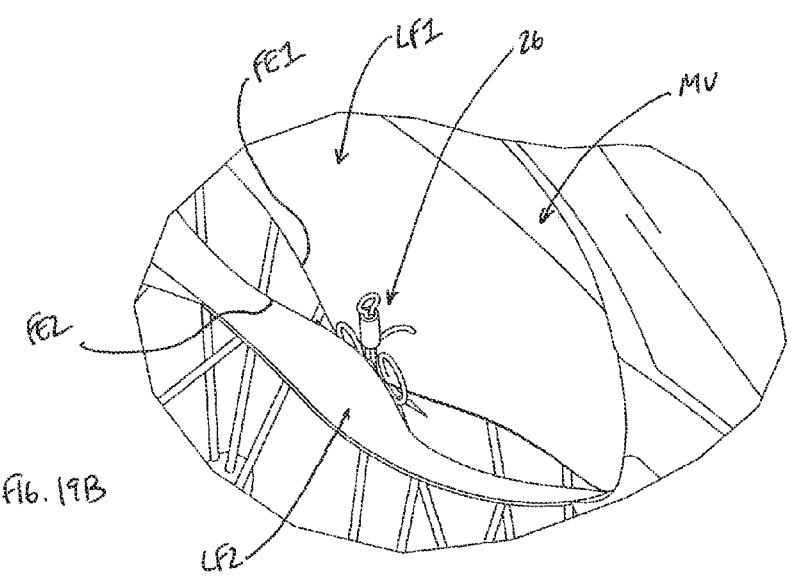

If it is determined that the surgical fastener 26 did not capture both leaflets LF1, LF2, the tether 142 (FIG. 1) can be pulled to retract the surgical fastener 26 back into the delivery catheter 22, returning the clips 110-116 to the deflected arrangement. Because the distal end 46 of the delivery catheter 22 abuts against one or both of the leaflets LF1, LF2, the clips 110-116 follow a relatively axial path back into the catheter lumen 52 (FIG. 2) such that retraction of the surgical fastener 26 back into the delivery catheter 22 will not create a tear in the leaflets LF1, LF2 but will leave small holes (approximately the size of the wire diameter). The chordae capturing and surgical fastener placement procedures described above are then repeated. Conversely, if the surgical fastener 26 is located as desired, the surgical fastener 26 is then released from a remainder of the repair system 20 by removing the tether 142 (e.g., one of the two tether ends 148, 150 (FIG. 1) is pulled to unthread the tether 142 from the surgical fastener 26 and the push tube 140). Once released, the delivery catheter 22 is removed form the patient, resulting in the repaired mitral valve arrangement shown in FIGS. 19A and 19B. When correctly located, segments of the opposing free edges FE1, FE2 are held together in highly close proximity. Thus, during systole, the leaflets LF1, LF2 will close or coapt as with a normal mitral valve to prevent regurgitation.

A portion of another embodiment percutaneous mitral valve repair system 200 in accordance with principles of the present disclosure is shown in FIG. 20. The system 200 includes a delivery catheter 202, a capture assembly 204, and a fastener delivery assembly 206 (a guide sheath 208 component of which is visible in FIG. 20). The system 200 further includes surgical fastener, such as the surgical fastener 26 described above. Details on the various components are provided below. In general terms, however, the system 200 is akin to the system 20 (FIG. 1) described above, with the delivery catheter 202 sized to slidably receive the capture assembly 204, the fastener delivery assembly 206 and the surgical fastener 26. The capture assembly 204 forms or provides a capture body 210 that is otherwise transitionable from the normal arrangement illustrated in FIG. 20 to a collapsed arrangement within the delivery catheter 202. Features provided with the delivery catheter 202 facilitate transitioning of the capture body 210 to a deflected arrangement when retracted into the delivery catheter 202. The guide sheath 208 is slidably disposed within the capture assembly 204, and guides deployment of the surgical fastener 26 with manipulation of other components of the fastener delivery assembly 206 (such as the push tube 140 (FIG. 1) and the tether 142 (FIG. 1) described above). As with the system 20 of FIG. 1, the system 200 provides a delivery state in which the capture body 210, the fastener delivery assembly 206, and the surgical fastener 26 are retained within the delivery catheter 202 for percutaneous delivery to a target site (such as a mitral valve target site). In a chordae capture state, at least a portion of the capture body 210 is deployed from the delivery catheter 202, self-transitions to the normal arrangement shown, and can be manipulated to capture or engage chordae at a mitral valve target site. In a deployment state, the guide sheath 208 guides deployment and release of the surgical fastener 26 from the delivery catheter 202. Finally, in a retracted state, the surgical fastener 26 remains deployed from the delivery catheter 202, and the capture body 210 is retracted back within the delivery catheter 202.

Figure 21:
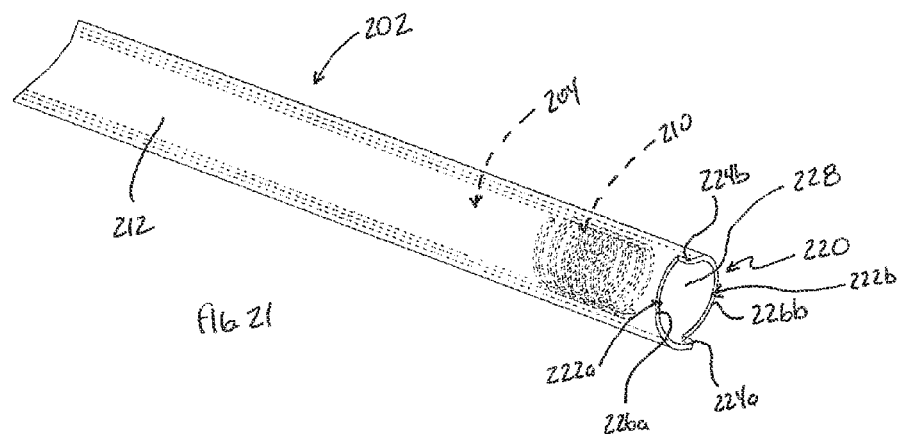
FIG. 21 is an enlarged perspective view of a portion of the system of FIG. 20, illustrating a delivery catheter component thereof.

The delivery catheter 202 can assume a variety of forms conventionally employed for atraumatic traversal of a patient's vasculature. As with previous embodiments, a distal section 212 of the delivery catheter 202 can be formed of stainless steel or other more rigid material (as compared to a remainder of the catheter 202), and optionally is separately formed and permanently attached to a steerable catheter (not shown). Regardless, and as best shown in FIG. 21, the distal section 212 terminates at a distal tip 220 that is cut or otherwise formed to define two tapered notches 222a, 222b. The notches 222a, 222b extend circumferentially from one another along the distal tip 220, creating first and second shoulders 224a, 224b. First and second ramp surfaces 226a, 226b taper proximally toward the corresponding shoulder 224a, 224b (i.e., the first ramp surface 226a tapers proximally from the first shoulder 224a to the second shoulder 224b). As described below, the notches 222a, 222b are configured to engage and collapse corresponding features of the capture body 210 (FIG. 20). Finally, the delivery catheter 202 forms a lumen 228 sized to slidably receive other components of the system 200 (FIG. 20) as described below.

Figure 22A:
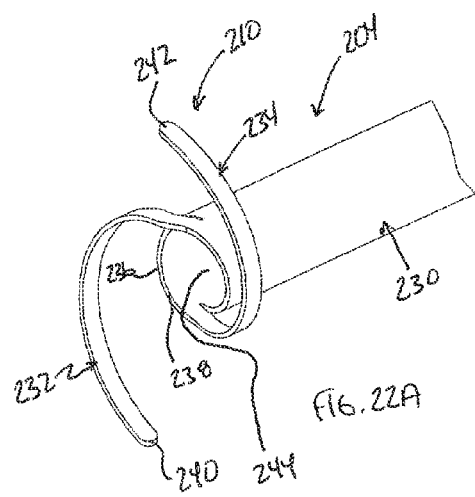
FIG. 22A is a perspective view of a portion of a capture assembly useful with the system of FIG. 20.

As shown in FIG. 22A, the capture assembly 204 includes the capture body 210 and a tube 230. The capture body 210 can be akin to the capture body 24 (FIG. 1) described above, and includes a first leg or prong 232 and a second leg or prong 234. In the normal arrangement of FIG. 22A, the legs 232, 234 project outwardly relative to a perimeter 236 defined a distal end 238 of the tube 230, with the first leg 232 terminating at a tip 240, and the second leg 234 terminating a tip 242. In this regard, the legs 232, 234 extend in or with an identical wind direction, such that the capture body 210 has, in some embodiments, a hurricane-like or spiral shape in the normal arrangement. Various shape and wind direction features described above with respect to the capture body 24 of FIG. 1 are equally applicable to the capture body 210.

The tube 230 forms a lumen 244 sized to receive one or more other components of the system 200 (FIG. 20) as described below. An outer diameter of the tube 230 is less than a diameter of the delivery catheter lumen 228 (FIG. 21). Further, the tube 230 is flexible, and in some constructions is formed of a robust shape memory material (e.g., Nitinol™) for reasons made clear below.

Figure 22B:
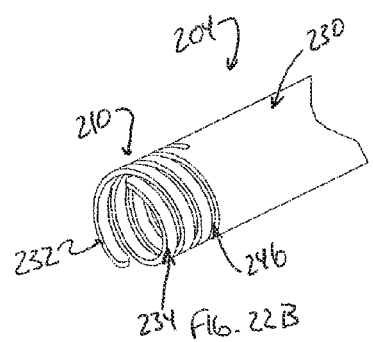
FIG. 22B is a perspective view of the capture assembly of FIG. 22A in a collapsed arrangement.

The capture assembly 204 can be a homogenous component, with the capture body 210 being integrally formed with or by the tube 230. For example, and with additional reference to FIG. 22B, the capture assembly 204 can be formed by initially providing the tube 230 as a continuous body, and then cutting a double helix pattern 246 at an end thereof, resulting in the spiral shape shown in FIG. 22B. The double helix cut pattern 246 thus generates the legs 232, 234 of the capture body 210, with the legs 232, 234 naturally assuming the expanded, normal arrangement of FIG. 22A. When subjected to an external radially compressive force, the legs 232, 234 can be forced to the collapsed arrangement of FIG. 22B. Upon removal of this force, the legs 232, 234 self-revert from the collapsed arrangement of FIG. 22B back to or toward the normal arrangement of FIG. 22A.

Returning to FIG. 20, the guide sheath 208 component of the fastener delivery assembly 206 is formed of a robust yet flexible material and has a generally square shape in transverse cross-section along a length thereof or just at the distal tip (with a smooth transition from round to square). The guide sheath 208 terminates at a distal end 250 and has an outer dimension sized to be slidably received within the capture assembly lumen 244. The guide sheath 208 forms a lumen 252 open at the distal end 252, and having the square shape shown. The guide sheath 208 extends through a length of the capture assembly 204 and the delivery catheter 202, and can be longitudinally advanced distally beyond the capture body 210 and the catheter distal tip 220 as shown, and proximally retracted within the components 202, 204. Regardless, the guide sheath lumen 252 is sized to slidably receive the surgical fastener 26 and other components of the fastener delivery assembly 206 (such as the push tube 140 and the tether 142 of FIG. 1) commensurate with previous descriptions. In general terms, then, the guide sheath lumen 252 is configured to constrain the surgical fastener 26 in a deflected arrangement when the surgical fastener 26 is disposed therein.

Use of the repair system 200 in performing a surgical procedure, such as percutaneous repair of a defective mitral valve, is highly similar to the descriptions provided above with respect to the repair system 20 (FIG. 1). In an initial delivery state generally reflected in FIG. 21, the capture assembly 204 is arranged such that the capture body 210 is disposed within the delivery catheter 202 (proximal the distal tip 220). In this arrangement, the capture body 210 is constrained to the collapsed arrangement generally illustrated in FIG. 21. Though not shown in FIG. 21, the guide sheath 208 (FIG. 20) is retracted within the capture assembly 204, and the surgical fastener 26 (FIG. 20) is retracted within the guide sheath 208.

As with previous embodiments, with the system 200 in the delivery state, one procedure in accordance with principles of the present disclosure entails the delivery catheter distal section 212 being percutaneously guided (e.g., via the femoral vein) into the right atrium, across the atrial septum, and into the left atrium. Once inside the left atrium, the capture assembly 204 is distally advanced relative to the delivery catheter 202 to deploy the capture body 210 from the distal tip 220 as shown in FIG. 23A. The system 200 is then manipulated to guide the deployed capture body 210 to a location near the center of the mitral valve. If desired, the capture assembly 204 can be further distally advanced relative to the delivery catheter 202, positioning the capture body 210 into the left ventricle. Once in the left ventricle, the capture body 210 is rotated (by rotating the capture assembly tube 230) such that the legs 232, 234 capture chordae from opposing leaflets as previously described. As desired, the capture body 210 can be rotated in the opposite direction, retracted and/or repositioned in order to achieve an optimal placement of the capture body 210 relative to the chordae.

After chordae is captured, the guide sheath 208 is distally advanced relative to the capture assembly 204 so as to locate the distal end 250 distal the capture body 210 as shown in FIG. 23B. As a point of reference, in the arrangement of FIG. 23B, the surgical fastener 26 (FIG. 20) remains within the confines of the guide sheath 208. Subsequently, the surgical fastener 26 is distally advanced and deployed from the distal end 250 of the guide sheath 208 as shown in FIGS. 23C and 23D. Similar to previous embodiments, as the surgical fastener 26 is directed beyond the distal end 250 of the guide sheath 208, the clips 110-116 substantially freely transition toward the undeflected arrangement with minimal interference from the capture body 210. In the deployed arrangement of FIG. 23D, one or more of the clips 110-116 engage captured tissue.

With the surgical fastener 26 in the partial clip deployment state, the delivery catheter 202 is distally advanced toward the capture body 210 (and thus the captured tissue) as shown in FIG. 23E. If necessary, the delivery catheter 202 is rotated relative to the capture body 210, bringing the legs 232, 234 into engagement with a respective one of the notches 222a, 222b. As a point of reference, FIG. 23F illustrates the same arrangement of FIG. 23E but with the surgical fastener 26 removed from the view to more clearly show engagement between the distal tip 220 and the capture body 210. The first leg 232 nests along the first ramp surface 226a, and bears against the second shoulder 224b. A similar relationship is provided between the second leg 234 and the distal tip 220. The capture body 210 is then rotated and proximally retracted relative to the delivery catheter 202, forcing the legs 232, 234 back toward the deflected arrangement and retracting the capture body 210 back within the delivery catheter 202 as shown in FIG. 23G. As a point of reference, the direction of rotation of the capture body 210 is opposite a "direction" of the notches 222a, 222b (best shown in FIG. 21) and opposite the rotational direction utilized when capturing chordae with the legs 232, 234. Thus, the legs 232, 234 are easily guided back into the delivery catheter 202 (via abutting interface with the shoulders 224a, 224b) without disturbing the captured tissue.

A relationship of the partially deployed surgical fastener 26 relative to the mitral valve is then performed (e.g., echocardiogram, fluoroscopy, etc.) to evaluate whether the leaflets are fastened to or captured by the surgical fastener 26 as described above. If the clinician is unsatisfied with the placement, the surgical fastener 26 can be retracted back into the delivery catheter 202 and the chordae capturing and surgical fastener placement procedures as described above are repeated. Once the clinician determines that the surgical fastener 26 is properly located, the surgical fastener 26 is then fully released from a remainder of the system as described above (e.g., the tether 142 (FIG. 1) is unthreaded from the surgical fastener 26).

Portions of another embodiment repair system 300 in accordance with principles of the present disclosure is shown in FIG. 24. The system 300 is akin to the systems 20 (FIG. 1) and 200 (FIG. 20) described above, and generally includes a delivery catheter 302, a capture assembly 304, first and second surgical fasteners 306, 308 and a fastener delivery assembly 310 (referenced generally). As with previous embodiments, the capture assembly 304 forms or provides a capture body 312 that is configured to be slidably received within the delivery catheter 302, transitionable from the normal arrangement illustrated in FIG. 24 to a collapsed arrangement within the delivery catheter 302. Similarly, the surgical fasteners 306, 308 are transitionable from the undeflected arrangement shown in FIG. 24 to a deflected arrangement within the delivery catheter 302 (and vice-versa) via operation of the fastener delivery assembly 310. In a delivery state of the system 300, the capture body 312 and the surgical fasteners 306, 308 are retained within the catheter 302 for percutaneous delivery to a mitral valve target site. In a chordae capture state of the system 300, the capture body 312 is deployed from the delivery catheter 302, self-transitions to the normal arrangement shown, and can be manipulated to capture or engage chordae at the mitral valve target. In a release state, the surgical fasteners 306, 308 are deployed from the catheter 302, self-reverting to the undeflected arrangement shown to capture or fasten opposing leaflets of the mitral valve target site to one another. Optionally, the system 300 can incorporate additional components, such as a handle assembly (not shown) configured to assist in user manipulation of the delivery catheter 302, the capture assembly 304, and/or the fastener delivery assembly 310.

Figure 25:
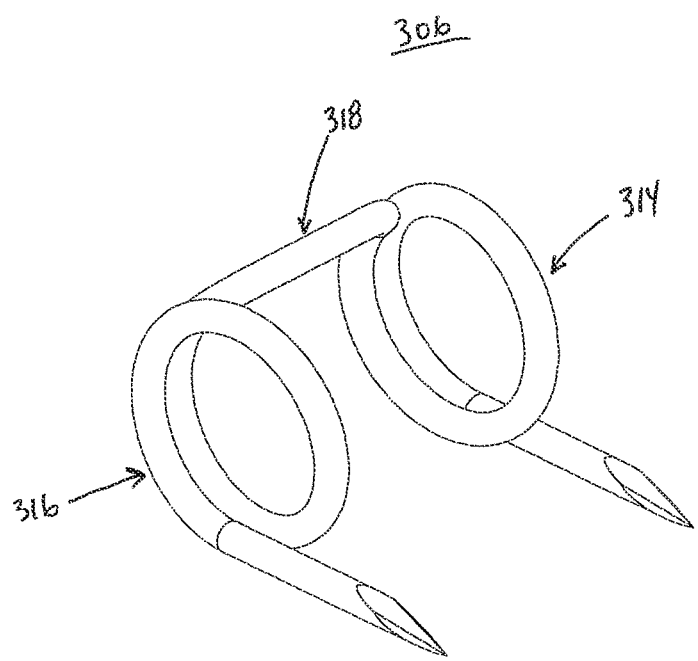
FIG. 25 is an enlarged perspective view of a surgical fastener useful with the system of FIG. 24.

As reflected by FIG. 24, the surgical fasteners 306, 308 are akin to the bridge-type surgical fastener 26' (FIG. 5) described above. The surgical fasteners 306, 308 can be identical, with FIG. 25 illustrating the first surgical fastener 306 in greater detail. The surgical fastener 306 includes two self-closing clips 314, 316 as previously described (shown in the undeflected arrangement) interconnected by a base member 318. As with previous embodiments, the clips 314, 316 naturally assume a loop shape in the normal arrangement (e.g., due to a memory set shape characteristic), and can be rendered substantially straight or linear (e.g., the loop(s) is no longer discernable) in a deflected arrangement. Upon removal of the deflection force, the clips 314, 316 self-transition or revert back to the memory set loop shape of the undeflected arrangement.

Returning to FIG. 24, the delivery catheter 302 can assume a variety of forms conventionally employed for atraumatic traversal of a patient's vasculature, and generally defines a distal section 320 terminating at a distal tip 322. In some embodiments, the distal section 320 can be formed of a more rigid material (e.g., stainless steel or a rigid plastic) as compared to a remainder of the delivery catheter 302. The delivery catheter 302 can incorporate various known features to effectuate user-controlled steering of the distal section 320. For example, the distal section 320 can be separately formed and subsequently affixed to a more conventional catheter, such as a steerable catheter.

The distal section 320 is configured to receive and constrain the surgical fasteners 306, 308 and the capture assembly 304. For example, and as best shown in FIG. 26A, the distal section 320 forms a central lumen 328, and first and second shaped fastener slots 330, 332. The central lumen 328 is located between the opposing fastener slots 330, 332, and is configured to slidably retain the capture assembly 304 (FIG. 24) as described below. The slots 330, 332 are sized and shaped to receive a respective one of the surgical fasteners 306, 308 (FIG. 24), each having an elongated shape in a direction transverse to a central axis of the delivery catheter 302, defining a central region 336 and opposing side regions 338, 340 (identified for the first slot 330 in FIG. 26A). The so-shaped slots 330, 332 can be formed along an entire length of the delivery catheter 302. In other embodiments, however, the shaped slots 330, 332 are defined only along the distal section 320, with a remainder of the delivery catheter 302 having a less complex lumen shape. For example, as shown in FIG. 26B, the delivery catheter 302 can form, at locations proximal the distal section 320 (FIG. 26A) opposing fastener lumens 342, 344. FIG. 26B further reflects the central lumen 328 as extending an entire length of the delivery catheter 302. The fastener lumens 342, 344 can have a relatively simple shape (e.g., circular in cross-section). Upon final assembly with the distal section 320 (FIG. 26A), the first slot 330 is open to the first fastener lumen 342, and the second slot 332 is open to the second fastener lumen 344 (e.g., the fastener lumens 342, 344 are axially aligned with the central region 336 (FIG. 26A) of the corresponding slot 330, 332).

Regardless, and with reference to FIG. 26C (otherwise illustrating a relationship between the first surgical fastener 306 and the first slot 330), a transverse length of the slot 330 is commensurate with a width of the surgical fastener 306 such that when the base member 318 is centered relative to the slot 330, the clips 314, 316 will nest within a respective one of the side regions 338, 340. Thus, as the surgical fastener 306 is inserted into the slot 330 and retracted proximally, the clips 314, 316 are forced toward the more straightened shape, sliding within the slot 330. The central region 336 is configured for slidably receiving a component of the fastener delivery assembly 310 (FIG. 24) otherwise employed to manipulate the surgical fastener 306 relative to the distal section 320 as described below. As shown in FIG. 26D, then, the fasteners 306, 308 can be slidably received within, and forced to the deflected arrangement by, a respective one of the slots 330, 332.

Wires or similar bodies can be slidably disposed within the fastener lumens 342 or 344 (FIG. 26B) and connected to a respective one of the surgical fasteners 306, 308 otherwise held within the corresponding slot 330 or 332. In some constructions, the fastener delivery assembly 310 (FIG. 24) consists of solid rods for distally advancing the surgical fasteners 306, 308. More particularly, a first rod (not shown) is slidably disposed within the first fastener lumen 342 and a second rod (not shown) is slidably disposed within the second fastener lumen 344. Following insertion of the surgical fasteners 306, 308 into the slots 330, 332, respectively, a distal end of the first rod bears against the base member 318 (FIG. 25) of the first fastener 306, whereas the second rod bears against the loaded second fastener 308. The surgical fasteners 306, 308 can then be deployed from the distal section 320 by simply advancing the corresponding rod. This approach may not facilitate retraction of the surgical fasteners 306, 308 following partial deployment.

Figure 27A:
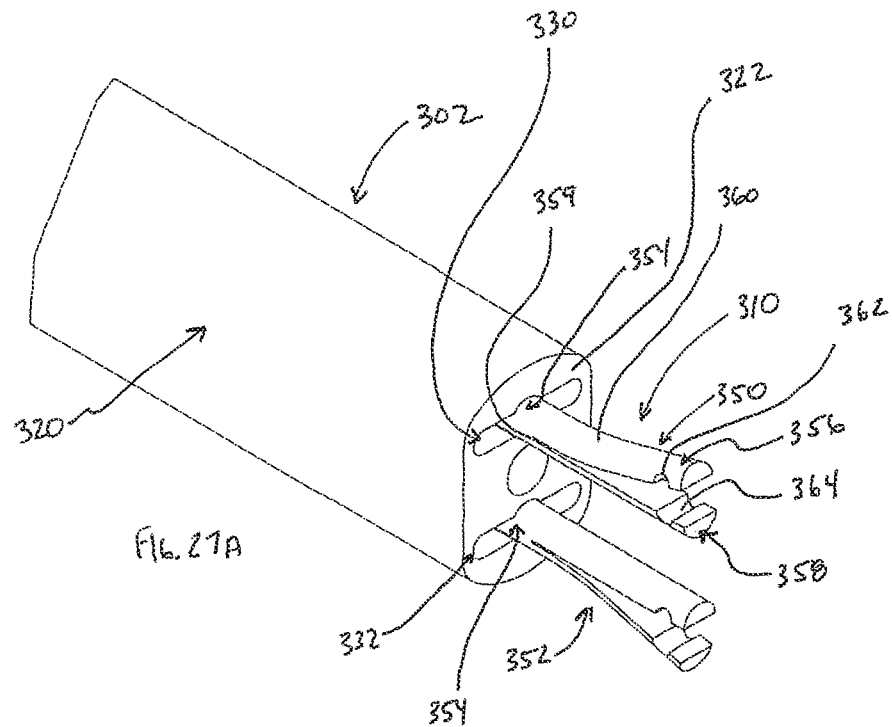
FIGS. 27A and 27B are enlarged, perspective views illustrating portions of a fastener delivery assembly useful with the system of FIG. 24.
Figure 27B:
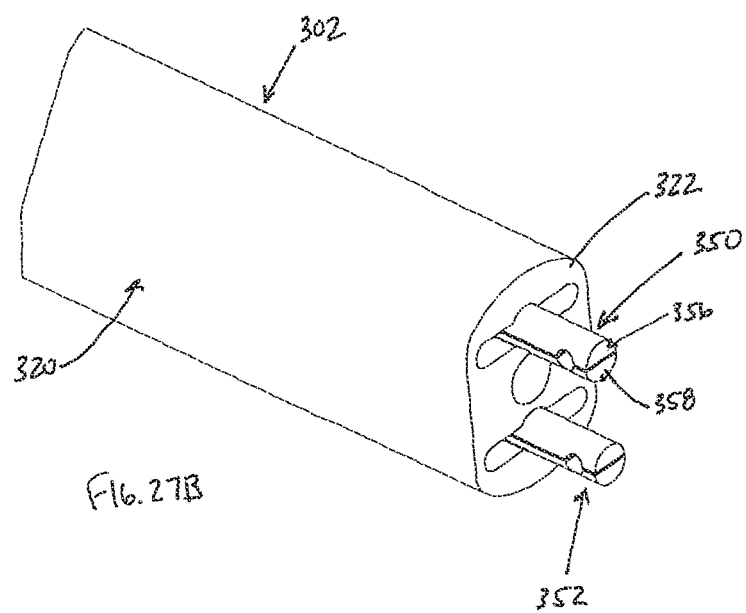

Alternatively, FIGS. 27A and 27B illustrate another embodiment of the fastener delivery assembly 310 that includes first and second push rod mechanisms 350, 352. The push rod mechanisms 350, 352 can be identical, and each consists of a metal (e.g., Nitinol) wire or rod 354 cut to define opposing arms 356, 358 at a distal region 360 thereof. FIG. 27A illustrates the arms 356, 358 in a natural arrangement in which the arms 356, 358 naturally assume a distally splayed-apart relationship, effectively pivoting or splaying from one another at a hinge point 359. A transverse slot 362, 364 is formed in each arm 356, 358, respectively; the slots 362, 364 and are collectively sized to receive and capture the base member 318 (FIG. 25) of a corresponding one of the surgical fasteners 306, 308 (FIG. 24). Upon final assembly, the rod 354 of the first push rod mechanism 350 is disposed within the first slot 330, and extends an entire length of the delivery catheter 302 (via the first fastener lumen 342 (FIG. 26B)). The rod 354 of the second push rod mechanism 352 is similarly arranged within the second slot 332. As the rods 354 are proximally retracted within the corresponding slot 330, 332 to locate the corresponding hinge point 359 proximal the catheter distal tip 322, the opposing arms 356, 358 are forced toward one another, as reflected in FIG. 27B. Subsequently, with distal advancement of the rods 354 (i.e., transitioning from the arrangement of FIG. 27B back to the arrangement of FIG. 27A in which the hinge point 359 of the respective rods 354 is distal the catheter distal tip 322), the arms 356, 358 naturally splay apart.

Figure 28A:
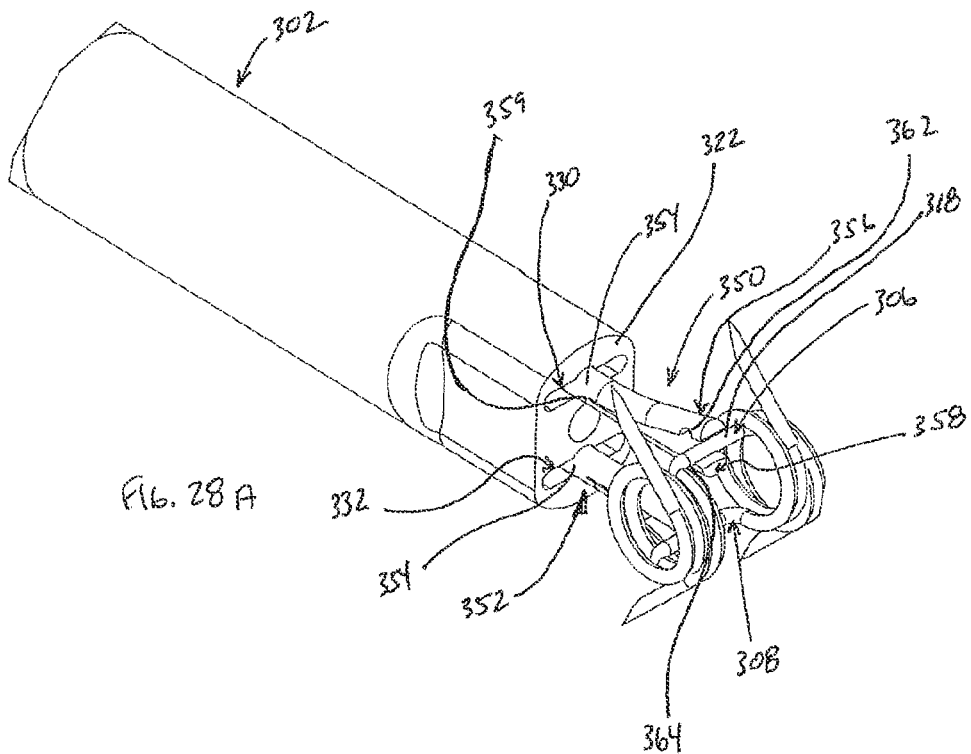
FIGS. 28A and 28B illustrate connection of the fastener delivery assembly components of FIGS. 27A and 27B with the surgical fasteners of FIG. 25.
Figure 28B:
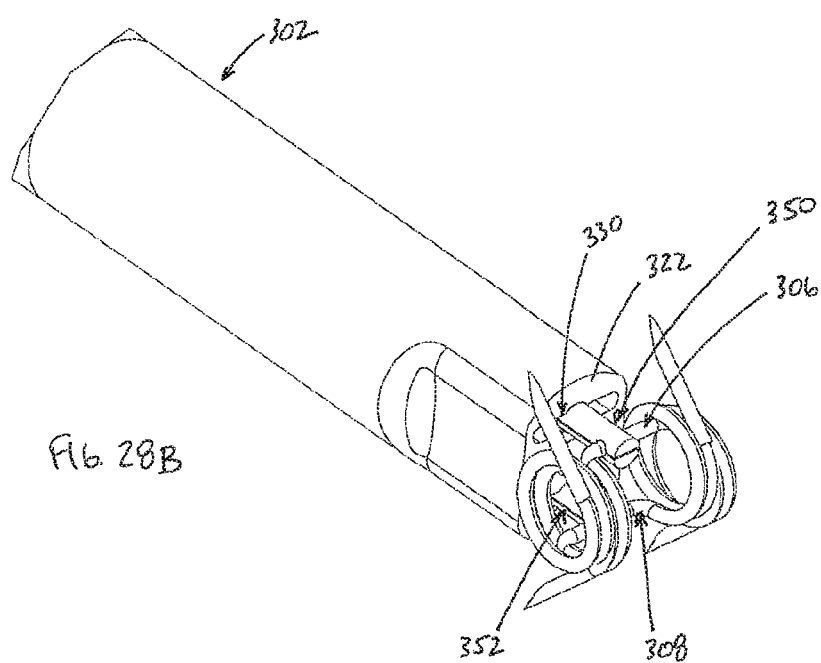

With reference to FIGS. 28A and 28B, the push rod mechanisms 350, 352 interface with a respective one of the surgical fasteners 306, 308 as follows. To effectuate loading of the surgical fasteners 306, 308, the corresponding rod 354 is distally advanced from the delivery catheter tip 322 to the arrangement of FIG. 28A. The first surgical fastener 306 is aligned with the first push rod mechanism 350, and the second surgical fastener 308 is aligned with the second push rod mechanism 352. With the arms 356, 358 naturally assuming the splayed-apart arrangement, the base member 318 is located within the transverse slots 362, 364 of the corresponding push rod mechanism 350, 352 (best visible in FIG. 28A for the first surgical fastener 306 and the first push rod mechanism 350), and the rods 354 proximally retracted. Pulling the rod 354 into the corresponding slot 330, 332 causes the arms 356, 358 to come together, thereby capturing the base member 318 of the surgical fastener 306, 308 as shown in FIG. 28B. With further proximal retraction of the push rod mechanisms 350, 352, the corresponding surgical fastener 306, 308 is pulled back into the corresponding slot 330, 332 as described above. Subsequent deployment of the surgical fasteners 306, 308 entails distal advancement of the corresponding rod mechanisms 350, 352 (i.e., to the arrangement of FIG. 28A). With the construction of FIGS. 28A and 28B, the surgical fasteners 306, 308 can be retracted and redeployed unless the corresponding rod 354 is pushed to the point where the arms 356, 358 split apart (i.e., the hinge point 359 is distal the catheter distal tip 322 as in FIG. 28A), at which point the corresponding surgical fastener 306, 308 is fully released.

Returning to FIG. 24, the capture assembly 304 includes the capture body 312 as mentioned above and is highly akin to the construction of FIG. 3F described above. In general terms, then, the capture body 310 forms opposing legs 370, 372 extending from a shaft 374. Extension of the legs 370, 372 defines a common wind direction, with the shaft 374 sized to be slidably received within the central lumen 328 (FIG. 26A).

Figure 29A:
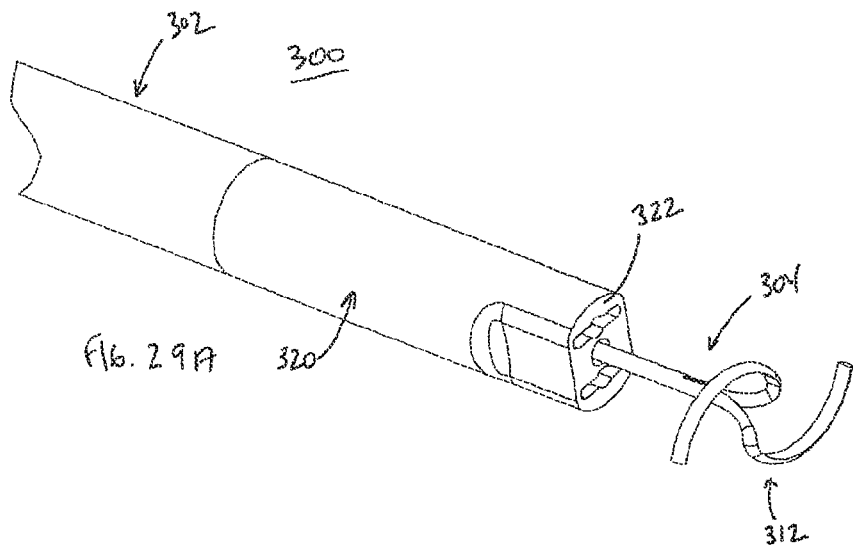

Regardless of an exact construction, use of the system 300 in repairing a mitral valve is akin to previous descriptions, and begins with the system 300 in a delivery state as reflected in FIG. 26A. In the delivery state, the delivery catheter 302 retains various other components of the system 300 (e.g., the surgical fasteners 306, 308 (FIG. 24) and the capture body 312 (FIG. 24)). The distal section 320 is then inserted through a femoral access point and percutaneously navigated across the atrial septum and into the left atrium. The capture body 312 is then deployed as shown in FIG. 29A inside the left atrium and advanced across the mitral valve and into the left ventricle. Alternatively, the capture body 312 can be deployed from the delivery catheter distal section 320 after the distal tip 322 is advanced into the left ventricle. Regardless, once inside the left ventricle, the capture body 312 is rotated such that it captures chordae just below the leaflets and pulls them together so the anterior and posterior leaflets are contacting each other.

Figure 29B:
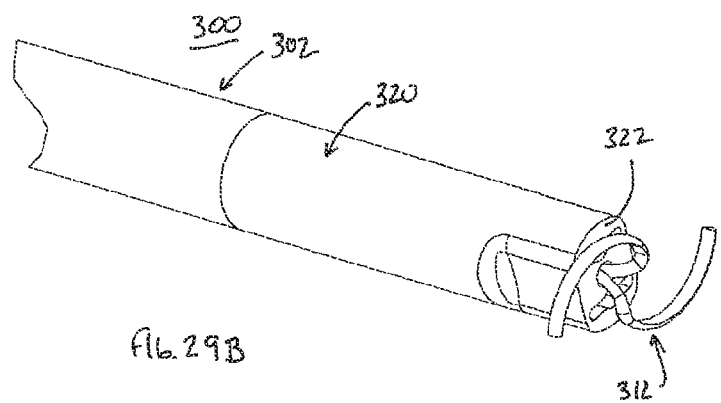

The distal tip 322 of the delivery catheter 302 is then distally advanced up to a location near the capture body 31 as shown in FIG. 29B. The leaflet and chordae tissue is thus captured between the capture body 312 and the distal tip 322.

Figure 29C:
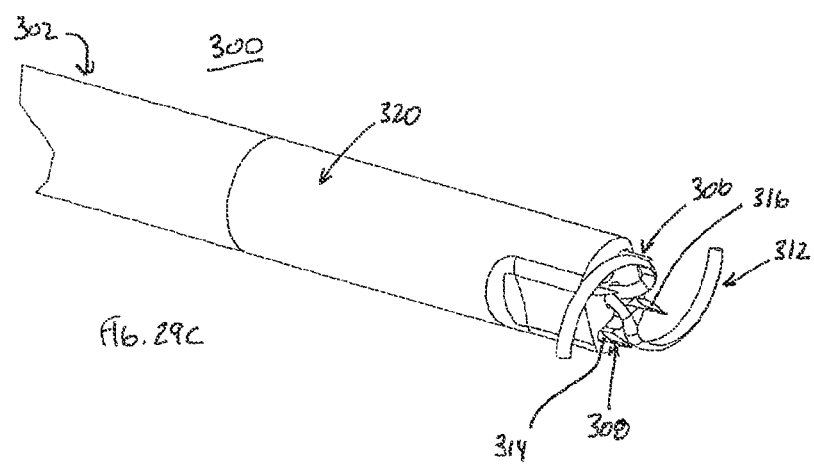

With reference to FIGS. 29C and 29D, the surgical fasteners 306, 308 are partially deployed either simultaneously or sequentially from the delivery catheter 302 via manipulation of the fastener delivery assembly 310 (FIG. 24) as described above. As the clips 314, 316 exit the distal tip 322, they engage the tissue surrounding the capture body 312, thereby capturing the leaflets.

After the surgical fasteners 306, 308 are partially deployed, the distal tip 322 of the delivery catheter 302 is left in contact with the leaflets, and the capture body 312 is retracted relative to the delivery catheter 302 as shown in FIG. 29E. Once the capture body 312 is retracted, placement and location of the surgical fasteners 306, 308 relative to the leaflets can be evaluated. If desired, the surgical fasteners 306, 308 can be retracted and relocated. Once satisfactory placement of the surgical fasteners 306, 308 is achieved, the surgical fasteners 306, 308 are released from the fastener delivery assembly 310 as shown in FIG. 29F and the delivery catheter 302 removed from the patient.

Another embodiment repair system 400 in accordance with principles of the present disclosure is shown in FIG. 30. The system includes a delivery catheter 402, a capture assembly 404, a surgical fastener 406, a fastener delivery assembly 408, and a handle 410. Details on the various components are provided below. In general terms, however, the system 400 is akin to the repair systems described above, with the capture assembly 404 including a capture body 412 that is transitionable from the normal arrangement illustrated in FIG. 30 to a collapsed arrangement within the delivery catheter 402. The surgical fastener 406 has a helix-type configuration as described below, and is selectively connected to the fastener delivery assembly 408 that otherwise effectuates manipulation of the surgical fastener 406 relative to the delivery catheter 402. The handle 410 operatively retains the capture assembly 404 and the fastener delivery assembly 408 relative to the delivery catheter 402. In a delivery state of the system 400, the capture body 412 and the surgical fastener 406 are retained within the delivery catheter 402 for percutaneous delivery to a mitral valve target site. In a chordae capture state of the system 400, at least a portion of the capture body 412 is deployed from the delivery catheter 402, self-transitioned to the normal arrangement shown, and can be manipulated to capture or engage chordae at the mitral valve target site. In a release state, the surgical fastener 406 is deployed from the delivery catheter 402 and released from the fastener delivery assembly 408, self-reverting to the undeflected arrangement shown to capture or fasten opposing leaflets of the mitral valve target site to one another.

The delivery catheter 402 can assume any of the forms previously described for atraumatic traversal of a patient's vasculature. The delivery catheter 402 generally defines a proximal section 416 terminating at a proximal end 418, and a distal section 420 terminating at a distal end 422. As with previous embodiments, the distal section 420 can have a more rigid or robust construction as compared to a remainder of the catheter 402 to better force and maintain the capture body 412 and/or the surgical fastener 406 in the collapsed or deflected states, respectively. The delivery catheter 402 optionally incorporates one or more steering features that aide in steering the distal end 422 to the proper location at the target site (e.g., mitral valve). In this regard, the proximal end 418 is attached to a deflection mechanism 424 (referenced generally) otherwise maintained by the handle 410. The deflection mechanism 424 includes a deflection knob 426 that, when rotated relative to a remainder of the handle 410, effectuates deflection of the distal section 420/distal end 422 relative to the proximal section 416.

The capture assembly 404, including the capture body 412, is generally akin to any of the embodiments previously described. For example, and as shown in FIGS. 31A-31C, the capture assembly 404 includes the capture body 412, a shaft 430, a retention sheath 432, and a locking assembly 434. As a point of reference, FIG. 31A illustrates a chordae capture arrangement in which the capture body 412 and the retention sheath 432 are advanced distal the catheter distal end 422. In the delivery state of FIG. 31C, the capture body 412 and the retention sheath 432 are retracted within the delivery catheter 402, with portions of the shaft 430 and the retention sheath 432 being visible proximal the handle 410.

The capture body 412 can assume any of the forms previously described and include first and second legs 436, 438 projecting from the shaft 430, in or with an identical wind direction. Once again, the capture body 412 is formed of a robust shape memory material (e.g., Nitinol) so as to be deflectable or collapsible from the normal arrangement of FIGS. 31A and 31B to a collapsed arrangement, and self-revert from the collapsed arrangement back to or toward the normal arrangement upon removal of the collapsing force. The capture body 412 can be integrally formed with the shaft 430 (i.e., the shaft 430 and the capture body 412 are formed as a homogenous structure), or the capture body 412 can be separately formed and subsequently connected to the shaft 430. Regardless, the shaft 430 is sized to be slidably received within the retention sheath 432, and is of sufficient length such that a proximal end 440 thereof is located proximal the retention sheath 432. In some embodiments, an actuator (e.g., knob) 442 is formed by or attached to the proximal end 440. A user-applied rotational force onto the actuator 442 is transferred onto the shaft 430, and thus onto the capture body 412.

The retention sheath 432 is sufficiently flexible for traversing a patient's vasculature, and at least a distal segment 446 (best seen in FIG. 31B) thereof is sufficiently circumferentially rigid for retaining the capture body 412 in the collapsed arrangement (when the legs 436, 438 are disposed within the distal segment 446). The retention sheath 432 terminates at opposing, distal and proximal ends 448, 450, and is sized to be slidably received within the delivery catheter 402. Further, a length of the retention sheath 432 is sufficient to locate the proximal end 450 proximal the handle 410. In this regard, the locking assembly 434 is associated with the retention sheath 432 as well as the shaft 430 to effectuate selective locking of the components 430, 432 relative to one another. As best shown in FIG. 31C, the locking assembly 434 includes a coupling piece 452 and a locking knob 454. The coupling piece 452 is mounted to the proximal end 450 of the retention sheath 432. Though not visible in FIG. 31C, the coupling piece 452 forms a passage that is open to a lumen (not shown) of the retention sheath 432 and through which the shaft 432 is slidably received. Thus, the capture body 412 can be distally advanced and proximally retracted relative to the retention sheath 432 via a corresponding longitudinal movement of the actuator 442 relative to the coupling piece 452. The actuator 442 and the coupling piece 452 have corresponding, mating features that selectively lock the actuator 442 relative to the coupling piece 452 upon engagement between the two components 442, 452 (i.e., in the engaged relationship between the components 442, 452 of FIG. 31A, rotation of the coupling piece 452 is transferred to the capture body 412 via the actuator 442 and the shaft 430 (FIG. 31C)). The locking knob 454 is rotatably mounted to the handle 410 and includes various features (not shown) that selectively mate with corresponding features of the coupling piece 452. With this construction, upon engagement of the actuator 442/coupling piece 452 with the locking knob 454 and subsequent rotation of the locking knob 454 relative to the handle 410, the capture body 412 is spatially fixed relative to the handle 410 (and thus relative to the delivery catheter 402) via the shaft 430 and the coupling piece 452/locking knob 454 connection.

Returning to FIG. 30, the surgical fastener 406 is configured to slidably interface or receive the retention sheath 432. For example, one embodiment of the surgical fastener 406 is shown in greater detail in FIG. 32A, and includes or defines first and second clip arms 460, 462 and a base member 464. The clip arms 460, 462 extend from opposite sides of the base member 464, and have a helix shape, each terminating at a tip 466 (with the tip of the second clip arm 462 being hidden in the view). A pitch of each of the clip arms 460, 462 can be variable as shown, but in other embodiments can be constant. Further, other spacings and patterns differing from those reflected in FIG. 32A can be employed; however, the pitch needs to be large enough to allow some clearance about the capture body 412 (FIG. 30) for reasons made clear below. With the double helix design effectuated by the clip arms 460, 462, the surgical fastener 406 defines an open central axis or region (i.e., the clip arms 460, 462 spiral about (but are radially spaced from), a central axis of the fastener 406). As shown, the clip arm tips 466 are sharpened (e.g., needle points) for penetrating tissue.

The base member 464 can assume a variety of forms sufficient for interfacing with the fastener delivery assembly 408 (FIG. 30) as described below, and is configured to retain the "open" central region of the surgical fastener 406 as described above. For example, with the construction of FIG. 32A, the base member 464 includes opposing shoulder segments 467a, 467b, and a head segment 468. The shoulder segments 467a, 467b extending in a generally linear or straight fashion (e.g., substantially parallel with the central axis of the fastener 406) from opposite sides of the head segment 468, with each shoulder segment 467a, 467b leading to a respective one of the clip arms 460, 462. The head segment 468 has a circumferential curvature that displaces a structure of the base member 464 radially away from the central axis.

Figure 32A:
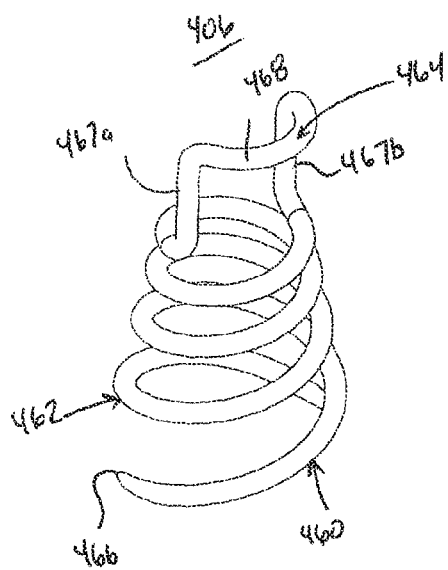
FIG. 32A is a perspective view of a surgical fastener useful with the system of FIG. 30.

In some embodiments, the surgical fastener 406 has a shape memory characteristic that imparts the tapered shape reflected in FIG. 32A (i.e., in the natural arrangement of FIG. 32A, a diameter of the surgical fastener 406 at the tips 466 is greater than a diameter defined at the base member 464). When subjected to a compressive force, the surgical fastener 406 readily deflects or collapses from the tapered shape, resulting in a relatively uniform diameter along a length of the surgical fastener 406. Upon removal of the compressive force, the surgical fastener 406, and in particular the clip arms 460, 462, naturally reverts to or toward the tapered shape shown. Optionally, the surgical fastener 406 can have a more uniform shape in the natural arrangement, as reflected by the alternative surgical fastener 406' of FIG. 32B.

Figure 32B:
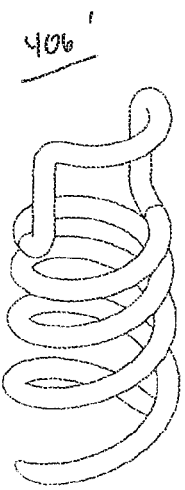
FIG. 32B is a perspective view of another surgical fastener useful with the system of FIG. 30.
Figure 32C:
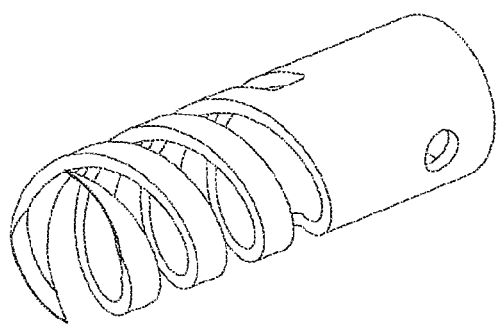
FIG. 32C illustrates manufacture of a surgical fastener useful with the system of FIG. 30.

The surgical fasteners 406, 406' of FIGS. 32A and 32B can be formed from a single wire as illustrated. Alternatively, a multi-helix clip can be formed from multiple wires attached to one another using a crimp sleeve, welding, adhesive, etc. In yet other embodiments, the double helix surgical fastener can be cut from a tube as generally reflected by FIG. 32C.

The surgical fastener 406 can incorporate one or more additional features. For example, the surgical fastener 406 can be made from a polymer instead of metal. The polymer could be water-absorbing (e.g., a hydrogel, high cross-link density polymer). The polymer can have a time delay before swelling, or could have a coating that breaks down in a given time followed by swelling. The delay in swelling would serve to prevent the surgical fastener 406 from experiencing premature shape change (e.g., before the surgical fastener 406 is fully delivered). Further, the swelling helps lock in the captured tissue. Further, with the coated polymer construction, the surgical fastener 406 will be substantially free of rough edges that might otherwise tend to cut or tear leaflet material. Basically, the surgical fastener 406 will turn into a blob, engulfing the tissue it acquires from the helix shape. Even further, the polymer used for the surgical fastener 406 could be a pharmacologic carrier, for example a drug that can improve healing. Even further, the polymer can be formulated to create heat (e.g., exothermic reaction). This localized heating could promote tissue adhesion via tissue welding. Effectively, then, the generated heat changes the collagen structure, and thus serves to partially or completely weld the leaflets together. Even further, the surgical fastener 406 can be configured to provide temporary "tacking" to allow adequate scaring/healing. Finally, the polymer could biodegrade over time.

Figures 33A, 33B:
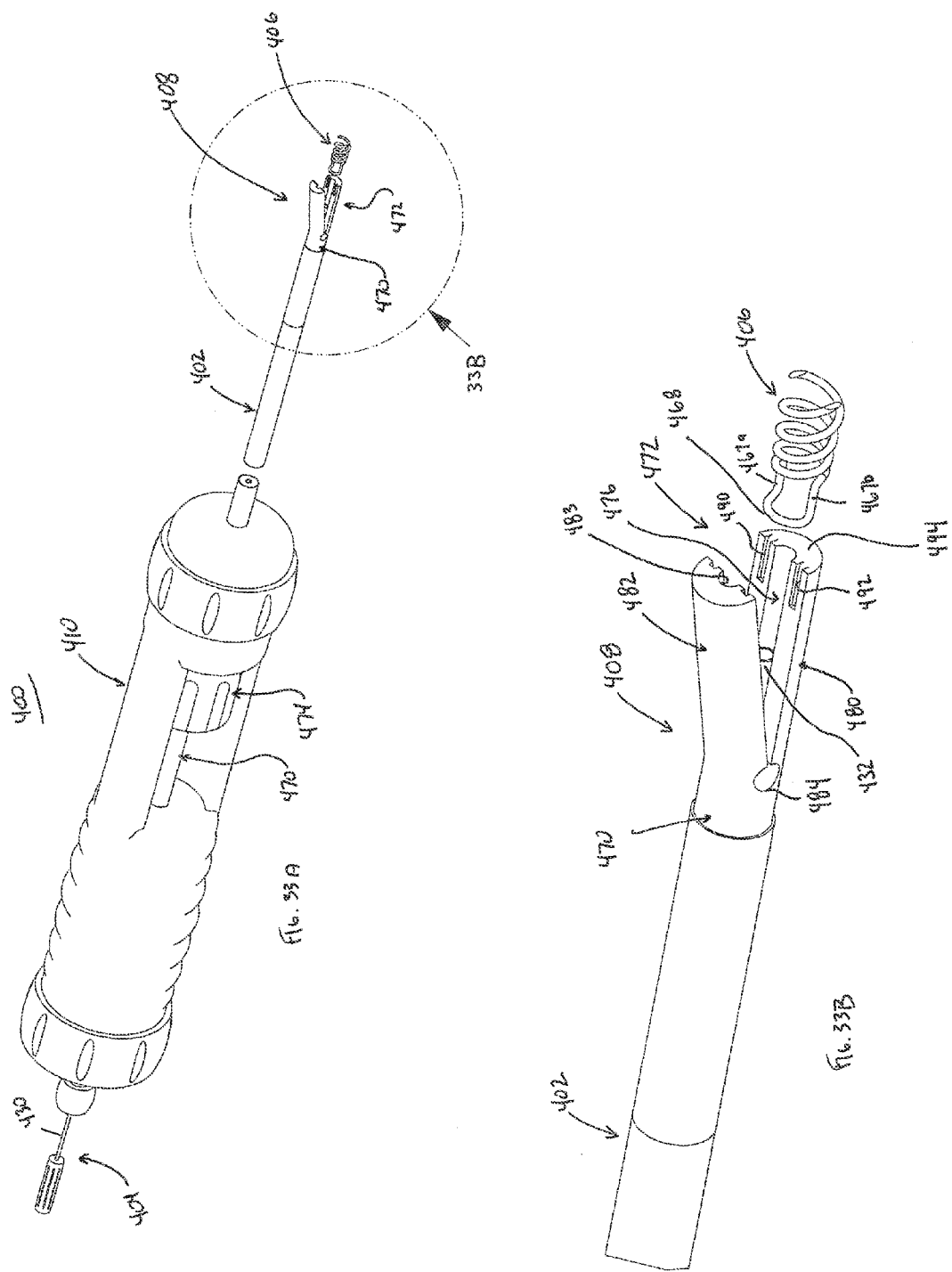
FIG. 33A is a perspective view of the system of FIG. 30, and illustrating a fastener delivery assembly component thereof.
FIG. 33B is an enlarged view of a distal portion of the FIG. 33A along section line 33B.

With reference to FIGS. 33A and 33B, the fastener delivery assembly 408 includes a tube 470, an anchor mechanism 472, and an actuator hub 474. The tube 470 is sized to be slidably received within the delivery catheter 402. Further, the tube 470 forms a lumen 476 (generally identified in FIG. 33B) sized to slidably receive the retention sheath 432 (and thus the shaft 430 of the capture assembly 404). The anchoring mechanism 472 is described in grater detail below, and is formed by or assembled to a distal region of the tube 470. Conversely, the hub 474 is mounted to a proximal region of the tube 470 and is movably retained by the handle 410. With this construction, movement of the actuator hub 474 relative to the handle 410, and thus relative to the delivery catheter 402, effectuates a corresponding movement of the anchoring mechanism 472 relative to the delivery catheter 402.

The anchoring mechanism 472 is configured to selectively maintain the surgical fastener 406, and in some constructions includes first and second jaws 480, 482. The jaws 480, 482 can be generally identical, and in some embodiments are integrally formed by the tube 470. For example, FIGS. 33A and 33B illustrate the tube 470 being cut or split at a distal region thereof to form the jaws 480, 482. With this construction, the lumen 476 formed by the tube 470 is effectively continued along the jaws 480, 482 as best shown in FIG. 33B. The jaws 480, 482 thus each define a longitudinal groove 483 (identified in FIG. 33B for the second jaw 482) that is one-half of the lumen 476. As a point of reference, FIG. 33B further illustrates the retention sheath 432 disposed within the lumen 476. In other embodiments, the anchoring mechanism 472 can be separately formed from and subsequently assembled to the tube 470.

Regardless of an exact construction, the jaws 480, 482 are pivotally connected to one another at a pivot point 484. With embodiments in which the anchoring mechanism 472 is integrally formed by the tube 470, the pivot point 484 is effectively defined as a living hinge, with the jaws 480, 482 naturally assuming the distally splayed arrangement. In the presence of a compressive force, the jaws 480, 482 can be forced toward one another, pivoting at the pivot point 484. Upon removal of the compressive force, the jaws 480, 482 self-transition back to or toward the splayed apart, normal arrangement of FIG. 33B.

The jaws 480, 482 each form one or more slots sized and shaped to receive corresponding feature(s) of the surgical fastener 406. For example, and as identified for the first jaw 480 in FIG. 33B, first and second slots 490, 492 are formed, extending from (and open relative to) a distal end 494 of the jaw 480. The slots 490, 492 correspond with the shoulder segments 467a, 467b of the fastener 406 (e.g., a transverse spacing between the slots 490, 492 corresponds with a transverse spacing between the shoulder segments 467a, 467b, and a radius (or other width dimension) of the slots 490, 492 approximates a radius (or other width dimension) of the shoulder segments 467a, 467b). Similar slots are formed in the second jaw 482. Though hidden in the view of FIG. 33B, a transverse groove is further formed in the second jaw 482, corresponding in size and shape with the head segment 468 of the surgical fastener 406.

Figure 34A:
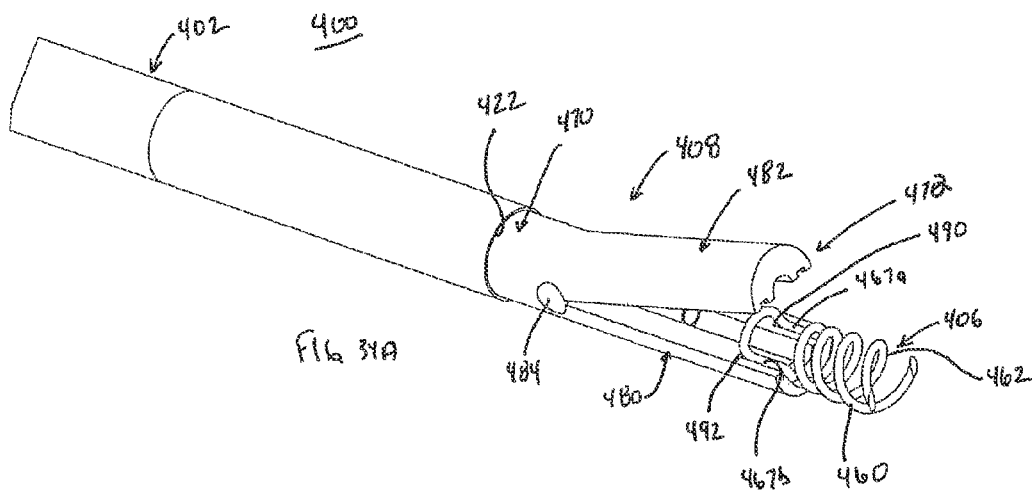
FIGS. 34A-34C illustrate loading of the surgical fastener of FIG. 32A to the fastener delivery assembly of FIG. 33B.
Figure 34B:
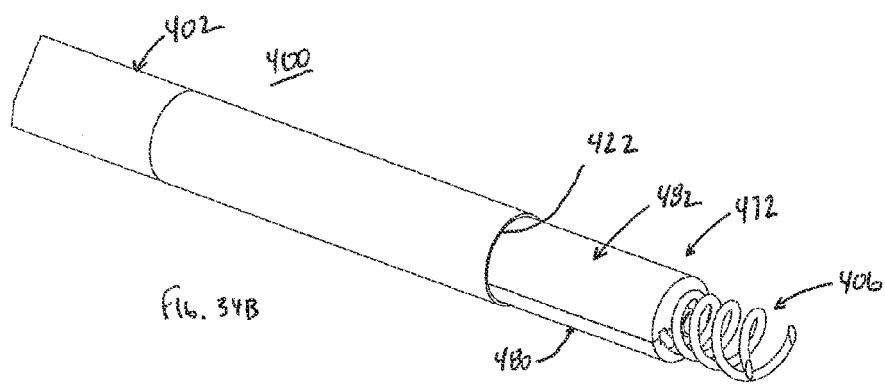
Figure 34C:
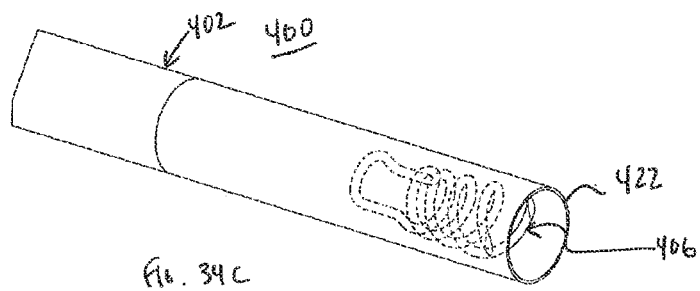

Operation of the fastener delivery assembly 408, and in particular the anchoring mechanism 472, in selectively engaging the surgical fastener 406 is shown in FIGS. 34A-34C. To load the fastener 406, the tube 470 is distally advanced relative to the delivery catheter 402 to the arrangement of FIG. 34A in which the hinge point 484 is distal the catheter distal end 422. Once free of the confines of the delivery catheter 402, the jaws 480, 482 naturally pivot away from one another. The surgical fastener 406 is then placed into one of the jaws 480, 482. For example, FIG. 34A illustrates the surgical fastener 406 nested with the first jaw 480, including the shoulder segments 467a, 467b located within a respective one of the slots 490, 492. The clip arms 460, 462 extend distal the distal end 494 of the first jaw 480.

The tube 470, and thus the anchoring mechanism 472, is then proximally retracted relative to the delivery catheter 402 until the hinge point 484 is proximal the catheter distal end 422. In the arrangement of FIG. 34B, then, the delivery catheter 402 forces the jaws 480, 482 toward one another, thereby capturing the surgical fastener 406 between the jaws 480, 482. Though hidden in the views, the second jaw 482 includes features (e.g., a transverse groove) that receives the head segment 468 (FIG. 34A) of the surgical fastener 406. Thus, the surgical fastener 406 is physically connected or captured relative to a remainder of the repair system 400, but is exposed distal the catheter distal end 422.

With further proximal retraction of the tube 470/anchoring mechanism 472 relative to the delivery catheter 402, the surgical fastener 406 can be loaded entirely within the delivery catheter 402. FIG. 34C illustrates this arrangement, with the surgical fastener 406 positioned proximal the catheter distal end 422.

The surgical fastener 406 can be partially and subsequently released from the delivery catheter 402 and the fastener delivery assembly 408 by reversing the above steps (transitioning from the arrangement of FIG. 34C to the arrangement of FIG. 34A). The tube 470/anchoring mechanism 472 is distally advanced relative to the catheter distal end 422. Once again, in the arrangement of FIG. 34B, the surgical fastener 406 is exteriorly exposed distal the delivery catheter 402, but remains physically connected to the fastener delivery assembly 408 (and thus the delivery catheter 402). With further distal advancement to the arrangement of FIG. 34A in which the hinge point 484 is distal the catheter distal end 422, the jaws 480, 482 self-revert to the normal, splayed apart positioning, allowing the surgical fastener 406 to freely release from the anchoring mechanism 472.

Use of the repair system 400 is akin to previous embodiments. In an initial delivery state reflected by FIG. 31C, the capture assembly 404 and the fastener delivery assembly 408 are proximally retracted relative to the delivery catheter 402, locating or loading the surgical fastener 406 and the capture body 412 (FIG. 31B) within the delivery catheter 402 (proximal the catheter distal end 422). Using a transeptal approach, the distal end 422 is advanced to the mitral valve as previously described (e.g., using the deflection mechanism 424 (FIG. 30) to steer the distal end 422. After the distal end 422 is located near the center of the valve, the retention sheath 432 is distally advanced beyond the catheter distal end 422 as shown in FIGS. 35A and 35B, for example by pushing on the coupling piece 452.

The capture body 412 is then deployed from the distal end 448 of the retention sheath 432 by pushing on the knob 442 as shown in FIGS. 35C and 35D. In some constructions, in the deployed location of the capture body 412 relative to the retention sheath 432, the knob 442 engages the coupling piece 452, thereby locking the capture body 412 relative to the retention sheath 432 (so that the capture body 412 and the retention sheath 432 now operate as a single unit). If necessary, the capture body 412 can be telescoped toward or away from the catheter distal end 422 via a corresponding movement of the knob 442/coupling piece 452. Once a desired depth of the capture body 412 relative to the mitral valve has been achieved, the capture body 412 is rotated to capture tissue as previously described (e.g., by applying a rotational force onto the knob 442/coupling piece 452). Where necessary, a direction of rotation of the capture body 412 can be repeatedly reversed to release and recapture tissue multiple times until the clinician is satisfied with the location of the captured chordae/leaflets. Once desired tissue capture is achieved, the capture body 412 can be spatially locked relative to the delivery catheter 402 by operating the locking knob 454.

As shown in FIGS. 35E and 35F, the surgical fastener 406 is then distally advanced along/over the retention sheath 432, moving toward the capture body 412. For example, the clinician slides the actuator hub 474 distally forward relative to the handle 410. Movement of the hub 474 is transferred to the tube 470 and in turn the anchoring mechanism 472. The surgical fastener 406 is connected to the anchoring mechanism 472 as previously described, such that the fastener delivery assembly 408 functions to distally advance the surgical fastener 406. Alternatively or in addition, the handle 410 (and thus the delivery catheter 402) can be pulled proximally while the hub 474 is held in place. Regardless, the clip arm tips 466 of the surgical fastener 406 are distally advanced beyond the catheter distal end 422 and make contact with tissue otherwise captured by the capture body 412. The surgical fastener 406 slides over the retention sheath 432 due to an openness of the fastener's central region.

The surgical fastener 406 is then rotated while continuing to apply a slight amount of forward force in the distal direction (via user applied forces to the hub 474). As generally reflected by FIGS. 35G and 35H, rotation/distal movement of the surgical fastener 406 advances the clip arms 460, 462 into the leaflets and then around the chordae.

With the leaflets now connected to the surgical fastener 406, the capture body 412 is then retracted into the retention sheath 432 (primarily hidden in the view of FIG. 35H, but better shown in FIG. 35F). For example, the locking knob 454 is loosened, allowing the capture assembly shaft 430 (and thus the capture body 412) to be proximally retracted relative to the retention sheath 432. FIGS. 35I and 35J illustrate the system 400 upon retraction of the capture body 412 (hidden in FIGS. 35I and 35J, but shown in FIG. 35H), and show the shaft 430 proximally retracted relative to the coupling piece 452, and thus relative to the retention sheath 432. Regardless, with the capture body 412 retracted, placement and attachment of the surgical fastener 406 relative to the leaflets can be evaluated by the clinician. If not satisfied with the placement or attachment, the surgical fastener 406 can be rotated in an opposite direction (and simultaneously pulled proximally) to remove the surgical fastener 406 from the tissue, and the chordae capturing and surgical fastener insertion process repeated.

Once satisfied with placement and attachment of the surgical fastener 406, the delivery catheter 402 is proximally retracted relative to the anchoring mechanism 472 as shown in FIGS. 35K and 35L. In particular, the handle 410 is pulled while the hub 474 is held in place. Once the catheter distal end 422 is proximal the hinge point 484, the jaws 480, 482 self-revert to the open arrangement shown. In the open arrangement, the surgical fastener 406 is no longer captured or physically held by the anchoring mechanism 472.

Apart from the surgical fastener 406, the entire repair system 400 is retracted to separate the anchoring mechanism 472 from the surgical fastener 406 as shown in FIGS. 35M and 35N. The delivery catheter 402 is then distally advanced relative to the fastener delivery assembly 408. As the catheter distal end 422 passes over the hinge point 484, the delivery catheter 402 forces the jaws 480, 482 toward one another, allowing the anchoring mechanism 472 to be proximally retracted within the confines of the delivery catheter 402. The repair system 400 (apart from the deployed surgical fastener 406) is then removed from the patient.

In other embodiment repair systems in accordance with the principles of the present disclosure employ a surgical fastener configured to provide both chordae capturing and leaflet fastening features. For example, another surgical fastener 550 in accordance with the principles of the present disclosure is shown in FIGS. 36A-36D. The fastener 550 generally includes a first arm 552, a second arm 554, and base member 556. The arms 552, 554 extend from the base member 556 in a generally identical yet opposite manner that forms a region for capturing chordae and another region for securing or clipping tissue. The base member 556 interconnects the arms 552, 554, and is constructed for interface with one or more delivery assemblies as described below.

As mentioned above, the arms 552, 554 can be identical, such that the following description of the first arm 552 applies equally to the second arm 554. The arm 552 is formed of a shaped memory alloy (e.g., Nitinol), and is configured to assume the memory set shape (in a normal arrangement) reflected in the views. The memory set shape of the first arm 552 defines an inverting segment 560, a spiral segment 562, and a capture segment 564. The capture segment 564 is akin to the capture body legs 62, 64 (FIG. 3A), and terminates at a distal tip 566. One or more bends in the inverting and spiral segments 560, 562 dictates a spatial location of the capture segment 564 (and the distal tip 566) relative to the base member 556 as described below.

The inverting segment 560 projects away from the base member 556, and defines a curvature or bend 570. As best shown in FIG. 36D, the bend 570 entails both radial and longitudinal components (relative to an axial center line C of the surgical fastener 550) in extension from the base member 556. To better explain the spatial orientation of the inverting segment 560, and particularly the bend 570, it can be helpful to reference a trailing point 572 and a leading point 574 along the inverting segment 560. The trailing point 572 is adjacent the base member 556 (i.e., where the arm 552 initially transitions from the base member 556), whereas the leading point 574 is adjacent the spiral segment 562 (i.e., where the arm 552 transitions from the inverting segment 560 to the spiral segment 562). With these conventions in mind, the bend 570 locates the leading point 574 radially outward of the trailing point 572 (relative to the center line C). Further, the inverting segment 560 initially projects downward (e.g., longitudinally away from the base member 556) from the trailing point 572 to the bend 570; the bend 570 reverses the longitudinally downward extension (i.e., an apex 575 of the bend 570 is opposite the base member 556), extending upwardly to locate the leading point 574 longitudinally closer or proximate the base member 556 (i.e., relative to the orientation of FIG. 36D, the leading point 574 is "above" the apex 575).

With continued reference to FIGS. 36A-36D, the spiral segment 562 projects from the inverting segment 560 in a generally upward (i.e., toward the base member 556) direction, forming a spiral bend 576. The spiral bend 576 has a circumferential-like component of extension between the inverting segment 560, circumferentially offsetting the "starting" point of the capture segment 564 relative to the "ending" point (e.g., the leading point 574 referenced above) of the inverting segment 560 (with respect to a "circumference" generally defined by a curvature of the capture segment 564). As shown, the spiral segment 562 spatially locates the capture segment 564 above the inverting segment 560 (relative to the orientation of the views). As a point of reference, the top view of FIG. 36B illustrates the spiral segment 562 of the first arm 552 extending in a direction "opposite" a direction of extension of the spiral segment 562 of the second arm 554. It should be understood, however, that relative to the central axis C, this "opposite" direction of extension reflects the arms 552, 554 as defining an identical wind direction (e.g., counter-clockwise relative to the orientation of FIG. 36B).

The capture segment 564 establishes, in the normal arrangement, either a clockwise or counter-clockwise wind direction as previously described. The capture segment 564 of the second arm 554 extends in or with an identical wind direction, such that the first and second arms 552, 554 combine to form a hurricane-like or spiral shape as best reflected in the top plan view of FIG. 36B. In this regard, and as illustrated in FIGS. 36A and 36D, extension of the capture segment 564 from the spiral segment 562 has a downward component, such that the distal tip 566 is "below" the spiral segment 562/capture segment 564 junction. The longitudinally downward component of the first and second arm capture segments 564 are correlated such that the capture segment 564 of the first arm 552 passes under the capture segment 564 of the second arm 554, and vice-versa.

The base member 556 can assume various forms appropriate for interface with a corresponding delivery assembly, and, for example, can form a loop 580 or similar hook-shaped structure. A sleeve 582 or similar body can be provided, and serves to crimp the arms 552, 554 to one another at the base member 556. For example, a first wire can be processed to form the first arm 552, a second wire forms a second arm 554, and a third wire forms the loop 580; the sleeve 582 crimps the first-third wires to one another, with the loop 580 being exposed proximal the sleeve 582. Other attachment constructions are also envisioned, such as adhesion, glue, solder, welds, etc. In other embodiments, the shaped fastener 550 can be formed from a single wire and the sleeve 582 eliminated.

Figure 37:
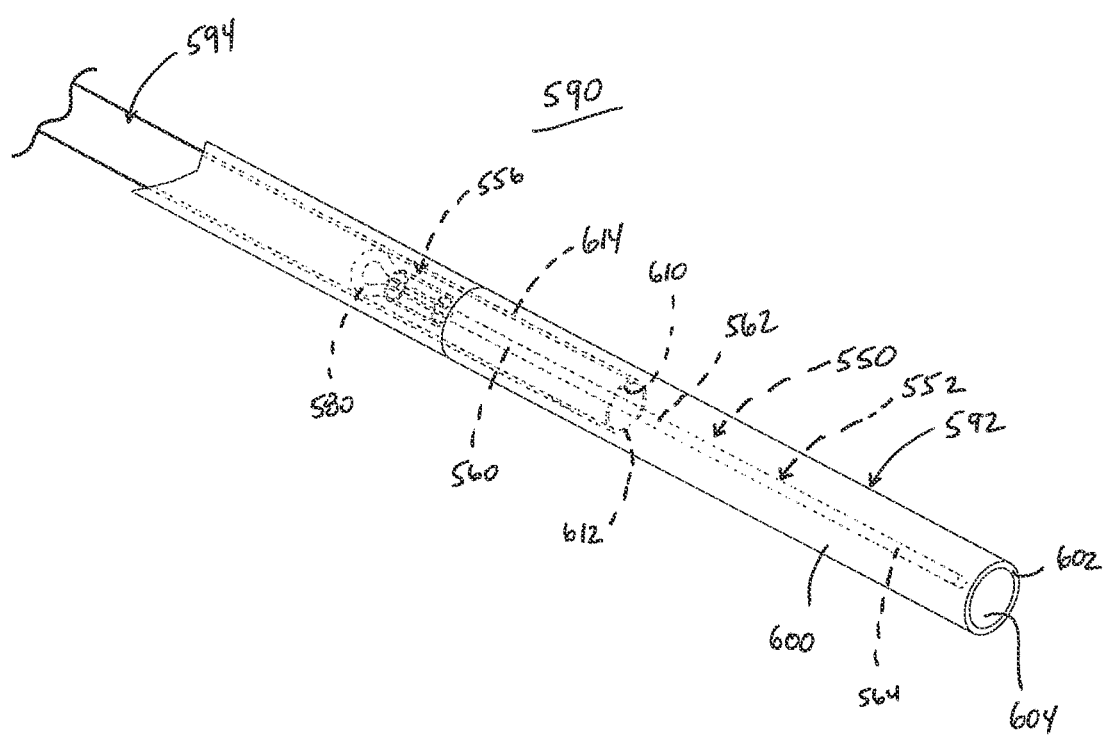
FIG. 37 is a perspective view of a portion of another transcatheter mitral valve repair system in accordance with principles of the present disclosure including the surgical fastener of FIG. 36A.

As with previous embodiments, the surgical fastener 550 is configured to be deflectable from the three dimensional spiral shaped shown to a more straightened or linear shape, and then self revert back to the normal arrangement. With this in mind, FIG. 37 illustrates a portion of a repair system 590 otherwise including the surgical fastener 550 maintained within a deflected arrangement. In general terms, in addition to the surgical fastener 550, the repair system 590 includes a delivery catheter 592 and guide sheath 594. Though not shown in the view, the system 590 further includes a fastener delivery assembly and a handle akin to previous embodiments and maintaining various components useful in manipulating the repair system 590 by a user. With this construction, the system 590 provides a delivery state in which the surgical fastener 550 is maintained within the delivery catheter 592, a partial deployment or chordae capture state in which a portion of the surgical fastener 550 is exposed distal the delivery catheter 592, and a release or deployment state in which the fastener 550 is fully released from the delivery catheter 592.

The delivery catheter 592 can assume any of the forms previously described, and generally include a distal section 600 terminating at a distal end 602. Whereas a remainder of the delivery catheter 592 can have a more flexible construction appropriate for traversing a patient's vasculature, the distal section 600 can have a more rigid construction (e.g., stainless steel), with the catheter 592 incorporating various components useful for effectuating steering of the distal end 602. Regardless, the catheter 592 forms or defines a lumen 604 within which other components of the system 590 are slidably disposed.

The guide sheath 594 is sized to be slidably received within the delivery catheter lumen 604, and defines a guide lumen 610 extending to and open at a distal end 612. As shown, the guide lumen 610 is sized to receive the surgical fastener 550, with at least a distal region 614 of the guide sheath 594 having sufficient circumferential rigidity (either alone or in combination with a circumferential rigidity provided by the delivery catheter 592) to force and retain the surgical fastener 550 in a deflected arrangement. Though not shown, the fastener delivery assembly extends through the guide sheath lumen 610 and is selectively coupled to the surgical fastener 550. For example, the fastener delivery assembly 30 (FIG. 1), including the push tube 140 (FIG. 1) and the tether 142 (FIG. 1), described above can be employed with the system 590. Once again, the push tube 140 can be longitudinally advanced or retracted relative to the delivery catheter 592 and the guide sheath 594 to effectuate distal movement of the surgical fastener 550 (via abutting contact with the base member 556). The tether 142 is disposed (threaded) within the push tube 140, and is selectively connected with the surgical fastener 550 by threading tether 142 through the loop 580.

FIG. 37 reflects a delivery state of the system 590. As shown, the surgical fastener 550 is fully captured with the delivery catheter 592 (i.e., is entirely proximal the distal end 602). Further, the surgical fastener 550 is partially captured within the guide sheath 594. For example, and with additional reference FIG. 36A, the inverting segment 560 of each of the arms 552, 554 (the first arm 552 being shown with dashed lines in the view of FIG. 37) is disposed within the guide sheath 594, whereas the capture segment 564 and a portion of the spiral segment 562 of the arms 552, 554 is distal the guide sheath 594 (though still within the delivery catheter 592). With this arrangement, the delivery catheter 592 and/or the guide sheath 594 force the arms 552, 554 away from the normal arrangement and toward the straightened arrangement reflective in the view.

During use, the system 590 is initially in the delivery state, and the distal section 600 of the delivery catheter 592 inserted into the femoral vein and advanced up to the right atrium and then across the atrial septum into the left atrium as with previous embodiments. The distal end 602 is then steered toward the center of the mitral valve.

Figure 38A:
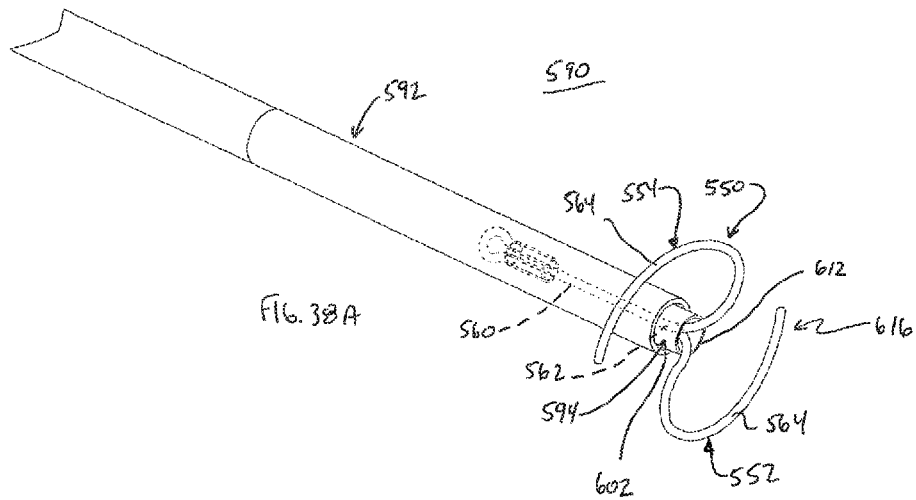
FIGS. 38A-38E illustrate use of the system of FIG. 37 in percutaneously repairing a defective mitral valve in accordance with principles of the present disclosure.

As shown in FIG. 38A, the guide sheath 594 is distally advanced relative to the delivery catheter 592 such that the distal end 612 of the guide sheath 594 is distally beyond the distal end 602 of the delivery catheter 592. The surgical fastener 550 is then distally advanced relative to the guide sheath 594, locating a portion of each of the first and second arms 552, 554 distal the guide sheath distal end 612 (and thus distal delivery catheter distal end 602). For example, the capture segment 564 of each of the arms 552, 554 is advanced distally beyond the guide sheath 594 (and the delivery catheter 592), with the capture segments 564 self-reverting to the normal arrangement. The so-transitioned capture segments 564 combine to define a structure or capture body 616 (referenced generally) akin to the capture body described above with previous embodiments. A remainder of the arms 552, 554 (e.g., at least a portion of the spiral segment 562 and an entirety of the inverting segment 560) are proximal the distal end 612 of the guide sheath 594 and thus remain forced to the more straightened shape.

Figure 38B:
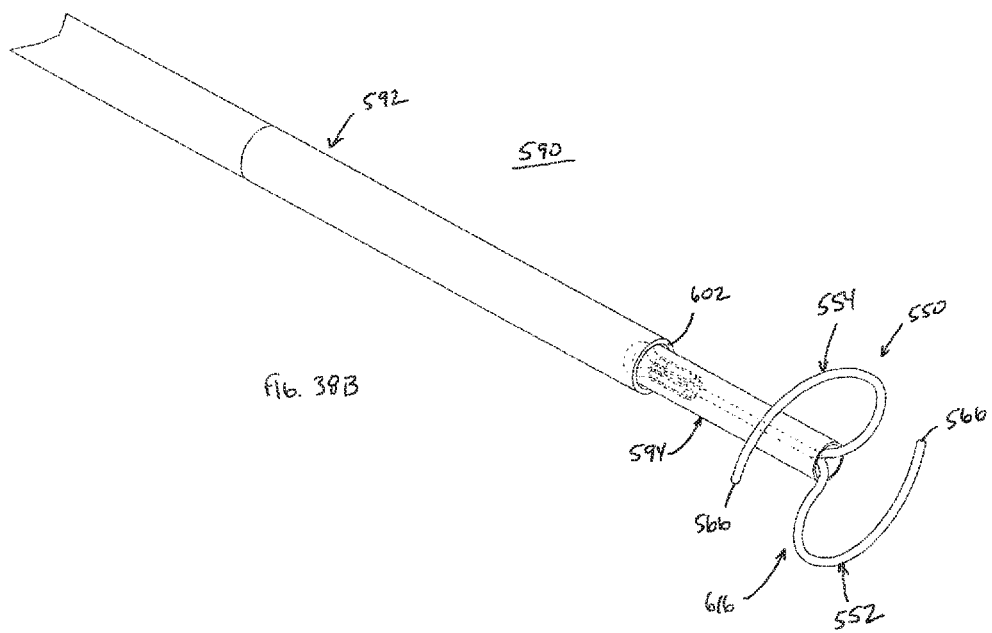
Figure 38C:
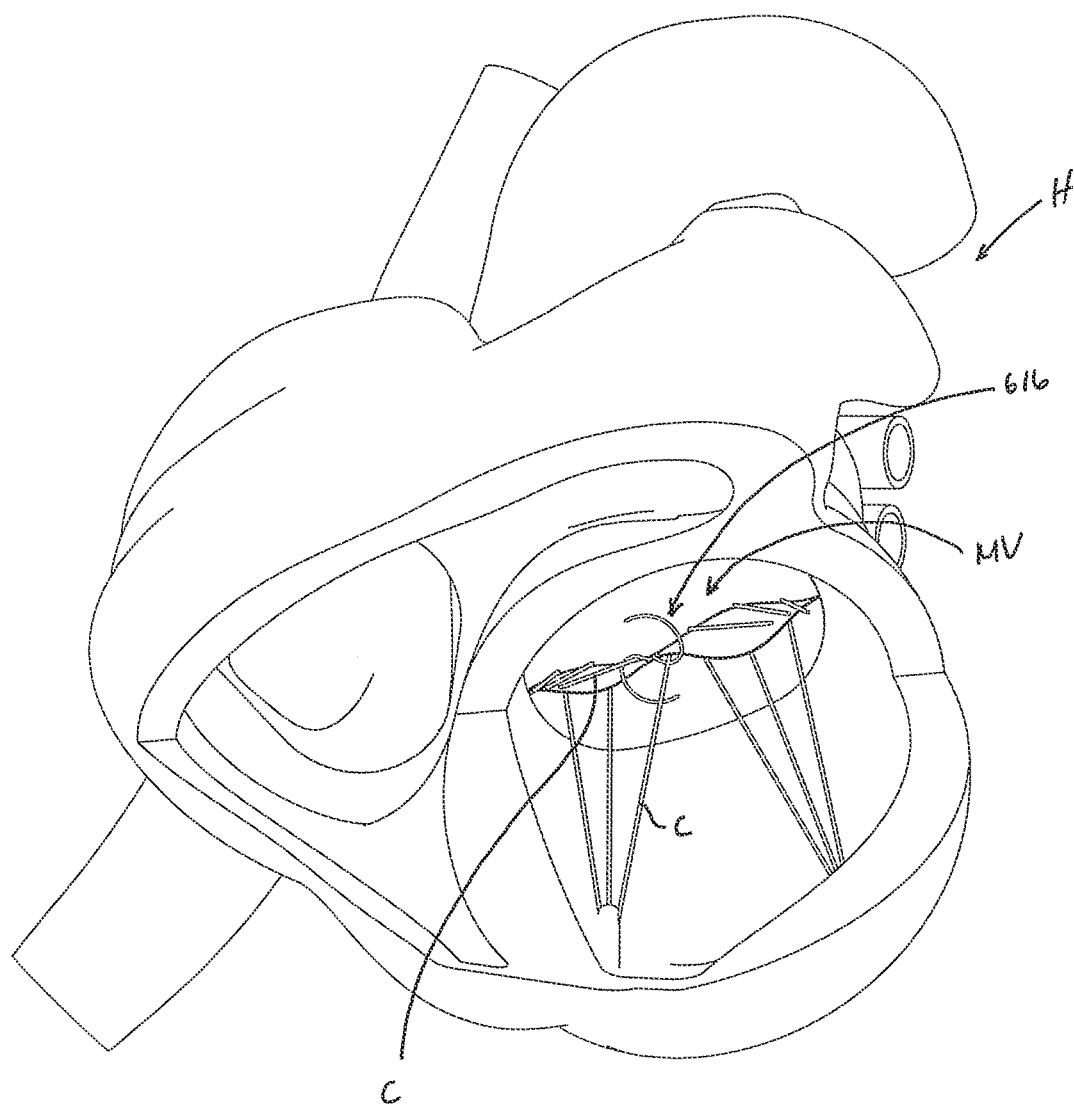

In the capture configuration of FIG. 38A, the guide sheath 594 (and thus the connected surgical fastener 550) can be further distally advanced relative to the delivery catheter distal end 602 as shown in FIG. 38B. This telescope-type manipulation of the guide sheath 594/surgical fastener 550 relative to the delivery catheter 592 is employed to position the capture body 616 at an optimal depth within the mitral valve. Once inside the left ventricle, the capture body 616 can be rotated to capture chordae as previously described. For example, FIG. 38C illustrates the captured body 616 within the heart H and pulling chordae C together at a center of the mitral valve MV.

Figure 38D:
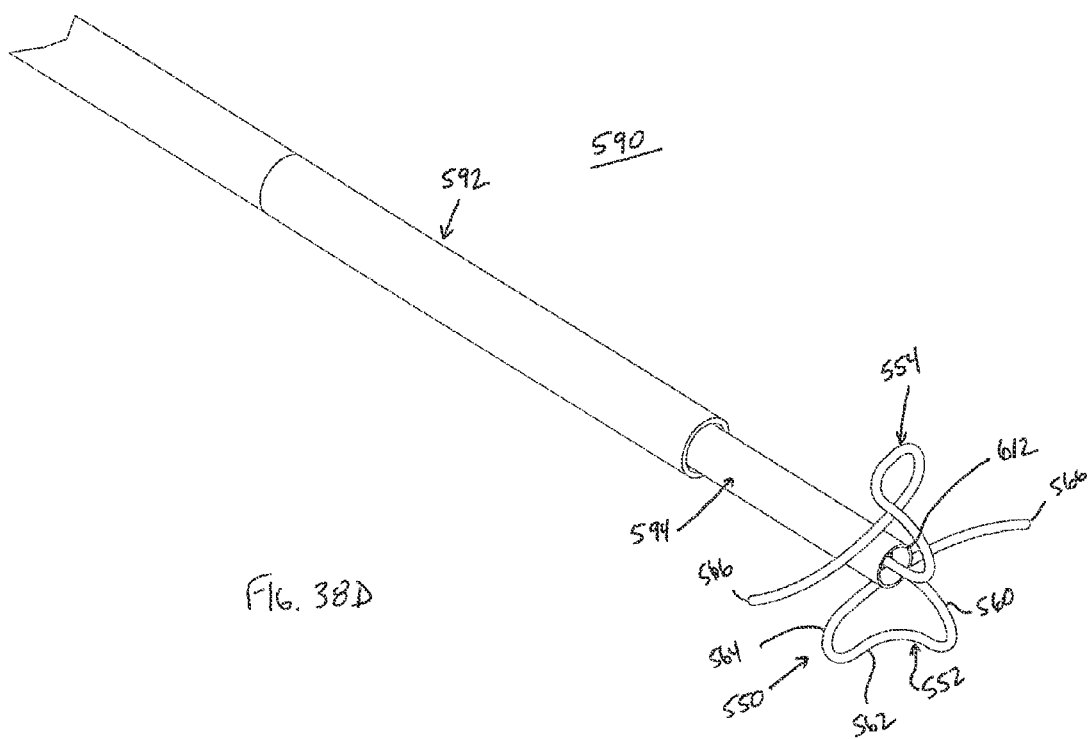

After chordae C is captured, the fastener delivery assembly (not shown) is advanced relative to the guide sheath 594, forcing the arms 552, 554 distally beyond the guide sheath distal end 612 as shown in FIG. 38D. With this distal advancement, the spiral segment 562 and the inverting segment 560 of the arms 552, 554 are located beyond the confines of the guide sheath 594, and thus allowed to self-revert toward the normal arrangement. Due to the bends associated with the segments 560, 564, the distal tip 566 of each of the arms 552, 554 reverses a spatial orientation, and helps to anchor the surgical fastener 550 so that the surgical fastener 550 does not unwind. For example, a comparison of the arrangements of FIGS. 38B and 38D illustrates the tips 566 being distal the guide sheath distal end 612 in the capture state of FIG. 38B, and spatially proximal the guide sheath distal end 612 in the anchoring state of FIG. 38D. The orientation reversal also creates a loop in the surgical fastener 550 that helps to retain the captured chordae.

Prior to complete release of the surgical fastener 550, the capture location and effectiveness can be tested as previously described. In the event the clinician determines that location and/or effectiveness is not optimal, the surgical fastener 550 can be recaptured relative to the guide sheath 594 and/or the delivery catheter 592, and the process repeated at a different location.

Figure 38E:
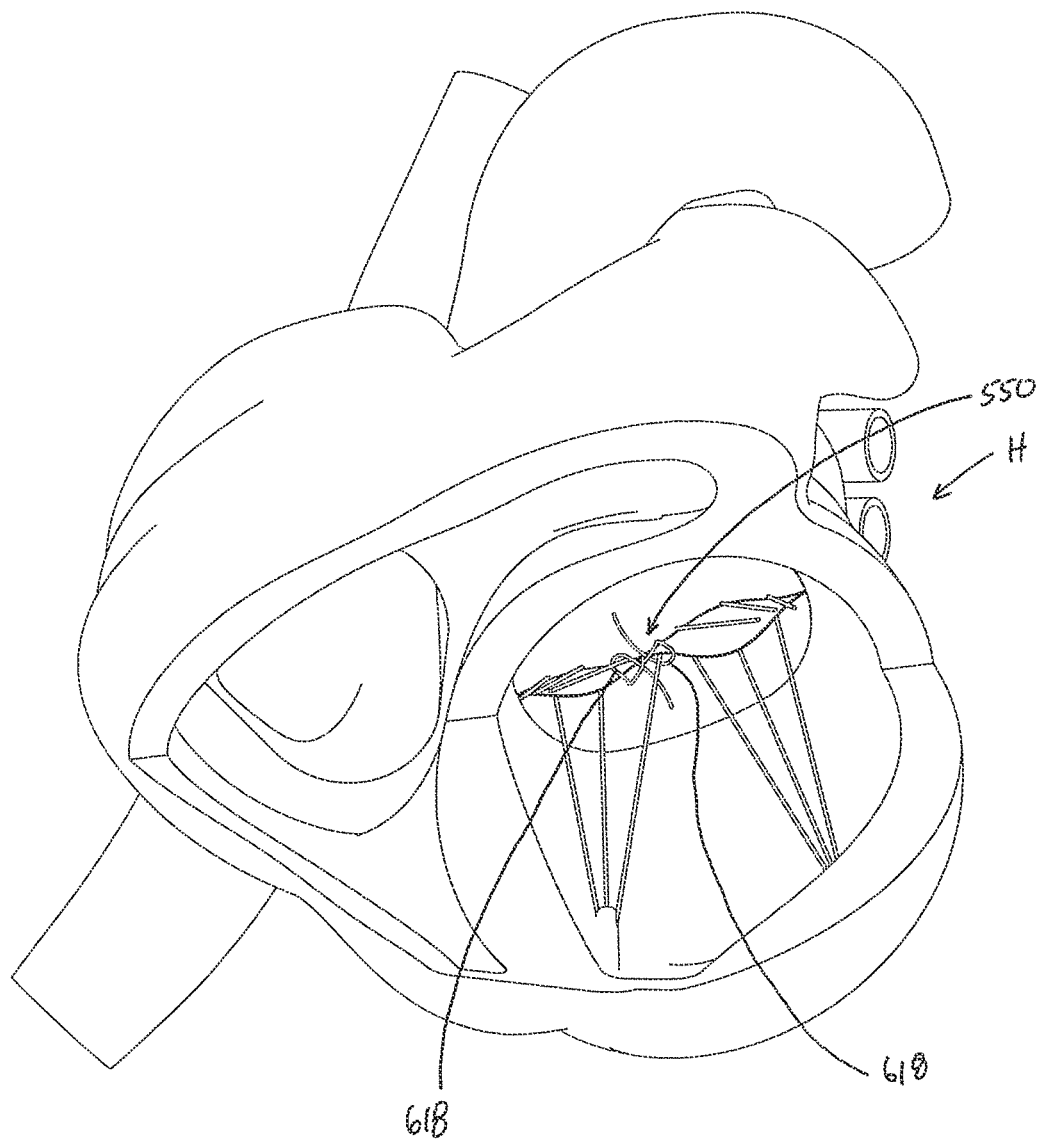

If satisfied with the placement, the surgical fastener 550 can be released from a remainder of the repair system 590 by pulling one end of the tether 142 (FIG. 1) as previously described until the tether 142 is completely removed from the corresponding tube 140 (FIG. 1). The system components (apart from the surgical fastener 550) are then removed from the patient, and the implant is complete. FIG. 38E illustrate the surgical fastener 550 fully deployed in the heart H and a chordae retaining loop formed by the surgical fastener 550 identified at 618.

Figure 39:
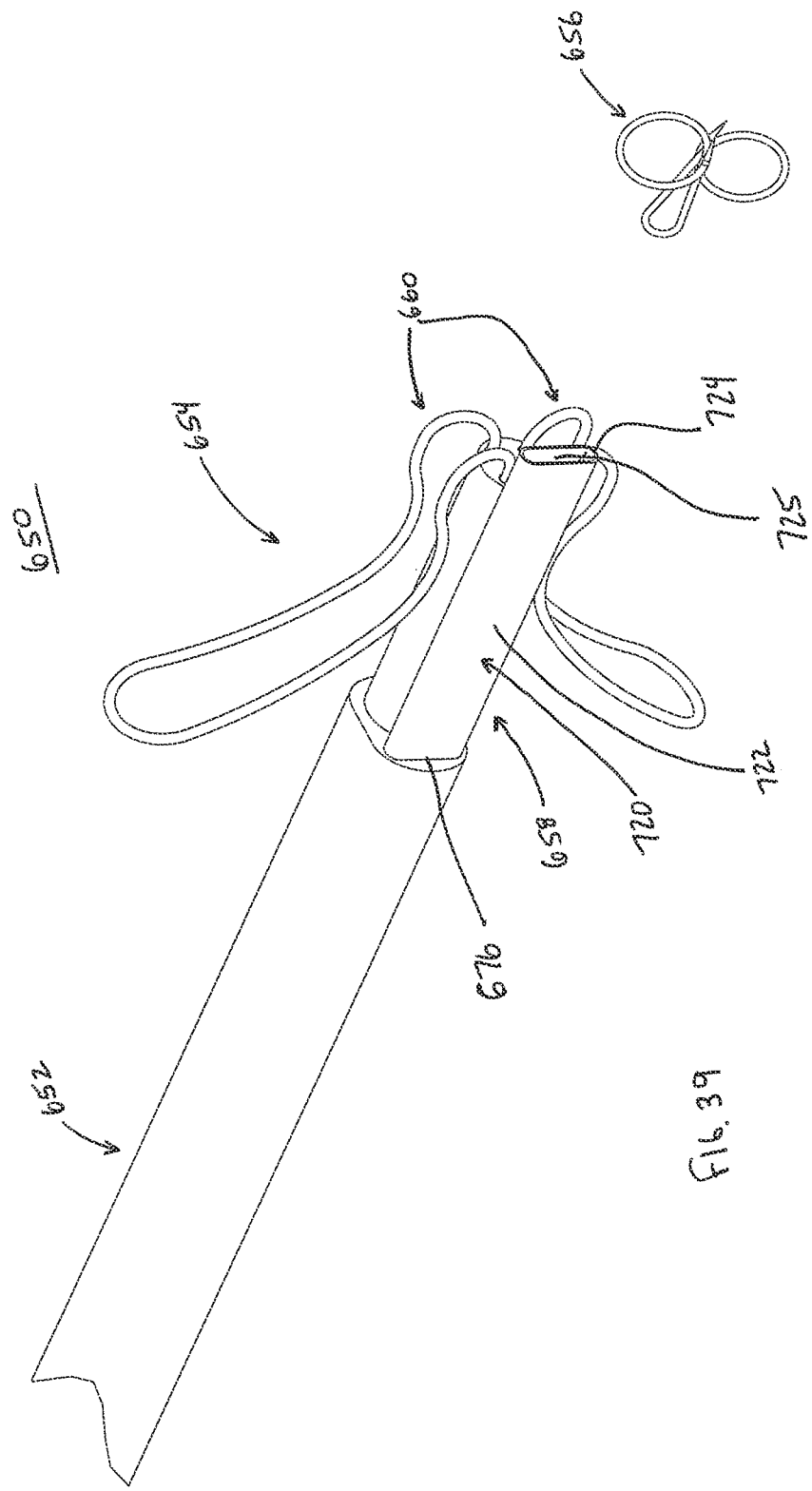
FIG. 39 is a perspective, partially exploded view of a portion of another transcatheter mitral valve repair system in accordance with principles of the present disclosure.

Portions of yet another embodiment repair system 650 in accordance with principles of the present disclosure shown in FIG. 39. The system 650 includes a delivery catheter 652, a capture assembly 654, a surgical fastener 656, and a fastener delivery assembly 658. Similar to previous embodiments, the delivery catheter 652 is configured to slidably retain the capture assembly 654 and the fastener delivery assembly 658. The capture assembly 654 provides a capture body 660 (referenced generally) configured to be transitionable from the normal arrangement illustrated in FIG. 39 to a collapsed arrangement within the delivery catheter 652. Similarly, the surgical fastener 656 is transitionable from the undeflected arrangement shown in FIG. 39 to a deflected arrangement within the fastener delivery assembly 658 (and thus within the delivery catheter 652). In a delivery state of the system 650, the capture body 660 and the surgical fastener 656 are retained within the delivery catheter 652 for percutaneous delivery to a mitral valve target site. In a capture state of the system 650, at least a portion of the capture body 660 is deployed from the delivery catheter 652, self-transitions to the normal arrangement shown and can be manipulated to capture or engage tissue at the mitral valve target site. Finally, in a release state, the surgical fastener 656 is deployed from the delivery catheter 652 and released from the fastener delivery assembly 658, and self-reverts to the undeflected arrangement shown to capture or fasten opposing tissue segments of the mitral valve target site to one another. Optionally, the system 650 can incorporate additional components, such as a handle assembly (not shown) configured to assist in user manipulation of the delivery catheter 652, the capture assembly 654, and/or the fastener delivery assembly 658.

Figure 40:
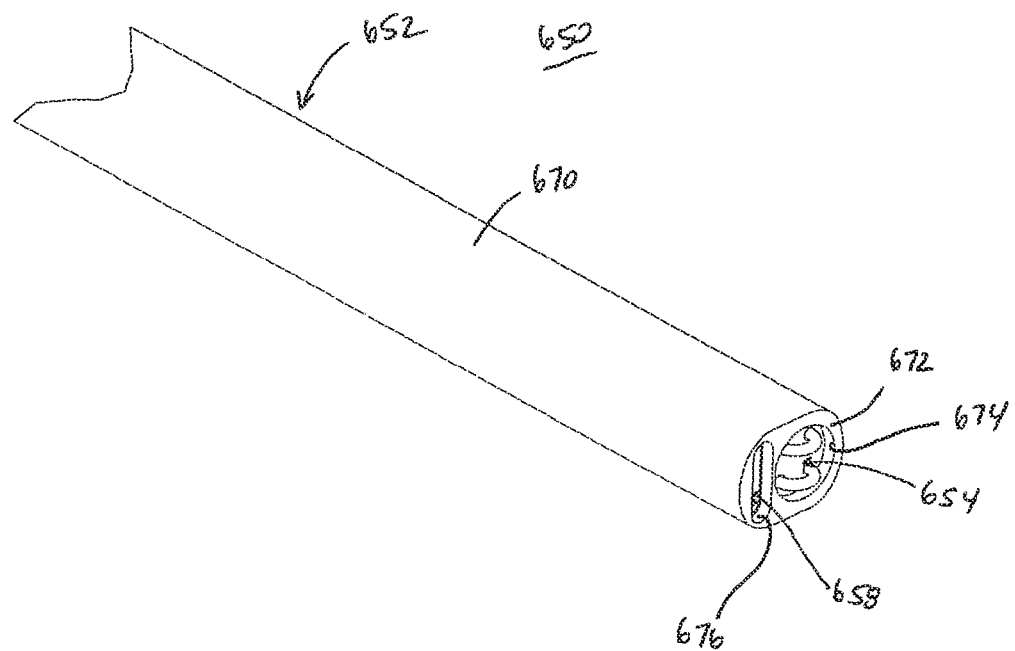
FIG. 40 is an enlarged, perspective view of a distal region of the system of FIG. 39, and illustrating a delivery catheter component thereof.

With reference to FIG. 40 (otherwise illustrating the capture assembly 654 and the fastener delivery assembly 658 retracted within the delivery catheter 652), the delivery catheter 652 can generally assume any of the configurations previously described. For example, the delivery catheter 652 can form or include a distal section 670 terminating at a distal end 672. The distal section 670 can have a more rigid construction as compared to a remainder of the delivery catheter 652 (e.g., the distal section 670 can be formed of stainless steel), but is otherwise sufficiently flexible for traversing the patient's vasculature. Regardless, the delivery catheter 652 forms or defines first and second lumens 674, 676. The lumens 674, 676 extend at least a majority of a length of the delivery catheter 652, and are open at the distal end 672. The first lumen 674 is sized and shaped to slidably receive the capture assembly 654 and can have the circular cross-sectional shape shown. Similarly, the second lumen 676 is sized to slidably receive the fastener delivery assembly 658, and can have an elongated profile. The lumens 674, 676 are arranged side-by-side to facilitate a side deployment technique described below.

The capture assembly 654 is shown in greater detail in FIGS. 41A-41C, and includes a shaft 680 maintaining the capture body 660. The capture body 660 is collectively defined by first and second petals 682, 684. The petals 682, 684 can be identical, with the following description of the first petal 682 applying equally to the second petal 684. As a point of reference, the petals 682, 684 are, in some embodiments, retractable and extendable relative to a distal end 686 of the shaft 680, with FIGS. 41A-41C illustrating a fully deployed (or extended) state of the petals 682, 684 relative to the shaft 680. In the fully deployed state, the petals 682, 684 are free of external constraints or compressive forces, and naturally assume the normal (memory set) shape or arrangement shown. The memory set shape of the first petal 682 in the fully deployed state is described below. In particular, the petal 682 extends from the distal end 686 of the shaft 680 and terminates at an atraumatic tip 688. A memory set shape of the petal 682 defines an inverting segment 690, a transition segment 692, and a leaflet contact segment 694. The inverting segment 690 projects distally from the shaft 680, and forms an inverting bend, such that the inverting segment 690 curves or turns in the proximal direction. The transition segment 692 further projects in the proximal direction in extension from the inverting segment 690, and further effectuates a radially inward bend (toward a center line of the shaft 680). The leaflet contact segment 694 curves radially outwardly in extension from the transition segment 692 to the tip 688. As identified in FIG. 41B, extension of the leaflet contact segment 694 forms a leaflet landing zone 696 that facilitates capture of mitral valve leaflet tissue as described below.

The second petal 684 defines an identical shape as the first petal 682, and is provided as a mirror image of the first petal 682 (i.e., relative to a circumference of the shaft 680, the first and second petals 682, 684 are located 180° apart). In some embodiments, the petals 682, 684 are each formed from a shape memory wire (e.g., Nitinol™ wire), or some other super elastic shape memory material, and are flexible enough to be retracted inside the shaft 680, yet rigid enough to contain the mitral valve leaflets when in the natural arrangement shown in FIGS. 41A-41C. With the wire-based construction, the wire forming each petal 682, 684 (either a single wire forming both petals 682, 684, or two separate wires) can be viewed as defining opposing side segments 698, 700 (identified for the second petal 684 in FIGS. 41A and 41C) connected at the tip 688. The side segments 698, 700 are slidably retained by the shaft, for example passing through holes in the shaft distal end 686. The shaft 680 can form a discrete lumen at each hole and within which corresponding ones of the side segments 698, 700 are slidably received, or can be hollow. Regardless, the petals 682, 684 can be retracted into the shaft 680 by pulling on the wire(s) to draw the side segments 698, 700 into the shaft. FIG. 41D illustrates the retracted arrangement of the petals 682, 684 relative to the shaft 680 in the retracted state, noting that the tips 688 may project slightly distal the shaft distal end 686.

Figure 42A:
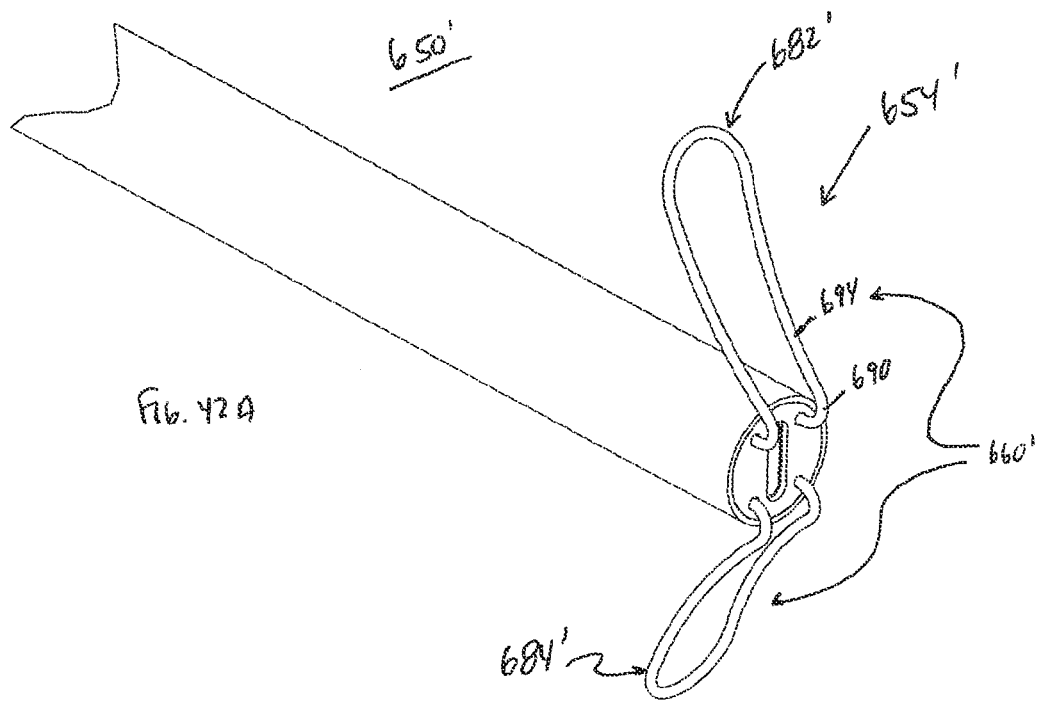
FIG. 42A is a perspective view illustrating another capture body useful with the system of FIG. 39.

The above-described shape and format of the petals 682, 684 in the normal arrangement of FIGS. 41A-41C are but one acceptable configuration appropriate for capturing leaflets. A wide variety of other constructions are also envisioned so long as the petals 682, 684 exhibit sufficient rigidity to hold the leaflets, facilitate navigation through the chordae (as described below) for both deployment and retraction, and can be retracted and removed after placement of the surgical fastener 656 (FIG. 39). With this in mind, FIG. 42A illustrates a portion of an alternative embodiment system 650' that includes an alternative capture assembly 654'. The capture assembly 654' provides a capture body 660' (referenced generally) that is defined by opposing, first and second petals 682', 684'. The petals 682', 684' are highly similar to the petals 682, 684 (FIG. 41A) described above. With the construction of FIG. 42A, however, the petals 682', 684' progress directly from the inverting segment 690 to the leaflet contact segment 694. In other words, the transition segment 692 (FIG. 41A) is omitted.

Figure 42B:
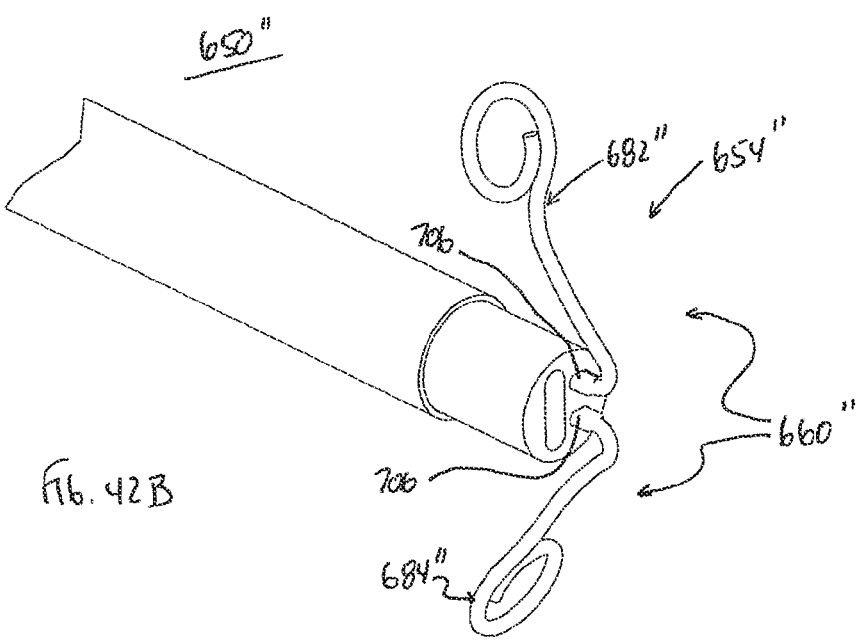
FIG. 42B is a perspective view illustrating another capture body useful with the system of FIG. 39.

Another embodiment capture assembly 654" in shown in FIG. 42B, and again includes a capture body 660" collectively defined by first and second petals 682", 684", extending from a shaft 680". The petals 682", 684" are each formed by a single wire having a larger diameter as compared to previous embodiments. A profile of the petals 682", 684" in the normal arrangement shown is highly akin to the shaped described above. Optionally, the capture assembly 654" provides an orienting feature 706 (referenced generally) between the shaft 680" and each of the petals 682", 684" that prevents the petals 682", 684" from rotating relative to the shaft 680". For example, the wire associated with each of the petals 682", 684" can be flattened along the area of contact or interface with the shaft 680".

Returning to FIG. 39, the surgical fastener 656 can assume a wide variety of forms. One non-limiting example of the surgical fastener 656 is shown in greater detail in FIG. 43, and includes first and second self-closing clips 710, 712 extending from a base member 714. The surgical fastener 656, or at the least the clips 710, 712, is formed from a single Nitinol (or other shape memory alloy) wire, and is formed such that each of the clips 710, 712 has a memory set shape (in the normal arrangement shown) that forms one or more complete or partial capture loops 716 and terminates at a sharpened tip 718. In a deflected arrangement, the clips 710, 712 can be rendered substantially straight or linear (e.g., the loop(s) 716 is no longer discernable). Upon removal of the deflection force, the clips 710, 712 self-transition or revert back to the memory set loop shape of the undeflected arrangement, re-forming the loop(s) 716. The base member 714 can assume various forms, assembly embodiment forms and attachment loop 719 sized and shaped for interface with the fastener delivery system 658 (FIG. 39). Various wire sizes and loop sizes can be employed.

Returning to FIG. 39, the fastener delivery assembly 658 can have a variety of constructions configured to facilitate delivery of the surgical fastener 656 from the delivery catheter 652, as well as selective release of the surgical fastener 656 from the fastener delivery assembly 658. In general terms, the fastener delivery assembly 658 includes a guide sheath 720 that is sized to be slidably received within the second lumen 676 (referenced generally) of the delivery catheter 652. A distal region 722 of the guide sheath 720 can have a more rigid construction as compared to a remainder of the guide sheath 720 for retaining the surgical fastener 656 in a deflected arrangement. Regardless, the guide sheath 720 terminates at a distal end 724, and forms an internal passageway 725 along at least the distal region 722 and open at the distal end 724.

The fastener delivery assembly 658 further includes one or more additional components for manipulating the surgical fastener 656 within the guide sheath 720, as well as for selectively releasing the surgical fastener 656 when deployed from the distal end 724. For example, FIGS. 44A and 44B reflect the fastener delivery assembly 658 as further including an engagement device 730 in some embodiments. The engagement device 730 includes a shank 732 and a splitable tip 734. The shank 732 and the splitable tip 734 can be formed as an integral, homogeneous body, with the splitable tip 734 defined by opposing fingers 736, 738. As best shown in the view of FIG. 44A, the fingers 736, 738 are connected to the shank 732 at a hinge point 740, with the splitable tip 734 having a shape memory characteristic that naturally basis the fingers 736, 738 away from one another in extension from the hinge point 740 to a corresponding distal end 742, 744. Each of the fingers 736, 738 forms a slot 746 at the distal end 742, 744 thereof (with FIG. 44A providing a more complete illustration of the slot 746 provided with the first finger 736). The slots 746 are sized and shaped in accordance with a size and shape of the attachment loop 719 provided with the surgical fastener 656.

Mounting of the surgical fastener 656 to the fastener delivery assembly 658 entails placement of the attachment loop 719 into one of the slots 746 (relative to the with the fingers 736, 738 in the normal, distally splayed condition of FIG. 44A). The engagement device 730 is then proximately retracted relative to the guide sheath 720. As the hinge point 740 is moved proximal the guide sheath distal end 724, the guide sheath 720 forces the fingers 736, 738 to a closed arrangement shown in FIG. 44B. In the closed arrangement, then, the surgical fastener 656 is coupled to the splitable tip 734. With further proximal retraction of the engagement device 730 relative to the guide sheath 720, the surgical fastener 656 is directed within the guide sheath internal passageway 725 (FIG. 39), and forced to a deflected arrangement in which the clips 710, 712 assume a more straightened shape. Conversely, with distal advancement of the engagement device 730 relative to the guide sheath 720 (i.e., transitioning from the arrangement of FIG. 44B to the arrangement of FIG. 44A), once the hinge point 740 is distal the guide sheath distal end 724, the splitable tip 734 naturally reverts to the open arrangement, permitting full release of the surgical fastener 656 from the fastener delivery assembly 658.

During use, the system 650 is initially arranged in the delivery state of FIG. 40. As generally shown, the capture assembly 654, including the petals 682, 684 is fully retracted or disposed within the first lumen 674 of the delivery catheter 652. Similarly, the fastener delivery assembly 658 (referenced generally) is located within the second lumen 676. Though hidden in the view of FIG. 40, the surgical fastener 656 (FIG. 39) is loaded within the fastener delivery assembly 658 as described above, and thus is also within the distal section 670 of the delivery catheter 652.

The distal section 670 of the delivery catheter 652 is percutaneously guided into the left atrium through the atrial septum (from the right atrium as with previous embodiments). The distal section 670 is guided to locate the distal end 672 near the center of the mitral valve.

The shaft 680 is then distally advanced from the delivery catheter distal end 672 as shown in FIG. 45A, and is navigated inside the left ventricle. As reflected in FIG. 45A, with this initial telescoping-type manipulation of the shaft distal end 686, the petals 682, 684 remain constrained within or by the shaft 680.

The petals 682, 684 are then distally advanced from the shaft 680 as shown in FIG. 45B. The petals 682, 684 can be advanced consecutively or simultaneously. Regardless, with advancement or deployment from the shaft 680, the petals 682, 684 self-revert to the normal, pre-formed shape (after being advanced beyond the corresponding inverting segment 690). The petals 682, 684 can be deployed or "opened" anywhere in the left ventricle and rotated into the desired orientation. However, to avoid having to navigate through the chordae, it may be desirable to rotate the petals 682, 684 into proper orientation before fully deploying. Alternatively, the petals 682, 684 can be deployed or opened in the left atrium, and then advanced through the mitral valve.

Figure 45C:
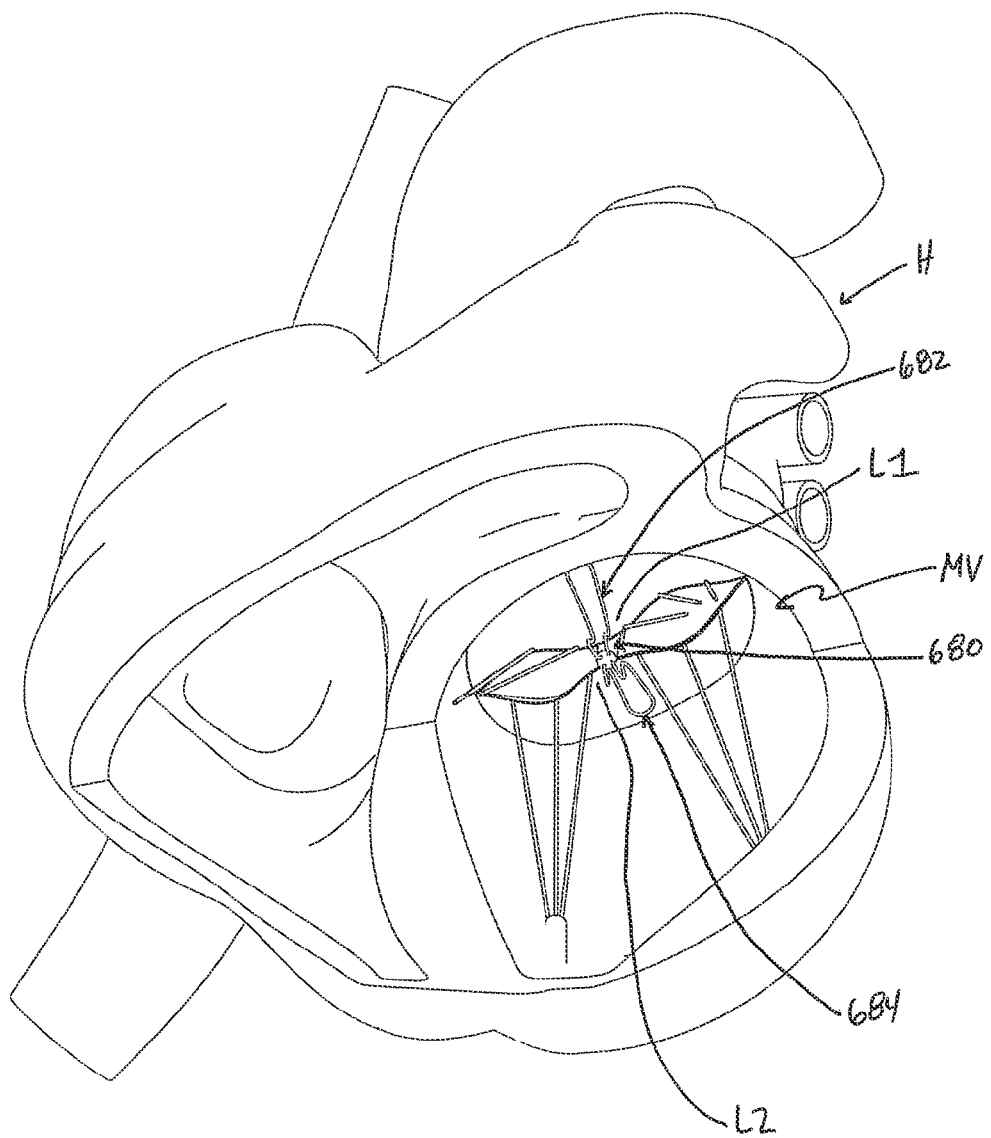

Once the petals 682, 684 are oriented generally perpendicular to the opening of the mitral valve, the shaft 680 is proximally retracted. This movement is transferred on to the petals 682, 684, with the corresponding leaflet landing zones 696 contacting and then guiding the mitral value leaflets. FIG. 45C illustrates the petals 682, 684 in the capture configuration within the heart H, pulling the leaflets L1, L2 together at the center of the mitral valve MV.

If the clinician is satisfied with the location of the petals 682, 684 relative to the mitral valve MV, the guide sheath 720 of the fastener delivery assembly 656 is distally advanced locating the sheath distal end 724 adjacent or distally beyond the inverting segment 690 of the petals 682, 684 as shown in FIG. 45D. The guide sheath distal end 724 is thus located in the left ventricle. An orientation of the guide sheath distal end 724 relative to the petals 682, 684 is of interest. As described below, the surgical fastener 656 (FIG. 39) will subsequently be deployed from the guide sheath distal end 724. By locating the guide sheath distal end 724 distal the petals 682, 684, as well as by arranging the petals 682, 684 away from the guide sheath 720, the surgical fastener 656 will be deployed away from the petals 682, 684 (e.g., not within the loops of the petals 682, 684). The delivery catheter 652 can be rotated to ensure proper orientation.

FIGS. 45E and 45F illustrate the surgical fastener 656 then being partially deployed from the guide sheath distal end 724. For example, the shank 732 (FIG. 44A) is distally advanced relative to the guide sheath 720. As shown, in the partially deployed state, the clips 710, 712 self-revert toward the normal, looped arrangement, with the corresponding tips 718 pointing toward the mitral valve MV.

Figure 45G:
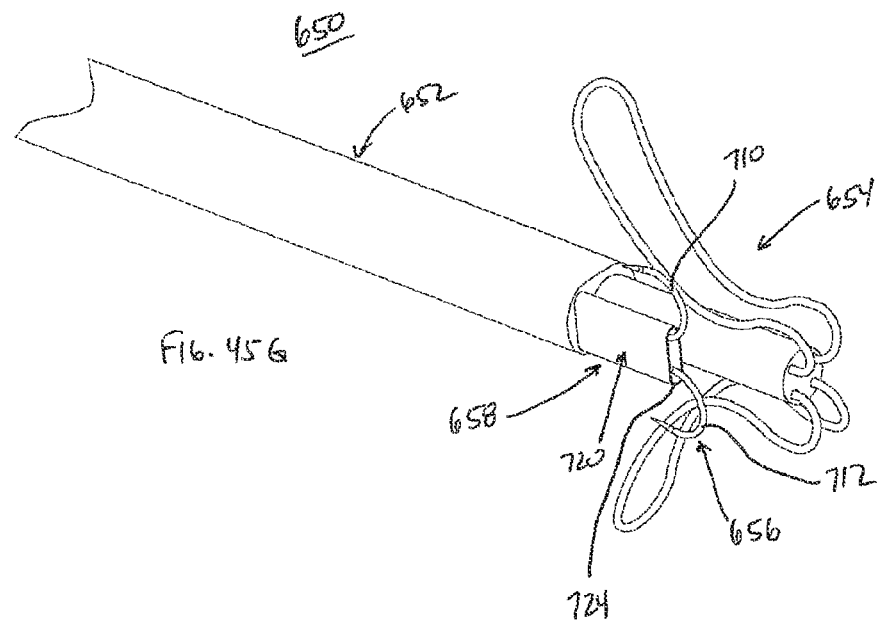
Figure 45H:
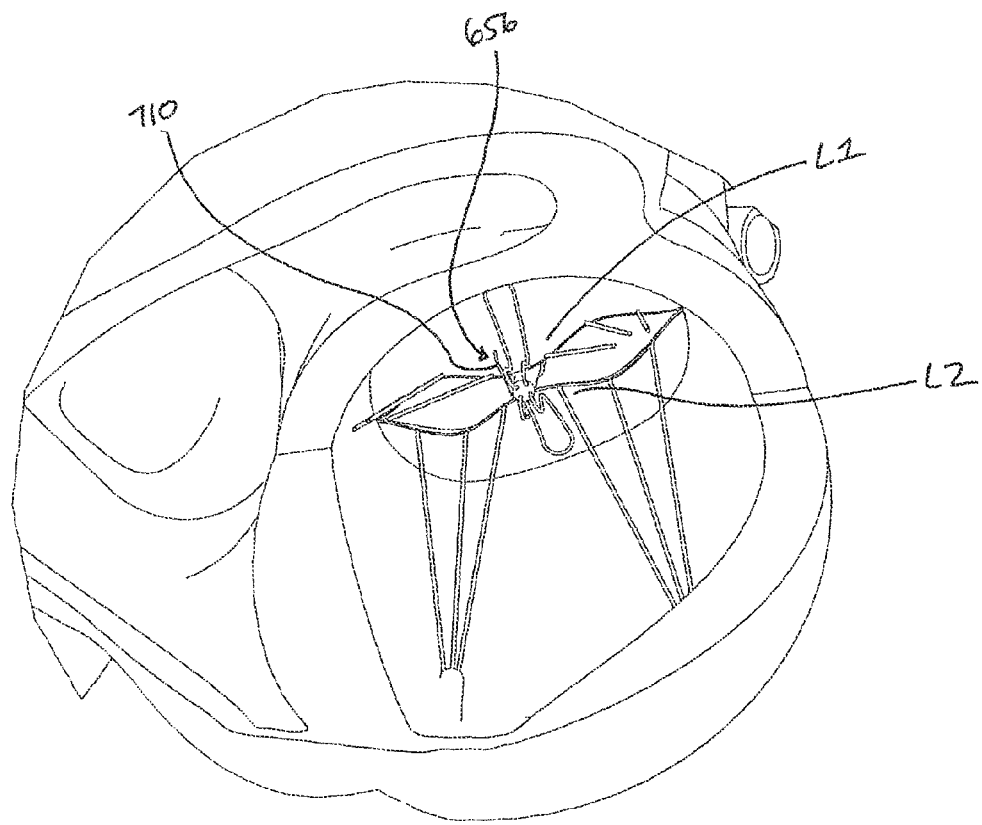

The fastener delivery assembly 658 (and the surgical fastener 656 connected thereto) is then proximally retracted relative to the delivery catheter 652 (and the capture assembly 654) as shown in FIGS. 45G and 45H. For example, the guide sheath 720 and the engagement device 730 (FIG. 44B) can be retracted in tandem. Regardless, retraction of the surgical fastener 656 causes the clips 710, 712 to penetrate through the corresponding mitral valve leaflets L1, L2.

Once the leaflets L1, L2 have been punctured, the surgical fastener 656 is advanced or deployed from the guide sheath distal end 724 such that the clips 710, 712 fully engage the leaflets L1, L2. This further deployment of the surgical fastener 656 is reflected in FIG. 45I. With the leaflets now fully engaged, the petals 682, 684 are retracted into the shaft 680 as shown in FIGS. 45J and 45K. As a point of reference, FIG. 45K reflects the leaflets L1, L2 engaged or fastened to the surgical fastener 656, and the petals 682, 684 withdrawn from the leaflets L1, L2 and into the shaft 680.

The shaft 680 is then retracted back into the delivery catheter 652. The clinician evaluates engagement between the surgical fastener 656 and the leaflets L1, L2. If the clinician is dissatisfied with the achieved engagement, the surgical fastener 656 can be retracted back into the guide sheath 720 and the process repeated until a satisfactory placement is achieved. Once satisfied with placement of the surgical fastener 656, the fastener delivery assembly 658 is operated to completely release the surgical fastener 656 as described above, and the remainder of the system 650 is removed from the patient.

As evidenced by the above description, the repair system 650 is generally configured to deploy and operate the capture assembly 654 and the surgical fastener 656 in a side-by-side manner. Other constructions are also acceptable. For example, FIGS. 46A and 46B illustrate a portion of a related repair system 800 in accordance with the principles of the present disclosure. The system 800 includes a delivery catheter 802 and a capture assembly 804. The system 800 further includes the surgical fastener 656 and the fastener delivery assembly 658 as described above. In more general terms, the system 800 is configured to delivery and deploy the surgical fastener 656 centrally relative to a capture body 806 (referenced generally) provided with the capture assembly 804.

The delivery catheter 802 can assume any of the forms described above, and generally includes or defines a distal section 808 terminating at a distal end 810. Further, a lumen (hidden) is formed through the distal end 810 and sized to slidably receive the capture assembly 804 as described below.

As with the system 650 (FIG. 39) described above, the capture body 806 is collectively defined by first and second petals 820, 822 extending from a shaft 824 in the illustrated normal arrangement. In this regard, the petals 820, 822 can form the shapes previously described, including inverting and leaflet contact segments 826, 828, and each terminate at an atraumatic tip 832. With the construction of FIGS. 46A and 46B, however, each petal 820, 822 is formed by an individual wire 834, 836, respectively, slidably associated with the shaft 824. For example, FIG. 46B illustrates the first wire 834 (forming the first petal 820) as being formed to define first and second side segments 838, 840, with the second side segment 840 terminating at an end 842. The capture assembly 804 includes a rod 844 releasably coupled to the wire end 842 (e.g., the wire end 842 can form a ball, with the rod 844 forming a pocket sized to receive the ball). The first side segment 838 of the wire 834 is slidably disposed within a first guide lumen (obscured in the views) in the shaft 824, whereas the rod 844 is slidably disposed within a second shaft guide lumen (obscured in the views). In the arrangement of FIG. 46B, the rod 844 extends distal a distal end 850 of the shaft 824, thereby locating the wire end 842 outside of the confines of the corresponding guide lumen. Simultaneous retraction of the wire first side segment 838 and the rod 844 proximally retracts the petal 820 toward the shaft 824, locating the wire end 842 within the second guide lumen (e.g., the condition of FIG. 46A). Once so-arranged, the wire end 842 is captured relative to the rod 844, with subsequent proximal or distal simultaneous movement of the first side segment 838 and the rod 844 manipulating the petal 820 in a desired fashion relative to the shaft 824. Once the rod 844 is advanced distal the shaft distal end 850, however, the wire end 842 is freely releasable from the rod 844. A similar coupling is achieved with the second wire 836 and a second rod 852.

During use, the system 800 is initially arranged in a delivery state shown in FIG. 47A. The fastener delivery assembly 658 (FIG. 46A), and the surgical fastener 656 (FIG. 46A) assembled thereto, are retracted within the delivery catheter 802. Similarly, the capture assembly 804 is retracted within the delivery catheter 802. In this regard, the first and second wires 834, 836 are withdrawn into the shaft 824, and the shaft 824, in turn, is retracted within the delivery catheter 802. While a portion of the petal tips 832 may project slightly distal the delivery catheter distal end 810, the system 800 has a low profile in the delivery state, sufficient for traversing the patient's vasculature.

Similar to previous embodiments, the distal section 808 of the delivery catheter 802 is guided into the left atrium through the atrial septum, and located near the center of the mitral valve. As shown in FIG. 47B, the capture assembly 804 is then operated to deploy the petals 820, 822 inside the left ventricle (e.g., the shaft 824 is advanced distally beyond the delivery catheter distal end 810, followed by deployment of the wires 834, 836 from the shaft 824 to form the petals 820, 822). The shaft 824 is then pulled such that the petals 820, 822 contact and draw in the mitral valve leaflets.

With reference to FIG. 47C, the guide sheath 720 is then advanced distally beyond the shaft distal end 850, followed by partial deployment of the surgical fastener 656. Once again, partial deployment of the surgical fastener 656 is sufficient to orientate the tips 718 of the clips 710, 712 back toward the mitral valve. Due to the central location of the fastener delivery assembly 658 relative to the petals 820, 822, desired orientation of the surgical fastener 656 relative to the petals 820, 822 is readily achieved. The fastener delivery assembly 658 is then operated to retract the partially deployed surgical fastener 656 so that the clip tips 718 puncture through the mitral valve leaflets as reflected by FIG. 47D. Further, the shaft 824 is retracted slightly while the guide sheath 720 and the petals 820, 822 remain in the same location (i.e., the shaft 824 is proximally retracted over the wires 834, 836) as shown in FIG. 47E. This motion allows the capture loop 716 of the clips 710, 712 to completely engage the leaflet tissue.

With the leaflets now engaged by the surgical fastener 656, the wires 834, 836 and the corresponding rods 844, 852 are distally advanced relative to the shaft 824 until the end 842 of each of the wires 834, 836 is distally beyond the shaft 824. This relationship is shown in FIG. 46B. The rods 844, 852 are then proximally retracted relative to the shaft 824. In this regard, once the wire ends 842 are distally beyond the shaft 824, the rods 844, 852 easily separate from the corresponding wire end 842. As shown in FIG. 47F, then, the end 842 of each of the wires/petals 834/820, 836/822 is free of or otherwise unattached to the shaft 824. The connected end (or first side segment 838) of the wires 834, 836 is then retracted relative to the shaft 824, pulling the wires 834, 836 back into the shaft 824 as reflected by FIGS. 47G and 47H.

Once the petals 820, 822 (FIG. 47E) are fully retracted into the shaft 824, the surgical fastener 656 can be tested for location and attachment to the valve leaflets. If the clinician is not satisfied with the placement, the surgical fastener 656 can be recaptured and multiple attempts made to properly locate and deploy the surgical fastener 656. In this regard, the entire system 800 (including the delivery catheter 802) must be removed from the patient after the petals 820, 822 (FIG. 47F) have been retracted into the shaft 824 to effectuate reconnection to the corresponding rod 844, 852 (FIG. 47E) before attempting another deployment.

Systems and methods of the present disclosure provide a marked improvement over previous designs. Percutaneous or transcatheter treatment of a patient suffering from mitral valve regurgitation is less invasive and less costly as compared to conventional open-heart surgical valve replacement or repair. By capturing chordae to better ensure edge-to-edge leaflet connection, systems and methods of the present disclosure achieve desired results.

Although the present disclosure has been described with reference to preferred embodiments, workers skilled in the art will recognize that changes can be made in form and detail without departing from the spirit and scope of the present disclosure.

What is claimed is:

1. A system for minimally invasive repair of a mitral valve, the system comprising:
    a delivery catheter terminating at a distal end;
    a capture body including a center portion and opposing, first and second legs extending from the center portion, wherein the capture body is self-transitionable from a collapsed arrangement to a normal arrangement in which extension of the legs from the center portion defines a common wind direction; and
    a surgical fastener including a first self-closing clip configured to self-transition from a deflected arrangement to an undeflected arrangement in which the clip forms a loop;
    wherein the system is configured to provide:
    a delivery state in which the capture body and the surgical fastener are slidably disposed within the catheter and forced to the collapsed arrangement and the deflected arrangement, respectively,
    a chordae capture state in which the capture body legs are distal the distal end and self-assume the normal arrangement for capturing chordae connected to a mitral valve,
    a release state in which the surgical fastener is released from the distal end of the catheter and the clip self-transitions toward the undeflected arrangement for securing edges of opposing leaflets of the mitral valve.

2. The system of claim 1, wherein the center portion of the legs combine to define a hurricane-shape in the normal arrangement.

3. The system of claim 1, wherein the normal arrangement of the capture body includes:
    the center portion having a perimeter defining a circle-like shape;
    the first leg projects relative to the perimeter from a point of departure to a tip in establishing a spacing between the first leg and the perimeter; and
    the second leg projects relative to the perimeter from a point of departure to a tip in establishing a spacing between the second leg and the perimeter.

4. The system of claim 3, wherein in the normal arrangement, a minimum lateral spacing between each of the legs and the perimeter increases from the corresponding point of departure to the corresponding tip, respectively.

5. The system of claim 3, wherein a lateral spacing between the two tips in the normal arrangement is greater than the lateral spacing in the collapsed arrangement.

6. The system of claim 1, wherein the normal arrangement of the capture body is configured to gather chordae between each of the legs and a corresponding region of the center portion upon rotation of the capture body in the wind direction.

7. The system of claim 1, wherein the delivery catheter defines a central axis, and further wherein the chordae capture state includes the legs extending in a plane that is substantially perpendicular to the central axis.

8. The system of claim 1, further comprising:
    a shaft slidably disposed within the delivery catheter and connected to the center portion for manipulating the capture body relative to the delivery catheter.

9. The system of claim 8, wherein the shaft is rotatable relative to the delivery catheter.

10. The system of claim 1, wherein the surgical fastener further includes a second self-closing clip.

11. The system of claim 10, wherein the surgical fastener further includes a base member interconnecting the first and second self-closing clips.

12. The system of claim 11, wherein the second clip is opposite the first clip, the surgical fastener further including:
    a third self-closing clip between the first and second clips; and
    a fourth self-closing clip opposite the third clip.

13. The system of claim 12, further comprising a fastener delivery assembly slidably disposed within the catheter and operable to manipulate the surgical fastener relative to the catheter.

14. The system of claim 13, wherein the fastener delivery assembly includes:
    a push tube terminating at a distal side; and
    a tether disposed within the push tube;
    wherein the delivery state includes the tether connected to the base member and the distal side positioned proximal the base member.

15. The system of claim 14, wherein the fastener delivery assembly is configured to provide a clip deployment state in which at least a portion of the clips are distal the distal end of the delivery catheter, and the base member is within the delivery catheter and connected to the tether.

16. The system of claim 15, wherein the release state includes the tether being disconnected from the base member.

17. A method of repairing a mitral valve of a heart, the mitral valve including opposing leaflets extending from an annulus to define opposing free edges, the leaflets being secured to a left ventricle of the heart by chordae, the method comprising:
    receiving a repair system in a delivery state, the repair system including:
    a delivery catheter terminating at a distal end,
    a capture body including a center portion and opposing first and second legs extending from the center portion, wherein the capture body is self-transitionable to a normal arrangement in which extension of the legs from the center portion defines a common wind direction,
    a surgical fastener including a self-closing clip configured to self-transition to an undeflected arrangement in which the clip forms a loop,
    wherein the delivery state includes the capture body and the surgical fastener disposed entirely within the delivery catheter and forced to a collapsed arrangement and a deflected arrangement, respectively;

advancing the distal end proximate the mitral valve;

deploying the capture body legs from the distal end such that the capture body self-transitions toward the normal arrangement;

rotating the capture body to engage chordae of the opposing leaflets between the legs and the center portion, including drawing the engaged chordae and the corresponding leaflets toward one another; and releasing the surgical fastener from the distal end such that the clip passes through tissue of at least one of the opposing leaflets and the surgical fastener connects the opposing free edges.

18. The method of claim 17, further comprising deploying the clip from the distal end prior to the step of releasing the surgical fastener, wherein the step of deploying the clip includes the capture body legs remaining deployed from the delivery catheter and the clip being located proximal the capture body legs.

19. The method of claim 18, wherein following the step of deploying the clip, the method further comprising:

retracting the capture body within the delivery catheter to force the capture body to the collapsed state; and withdrawing the delivery catheter and the capture body from the patient.

20. The method of claim 17, further comprising:

prior to the step of releasing the surgical fastener from the delivery catheter, evaluating connection of the surgical fastener with the opposing leaflets;

retracting the surgical fastener into the catheter when the evaluation indicates that the leaflets are not adequately captured; and repeating the steps of deploying the capture body legs and rotating the capture body.

\* \* \* \* \*